United States Patent
Fujiyasu et al.

(10) Patent No.: US 9,969,709 B2
(45) Date of Patent: May 15, 2018

(54) GUANIDINOBENZOIC ACID ESTER COMPOUND

(71) Applicant: Takeda Pharmaceutical Company Limited, Chuo-ku, Osaka-shi (JP)

(72) Inventors: Jiro Fujiyasu, Tokyo (JP); Toru Asano, Tokyo (JP); Susumu Yamaki, Tokyo (JP); Osamu Kaneko, Tokyo (JP); Yuka Koike, Tokyo (JP); Tomoyoshi Imaizumi, Tokyo (JP); Yasuharu Urano, Tokyo (JP); Tomohki Satou, Tokyo (JP); Satoshi Sasamura, Tokyo (JP)

(73) Assignee: Takeda Pharmaceutical Company Limited, Osaka (JP)

( * ) Notice: Subject to any disclaimer, the term of this patent is extended or adjusted under 35 U.S.C. 154(b) by 0 days. days.

(21) Appl. No.: 14/775,274

(22) PCT Filed: Mar. 13, 2014

(86) PCT No.: PCT/JP2014/056601
§ 371 (c)(1),
(2) Date: Sep. 11, 2015

(87) PCT Pub. No.: WO2014/142219
PCT Pub. Date: Sep. 18, 2014

(65) Prior Publication Data
US 2016/0031847 A1    Feb. 4, 2016

(30) Foreign Application Priority Data
Mar. 13, 2013  (JP) .................. 2013-050011

(51) Int. Cl.
| C07D 333/70 | (2006.01) |
| C07D 279/18 | (2006.01) |
| C07D 333/24 | (2006.01) |
| C07D 333/68 | (2006.01) |
| C07D 217/26 | (2006.01) |
| C07D 333/40 | (2006.01) |
| C07D 307/81 | (2006.01) |
| A61K 31/24 | (2006.01) |
| A61K 31/343 | (2006.01) |
| A61K 31/381 | (2006.01) |
| A61K 31/472 | (2006.01) |
| C07C 279/18 | (2006.01) |

(52) U.S. Cl.
CPC ............ C07D 333/70 (2013.01); A61K 31/24 (2013.01); A61K 31/343 (2013.01); A61K 31/381 (2013.01); A61K 31/472 (2013.01); C07C 279/18 (2013.01); C07D 217/26 (2013.01); C07D 307/81 (2013.01); C07D 333/24 (2013.01); C07D 333/40 (2013.01); C07D 333/68 (2013.01); C07C 2602/08 (2017.05); C07C 2602/10 (2017.05)

(58) Field of Classification Search
CPC ...................................................... A61K 31/47
USPC ........................................................ 514/307
See application file for complete search history.

(56) References Cited

U.S. PATENT DOCUMENTS

| 4,454,338 A | 6/1984 | Fujii et al. |
| 4,532,255 A | 7/1985 | Fujii et al. |
| 5,116,985 A | 5/1992 | Takeshita et al. |
| 6,388,122 B1 * | 5/2002 | Kido ................ A61K 31/222 544/391 |
| 9,199,927 B2 | 12/2015 | Fujiyasu et al. |
| 9,346,776 B2 | 5/2016 | Ikeda et al. |
| 2008/0009537 A1 | 1/2008 | Sakai |
| 2010/0311690 A1 | 12/2010 | Harosh et al. |
| 2012/0283222 A1 | 11/2012 | Konishi et al. |
| 2013/0338132 A1 | 12/2013 | Koshiba et al. |
| 2014/0094489 A1 | 4/2014 | Suzuki et al. |
| 2014/0378459 A1 | 12/2014 | Fujiyasu et al. |
| 2015/0225354 A1 | 8/2015 | Ikeda et al. |

(Continued)

FOREIGN PATENT DOCUMENTS

| CN | 102822154 A | 12/2012 |
| CN | 105051008 A | 11/2015 |
| EP | 2511271 A1 | 10/2012 |

(Continued)

OTHER PUBLICATIONS

Extended European Search Report dated Jul. 4, 2016 in Patent Application No. 14763790.4.

(Continued)

*Primary Examiner* — Yong L Chu
(74) *Attorney, Agent, or Firm* — Foley & Lardner LLP

(57) ABSTRACT

[Problem]
To provide a compound which is useful as an agent for preventing and/or treating kidney diseases.

[Means for Solution]
The present inventors have studied compounds having a trypsin inhibitory activity, and have confirmed that a guanidinobenzoic acid ester compound has a trypsin inhibitory activity, thereby completing the present invention. The guanidinobenzoic acid ester compound of the present invention can be used as an agent for preventing and/or treating kidney diseases (for example, chronic kidney disease, acute glomerulonephritis, acute kidney injury, and the like) as an agent which will substitute low-protein diet therapy, and/or as an agent for preventing and/or treating trypsin-related diseases (for example, chronic pancreatitis, gastroesophageal reflux disease, hepatic encephalopathy, influenza, and the like).

23 Claims, No Drawings

(56) References Cited

U.S. PATENT DOCUMENTS

2015/0225361 A1  8/2015  Ikeda et al.
2016/0031847 A1  2/2016  Fujiyasu et al.

FOREIGN PATENT DOCUMENTS

| EP | 2 757 093 A1 | 7/2014 |
|---|---|---|
| JP | 52 89640 | 7/1977 |
| JP | 57 53454 | 3/1982 |
| JP | 03-200764 A | 9/1991 |
| JP | 6 192085 | 7/1994 |
| JP | 7 53500 | 2/1995 |
| JP | 8 48664 | 2/1996 |
| JP | 9 124571 | 5/1997 |
| JP | 10-101556 A | 4/1998 |
| JP | 10-251239 A | 9/1998 |
| JP | 10 306025 | 11/1998 |
| WO | 91 18869 | 12/1991 |
| WO | 94 13631 | 6/1994 |
| WO | 97 37969 | 10/1997 |
| WO | WO 2006/050999 A2 | 5/2006 |
| WO | WO 2006/057152 A1 | 6/2006 |
| WO | WO 2006/057551 A1 | 6/2006 |
| WO | WO 2007/087130 A2 | 8/2007 |
| WO | WO 2009/071601 A1 | 6/2009 |
| WO | 2011 071048 | 6/2011 |
| WO | WO 2012/169579 A1 | 12/2012 |
| WO | WO 2013/039187 A1 | 3/2013 |
| WO | WO 2013/102899 A1 | 7/2013 |
| WO | WO 2013/187533 A1 | 12/2013 |
| WO | WO 2014/106846 A2 | 7/2014 |
| WO | WO 2014/138484 A1 | 9/2014 |
| WO | WO 2014/142219 A1 | 9/2014 |
| WO | WO 2015/122187 A1 | 8/2015 |

OTHER PUBLICATIONS

International Search Report dated May 14, 2014 in PCT/JP14/056601 Filed Mar. 13, 2014.

Combined Chinese Office Action and Search Report dated Jun. 23, 2016 in Patent Application No. 201480014813.4 (submitting English translation only).

Naleway et al., "Synthesis and Use of New Fluorogenic Precipitating Substrates," Tetrahedron Letters, Nov. 14, 1994, 35(46):8569-8572.

Zlatoidsky et al., "Synthesis and structure-activity relationship study of the new set of trypsin-like proteinase inhibitors," Eur. J. Med. Chem., Dec. 1, 1999, 34(12):1023-1034.

* cited by examiner

GUANIDINOBENZOIC ACID ESTER COMPOUND

CROSS REFERENCE TO RELATED APPLICATION

This application is a National Stage entry under 35 USC 371 of PCT/JP14/056601, filed on Mar. 13, 2014, and claims priority to Japanese Patent Application No. 2013-050011, filed on Mar. 13, 2013.

TECHNICAL FIELD

The present invention relates to a guanidinobenzoic acid ester compound which is useful as an active ingredient of a pharmaceutical composition, for example, a pharmaceutical composition for treating kidney diseases.

BACKGROUND ART

Low-protein diet therapy for various kidney diseases (for example, chronic kidney diseases, acute glomerulonephritis, and acute kidney injury) has been practiced for a long time. Its mechanism of action has not still been clarified, but is thought to (1) reduce the total amount of the nitrogen compounds derived from protein, and decrease the glomerular loading, (2) suppress the production of uremic toxins derived from protein, which cause renal injury, (3) suppress the accumulation of phosphorous or potassium derived from protein, (4) suppress the production of acids derived from protein, and the like, by inhibiting the intake of the protein derived from diet. The effect of the low-protein diet therapy on inhibiting the progression of the kidney diseases has been proved in the clinical tests that have hitherto been conducted ((a) "The New England Journal of Medicine", 1989, Vol. 321, No. 26, pp. 1773-1777; and (b) "American Journal of Kidney Diseases", 2003, Vol. 41, No. 3, pp. S31-S34), and the intake amount of the protein for a patient with a kidney disease is also established in society guidelines (Japan Society of Nephrology, "Evidence-Based Clinical Practice Guideline for CKD 2013", 2013, pp. 25-30). On the other hand, the low-protein diet therapy has problems of a low extent of long-term strict practice due to necessity for technical knowledge, high cost, and low dietary compliance resulting from taste.

It is known that a compound which inhibits trypsin as one of serine proteases is useful for diseases involving this enzyme, such as pancreatitis and gastroesophageal reflux disease. Indeed, camostat mesylate (which will be hereinafter described Camostat) of the following Formula (A) which is a trypsin inhibitor (Patent Document 1) has been actually used for chronic pancreatitis and gastroesophageal reflux disease in clinical practice. Further, it has also been reported that Camostat has effects of inhibiting the urinary albumin excretion in animal models with diabetes mellitus ("Nephron", 1996, Vol. 74, No. 4, pp. 709-712), and reducing the amount of the urinary protein excretion in a variety of kidney diseases patients ("Clinical Nephrology", 1989, Vol. 32, p. 119-123).

[Chem. 1]

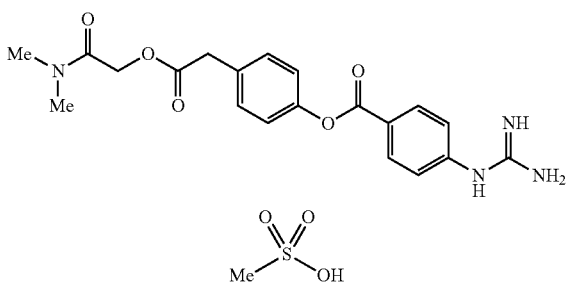

In addition, trypsin is involved in the proliferation of influenza viruses. For example, it is necessary that hemagglutinin (HA) on the virus surface should be cleaved into two subunits of HA1 and HA2 by the trypsin in the airway or mucosal intestinal epithelium in order to obtain the infectivity of the virus. It has been reported that by inhibition of the trypsin, the cleavage of this HA is suppressed and the virus loses infectivity, whereby the proliferation is suppressed. Therefore, a compound inhibits the trypsin can also be used as an anti-influenza drug ((a) "Antiviral Research", 2011, Vol. 92, No. 1, p. 27-36; (b) "Protease Groups of Individuals which Determine Susceptibility to Infection of Influenza Virus and Pathogenesis of Influenza-Associated Encephalopathy", "The Japanese Journal of Pharmacology", 2003, Vol. 122, p. 45-53).

As a compound exhibiting a trypsin inhibitory activity, other than Camostat, Compound (B) (Patent Document 2), Compound (C) (Patent Document 3), Compound (D) (Patent Document 4), Compound (E) (Patent Document 5), Compound (F) (Patent Document 6), Compound (G) (Patent Document 7), and Compound (H) (Patent Document 8) of the following formulae have been reported. However, there is no disclosure of the compound of the formula (I) or a salt thereof of the present application as described later in these documents.

[Chem. 2]

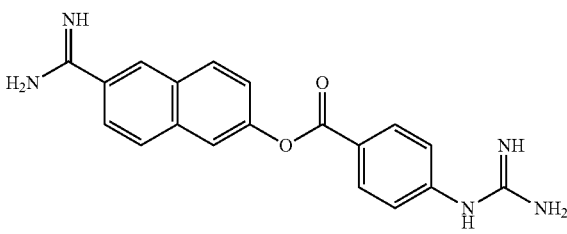

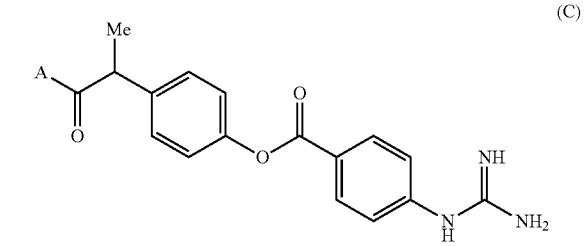

-continued

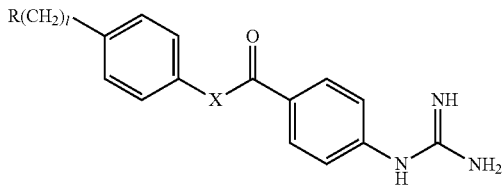
(D)

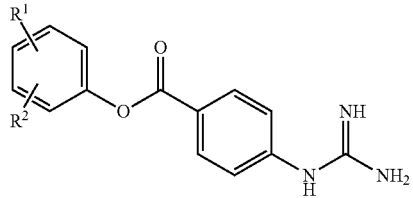
(E)

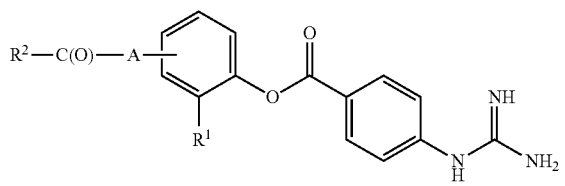
(F)

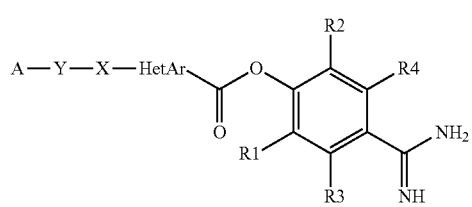
(G)

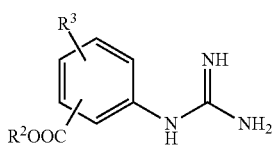
(H)

(In the formula (C), A is —N(R$_1$, R$_2$) or the like, and R$_1$ and R$_2$ are each H, lower alkyl having 1 to 8 carbon atoms, aralkyl which may have a substituent, or the like. In the formula (D), X is an oxygen atom or a sulfur atom, and R is —C(O)N(R$^1$)—(CH$_2$)$_m$-(1-azabicyclo[3.3.0]octan-5-yl) or the like. In the formula (E), R$^1$ is a hydrogen atom or a halogen atom, and R$^2$ is —OCOR$^3$ or the like. In the formula (F), A is (CH$_2$)$_n$ or a styrene group, R$^2$ is —NH(CH$_2$)$_m$COOR$^4$, —NHCH—(—R$^5$)—COOR$^4$, —NH—C$_6$H$_4$—(CH$_2$)$_p$—COOR$^4$, or the like, m is 2 or 3, p is an integer of 0 or 1, R$^4$ is a hydrogen atom, lower alkyl, or a substituted or unsubstituted benzyl group, R$^5$ is a substituted or unsubstituted benzyl group, a methoxycarbonylmethyl group, and the substituent of the substituted benzyl group means a halogen atom, a nitro group, a lower alkyl group, a hydroxy group, an alkoxy group having 2 to 6 carbon atoms, or the like. In the formula (G), X represents lower alkylene or the like, Y represents a carbonyl group or the like, A represents —NR$^6$R$^7$, R$^6$ and R$^7$ may be the same as or different from each other and each represents a hydrogen atom, a lower alkyl group which may have a substituent, or the like, or R$^6$ and R$^7$ may be bonded to each other to form a cyclic amino group which may have a substituent. In the formula (H), R$^2$ is a substituted phenyl group, or the like, and R$^3$ is any of various substituents. For the other symbols, refer to the respective patent publications.)

Furthermore, as a guanidino compound having an effect of inhibiting the production and release of inflammatory cytokines, Compound (J) (Patent Document 9) has been reported. However, there is no disclosure or suggestion of a specific compound as the compound of the formula (I) or a salt thereof of the present application as described later in these documents.

[Chem. 3]

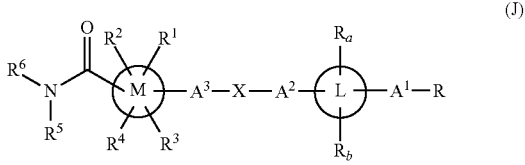
(J)

(wherein R is a guanidino group, an amidino group, or the like; A$^1$, A$^2$ and A$^3$ are each a bond or the like; L is an arylene group or the like; X is —COO— or the like; M is an arylene group or the like, or a divalent heterocyclic group, which has at least one hetero atom selected from a nitrogen atom, a sulfur atom, or an oxygen atom, and may form a fused ring, or the like; R$^5$ is a hydrogen atom or the like; R$^6$ is —CR$^{12}$R$^{13}$—(CH$_2$)$_m$—R$^{11}$ or the like; R$^{12}$ and R$^{13}$ are a hydrogen atom or the like; R$^{11}$ is —COOR$^{16}$ or the like; and R$^{16}$ is a hydrogen atom or the like. For the other symbols, refer to the corresponding patent publications.)

Furthermore, Compound (K) has been reported as a guanidino compound which is useful as a pollen protease inhibitor (Patent Document 10). However, there is no disclosure or suggestion of a specific compound as the compound of Formula (I) or a salt thereof of the present application as described later in this document.

[Chem. 4]

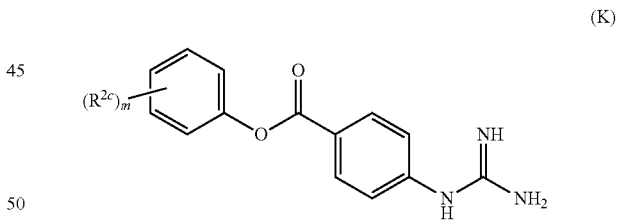
(K)

(wherein R$^{2c}$ represents a Z$^c$CONR$^{5c}$R$^{6c}$ group or the like, Z$^c$ represents a bond or the like, R$^{5c}$ and R$^{6c}$ each independently represent a hydrogen atom, an alkyl group having 1 to 4 carbon atoms, an alkyl group having 1 to 4 carbon atoms, substituted with a COOR$^{4c}$ group, a phenyl group, a benzyl group, a pyridyl group, or the like, and R$^{4c}$ represents an alkyl group having 1 to 4 carbon atoms, a phenyl group, or the like).

Furthermore, a guanidinobenzoic acid derivative (L) which is useful as a house dust mite protease inhibitor has been reported (Patent Document 11). However, there is no disclosure or suggestion of a specific compound as the compound of Formula (I) or a salt thereof of the present application as described later in this document.

[Chem. 5]

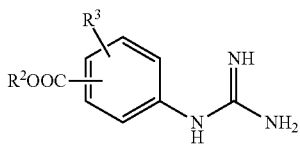

(L)

(wherein $R^2$ represents a phenyl group, a naphthyl group, a substituted phenyl group, or a substituted naphthyl group, and $R^3$ represents one of various substituents).

RELATED ART

Patent Document

Patent Document 1: JP-A-52-089640
Patent Document 2: JP-A-57-053454
Patent Document 3: WO 1994/013631
Patent Document 4: JP-A-7-053500
Patent Document 5: WO 1991/018869
Patent Document 6: JP-A-8-048664
Patent Document 7: WO 2011/071048
Patent Document 8: WO 1997/037969
Patent Document 9: JP-A-9-124571
Patent Document 10: JP-A-10-306025
Patent Document 11: JP-A-6-192085

DISCLOSURE OF INVENTION

Problems to be Solved by the Invention

A guanidinobenzoic acid ester compound, which is useful as an active ingredient of a pharmaceutical composition, for example, a pharmaceutical composition for preventing and/or treating kidney diseases, is provided.

Means for Solving the Problems

The ingested proteins from meals are digested by various enzymes in the duodenum and intestine, and finally absorbed as amino acids or peptides. Trypsin which is produced in the pancreas and secreted in the small intestine in the proteolytic process is an important proteolytic enzyme. Further, by suppressing the enzyme it is expected that the low-protein diet state in which the diet-derived proteolysis is suppressed and the absorption is also suppressed may be mimicked. That is, it is considered that a trypsin inhibitor which acts in the gut may potentially be used as an agent that will substitute low-protein diet therapy. In this regard, the present inventors have conducted extensive studies on compounds having a trypsin inhibitory activity. As a result, they have found that the guanidinobenzoic acid ester compound of the present invention has a trypsin inhibitory activity, and is useful for prevention and treatment of kidney diseases as an agent which will substitute the low-protein diet therapy, thereby completing the present invention.

Specifically, the present invention relates to a compound of the formula (I) or a salt thereof, and a pharmaceutical composition including the compound of the formula (I) or a salt thereof, and an excipient.

[Chem. 6]

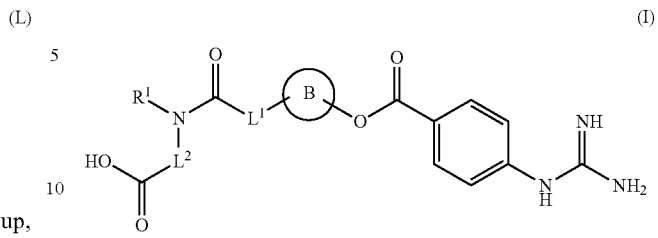

(I)

(in which
$L^1$ is a bond or -lower alkylene-,
$L^2$ is lower alkylene which may be substituted,
$R^1$ is lower alkyl which may be substituted with a substituent selected from the group consisting of aryl which may be substituted, an aromatic heterocyclic group which may be substituted, and —$CO_2H$, or H, or $R^1$ is combined with a nitrogen atom bonded thereto and an $HO_2C$-$L^2$ group on the nitrogen atom to form cyclic amino which may be substituted with —$CO_2H$, and
Ring B is naphthalenediyl, 1,2,3,4-tetrahydronaphthalenediyl, 2,3-dihydroindenediyl, benzothiophenediyl, benzofurandiyl, or 2,3-dihydrobenzofurandiyl).

Furthermore, unless specified otherwise, in the case where the symbols of the formulae in the present specification are also used in other chemical formulae, the same symbols denote the same meanings.

Moreover, the present invention relates to a pharmaceutical composition for preventing and/or treating kidney diseases (for example, chronic kidney disease, acute glomerulonephritis, acute kidney injury, and the like), and/or a pharmaceutical composition for preventing and/or treating trypsin-related diseases (for example, chronic pancreatitis, gastroesophageal reflux disease, hepatic encephalopathy, influenza, and the like), comprising the compound of Formula (I) or a salt thereof. Further, the pharmaceutical composition includes an agent for preventing and/or treating kidney diseases (for example, chronic kidney disease, acute glomerulonephritis, acute kidney injury, and the like), and/or trypsin-related diseases (for example, chronic pancreatitis, gastroesophageal reflux disease, hepatic encephalopathy, influenza, and the like), comprising the compound of Formula (I) or a salt thereof. In one embodiment, the kidney disease is chronic kidney disease. In one embodiment, the chronic kidney disease is diabetic nephropathy, chronic nephritis, nephrotics, nephrosclerosis, or polycystic kidney disease.

In addition, the present invention relates to use of the compound of Formula (I) or a salt thereof for the manufacture of a pharmaceutical composition for preventing and/or treating kidney diseases (for example, chronic kidney disease, acute glomerulonephritis, acute kidney injury, and the like), and/or trypsin-related diseases (for example, chronic pancreatitis, gastroesophageal reflux disease, hepatic encephalopathy, influenza, and the like); use of the compound of Formula (I) or a salt thereof for treating kidney diseases (for example, chronic kidney disease, acute glomerulonephritis, acute kidney injury, and the like), and/or trypsin-related diseases (for example, chronic pancreatitis, gastroesophageal reflux disease, hepatic encephalopathy, influenza, and the like); the compound of Formula (I) or a salt thereof for preventing and/or treating kidney diseases (for example, chronic kidney disease, acute glomerulonephritis, acute kidney injury, and the like), and/or trypsin-related diseases (for example, chronic pancreatitis, gastroesophageal reflux disease, hepatic encephalopathy, influenza, and the like); and a method for preventing and/or treating kidney diseases (for example, chronic kidney disease, acute glomerulonephritis, acute kidney injury, and the like), or trypsin-related diseases (for example, chronic pancreatitis, gastroesophageal reflux disease, hepatic encephalopathy, influenza, and the like), comprising administering an effective amount of the compound of Formula (I) or a salt thereof to a subject. Further, the "subject" is a human or another mammal in need of such prevention or treatment, and in a certain embodiment, a human in need of such prevention or treatment.

Effects of the Invention

The compound of Formula (I) or a salt thereof has a trypsin inhibitory action, and therefore, can be used as an agent for preventing and/or treating kidney diseases (for example, chronic kidney disease, acute glomerulonephritis, acute kidney injury, and the like), as an agent which will substitute low-protein diet therapy, and/or an agent for preventing and/or treating trypsin-related diseases (for example, chronic pancreatitis, gastroesophageal reflux disease, hepatic encephalopathy, influenza, and the like).

EMBODIMENTS FOR CARRYING OUT THE INVENTION

Hereinafter, the present invention will be described in detail.

In the present specification, the "lower alkyl" refers to linear or branched alkyl having 1 to 6 carbon atoms (which is hereinafter simply referred to as $C_{1-6}$), examples of which include methyl, ethyl, propyl, isopropyl, butyl, tert-butyl, pentyl, hexyl, and the like; in another embodiment, $C_{1-3}$ alkyl; in a further embodiment, methyl, ethyl, propyl, or isopropyl; in a still further embodiment, methyl or ethyl; in a still further embodiment, methyl; and in a still further embodiment, ethyl.

The "lower alkylene" refers to a divalent group formed by the removal of any one hydrogen atom of the "lower alkyl", examples of which include methylene, ethylene, trimethylene, tetramethylene, pentamethylene, hexamethylene, methylmethylene, dimethylmethylene, ethylmethylene, isobutylmethylene, methylethylene, dimethylethylene, isobutylene, methylpropylene, ethylethylene, methyltetramethylene, methyltrimethylene, dimethyltetramethylene, and the like; in another embodiment, methylene, methylmethylene, and ethylene; in a further embodiment, $C_{1-3}$ alkylene; in a still further embodiment, methylene, and ehtylene; in a still further embodiment, methylene; and in a still further embodiment, ethylene.

The "aryl" refers to a monocyclic to tricyclic aromatic hydrocarbon ring group having 6 to 14 carbon atoms, and specifically, phenyl, naphthyl, anthranyl and the like; in a further embodiment, phenyl; and in a still further embodiment, naphthyl.

The "aromatic heterocyclic group" is an aromatic monocyclic heterocyclic group having 5 to 6 ring members, containing at least one hetero atom selected from O, N, and S as a ring-constituting atom, or an aromatic bicyclic heterocyclic group formed by fusion of the aromatic monocyclic heterocycle with a benzene ring or a thiophene ring, specific examples of which include pyrrolyl, furyl, thienyl, pyrazolyl, imidazolyl, oxazolyl, thiazolyl, oxadiazolyl, thiadiazolyl, tetrazolyl, pyridyl, pyridazinyl, pyrimidinyl, pyrazinyl, indolyl, isoindolyl, benzofuryl, benzothienyl, indazolyl, benzoimidazolyl, benzoxazolyl, benzothiazolyl, quinolyl, isoquinolyl, cinnolinyl, phthalazinyl, quinazolinyl, quinoxalinyl, thienopyridyl, thienopyrimidinyl, thienopyrazinyl, and the like; in one embodiment, an aromatic monocyclic heterocyclic group; in another embodiment, an aromatic bicyclic heterocyclic group; in a further embodiment, thienyl, imidazolyl, thiazolyl, oxadiazolyl, tetrazolyl, indolyl, and benzothienyl; and in a still further embodiment, thienyl and benzothienyl.

The "non-aromatic heterocyclic group" is a non-aromatic monocyclic heterocyclic group having 3 to 7 ring members, containing at least one hetero atom selected from O, N, and S as a ring-constituting atom, or a non-aromatic bicyclic heterocyclic group formed by fusion of the non-aromatic heterocycle with a benzene ring, a thiophene ring, or a cyclohexane ring, in which a part of the bonds may be unsaturated. Further, the sulfur atom that is a ring-constituting atom may be oxidized. The non-aromatic heterocycle may also be substituted with -oxo. Specific examples thereof include azepanyl, diazepanyl, aziridinyl, azetidinyl, pyrrolidinyl, imidazolidinyl, piperidyl, pyrazolidinyl, piperazinyl, azocanyl, thiomorpholinyl, thiazolidinyl, 1,1-dioxidothiazolidinyl, isothiazolidinyl, 1,1-dioxidoisothiazolidinyl, oxazolidinyl, morpholinyl, 1,1-dioxidothiomorpholinyl, indolinyl, isoindolinyl, tetrahydroquinolyl, tetrahydroisoquinolyl, and the like; in another embodiment, pyrrolidinyl, tetrahydroquinolyl, and tetrahydroisoquinolyl; in a further embodiment, tetrahydroquinolyl and tetrahydroisoquinolyl; and in a still further embodiment, tetrahydroisoquinolyl.

The "cyclic amino" is a non-aromatic heterocyclic group having a nitrogen atom, which has a bonding arm on the nitrogen atom, among the above "non-aromatic heterocyclic groups". Specific examples of the cyclic amino include azepan-1-yl, pyrrolidin-1-yl, piperidin-1-yl, piperazin-1-yl, thiomorpholin-4-yl, thiazolidin-3-yl, 1,1-dioxidothiazolidin-3-yl, isothiazolidin-2-yl, 1,1-dioxidoisothiazolidin-2-yl, oxazolidin-3-yl, morpholin-4-yl, 1,1-dioxidothiomorpholin-4-yl, indolin-1-yl, isoindolin-2-yl, 1,2,3,4-tetrahydroquinolin-1-yl, 1,2,3,4-tetrahydroisoquinolin-2-yl, and the like; in another embodiment, 1,2,3,4-tetrahydroquinolin-1-yl and 1,2,3,4-tetrahydroisoquinolin-2-yl; and in a further embodiment, 1,2,3,4-tetrahydroisoquinolin-2-yl.

The "halogen" refers to F, Cl, Br, or I; and in another embodiment, F or Cl.

In one embodiment of the "naphthalenediyl", naphthalene-1,6-diyl or naphthalene-2,6-diyl is involved; in one embodiment of "1,2,3,4-tetrahydronaphthalenediyl", 1,2,3,4-tetrahydronaphthalene-1,6-diyl or 1,2,3,4-tetrahydronaphthalene-2,6-diyl is involved; in one embodiment of "2,3-dihydroindenediyl", 2,3-dihydroindene-1,5-diyl is involved; in one embodiment of "benzothiophenediyl", benzothiophene-2,6-diyl or benzothiophene-3,6-diyl is involved; in one embodiment of "benzofurandiyl", benzofuran-3,6-diyl is involved; and in one embodiment of "2,3-dihydrobenzofurandiyl", 2,3-dihydrobenzofuran-3,6-diyl is involved.

The "biological equivalent of $-CO_2H$" means another atom or atom group having common biological properties equivalent to $-CO_2H$, which is capable of releasing acidic protons. Examples thereof include $-C(O)-NH-OH$, $-C(O)-NH-O$-lower alkyl, $-C(O)-NH-CN$, $-C(O)-NH-S(O)_2$-lower alkyl, $-C(O)-NH-S(O)_2-N$(lower alkyl)$_2$, tetrazolyl, oxadiazolonyl, oxadiazolethionyl, oxathiadiazolyl, thiadiazolonyl, triazolethionyl, hydroxyisoxazolyl, and the like; in another embodiment, —C(O)—NH—S(O)$_2$-lower alkyl, —C(O)—NH—S(O)$_2$—N(lower alkyl)$_2$, and tetrazolyl; and in a further embodiment, tetrazolyl.

In the present specification, the expression "which may be substituted" represents non-substitution or substitution with 1 to 5 substituents". Further, regarding having a plurality of substituents, the substituents may be the same as or different from one another.

Examples of the substituent in the "lower alkylene which may be substituted" in L$^2$ of Formula (I) include substituents selected from Group D1.

Group D1:
(1) halogen,
(2) —OH and —O-lower alkyl,
(3) —SH and —S-lower alkyl,
(4) —S(O)-lower alkyl and —S(O)$_2$-lower alkyl,
(5) —CN,
(6) —NO$_2$,
(7) —NH$_2$, —NH-(lower alkyl), and —N(lower alkyl)$_2$,
(8) —C(O)-lower alkyl,
(9) aryl substituted with at least one substituent selected from the group consisting of lower alkyl which may be substituted with at least one substituent selected from the group consisting of halogen and —CO$_2$H, —O-(lower alkyl which may be substituted with at least one —CO$_2$H group), halogen, and —CO$_2$H, and
(10) —C(O)—O-lower alkyl and —CO$_2$H or a biological equivalent thereof.

In another embodiment, Group D1 includes:
(1) aryl substituted with at least one —CO$_2$H group, and
(2) —CO$_2$H.

Examples of the substituent in the "aryl which may be substituted" and the "aromatic heterocyclic group which may be substituted" in R$^1$ of Formula (I) include substituents selected from Group D2.

Group D2:
(1) halogen,
(2) —OH and —O-lower alkyl,
(3) —SH and —S-lower alkyl,
(4) —S(O)-lower alkyl and —S(O)$_2$-lower alkyl,
(5) —CN,
(6) —NO$_2$,
(7) —NH$_2$, —NH-(lower alkyl), and —N(lower alkyl)$_2$,
(8) —C(O)-lower alkyl,
(9) —C(O)—NH$_2$, —C(O)—NH-(lower alkyl), and —C(O)—N(lower alkyl)$_2$,
(10) —C(O)—O-lower alkyl and —CO$_2$H or a biological equivalent thereof, and
(11) lower alkyl and —O-lower alkyl, each of which may be substituted with at least one substituent selected from the group consisting of the substituents described in (1) to (10) above.

In another embodiment, Group D2 includes:
(1) —CO$_2$H, and
(2) lower alkyl substituted with at least one —CO$_2$H group.

One embodiment of the compound of Formula (I) or a salt thereof is shown below.

(1) The compound or a salt thereof, in which L$^1$ is a bond or methylene; in another embodiment, the compound or a salt thereof, in which L$^1$ is a bond; in a further embodiment, the compound or a salt thereof, in which L$^1$ is lower alkylene; in a still further embodiment, the compound or a salt thereof, in which L$^1$ is methylene; and in a still further embodiment, the compound or a salt thereof, in which L$^1$ is a bond or C$_{1-3}$ alkylene.

(2) The compound or a salt thereof, in which L$^2$ is lower alkylene which may be substituted with a substituent selected from Group D1; in another embodiment, the compound or a salt thereof, in which L$^2$ is lower alkylene which may be substituted with at least one substituent selected from the group consisting of aryl substituted with at least one —CO$_2$H group, and —CO$_2$H; in a further embodiment, the compound or a salt thereof, in which L$^2$ is lower alkylene; in a still further embodiment, the compound or a salt thereof, in which L$^2$ is C$_{1-3}$ alkylene; in a still further embodiment, the compound or a salt thereof, in which L$^2$ is methylene, ethylene, or ethylene substituted with (phenyl substituted with —CO$_2$H); in a still further embodiment, the compound or a salt thereof, in which L$^2$ is methylene; in a still further embodiment, the compound or a salt thereof, in which L$^2$ is ethylene substituted with (phenyl substituted with —CO$_2$H); in a still further embodiment, the compound or a salt thereof, in which L$^2$ is methylene, methylmethylene, ethylene, 2-(carboxymethyl)trimethylene, or methylmethylene substituted with (phenyl substituted with —CO$_2$H); in a still further embodiment, the compound or a salt thereof, in which L$^2$ is methylene, methylmethylene, ethylene, or methylmethylene substituted with (phenyl substituted with —CO$_2$H); in a still further embodiment, the compound or a salt thereof, in which L$^2$ is methylene, methylmethylene, or methylmethylene substituted with (phenyl substituted with —CO$_2$H); in a still further embodiment, the compound or a salt thereof, in which L$^2$ is C$_{1-3}$ alkylene substituted with (phenyl substituted with —CO$_2$H); in a still further embodiment, the compound or a salt thereof, in which L$^2$ is methylene or methylmethylene; in a still further embodiment, the compound or a salt thereof, in which L$^2$ is methylmethylene substituted with (phenyl substituted with —CO$_2$H).

(3) The compound or a salt thereof, in which R$^1$ is lower alkyl which may be substituted with at least one substituent selected from the group consisting of i) aryl which may be substituted with a substituent selected from Group D2, ii) an aromatic heterocyclic group which may be substituted with a substituent selected from Group D2, and iii) —CO$_2$H, or H; in another embodiment, the compound or a salt thereof, in which R$^1$ is lower alkyl which may be substituted with at least one substituent selected from the group consisting of i) aryl substituted with a substituent selected from Group D2, ii) an aromatic heterocyclic group substituted with a substituent selected from Group D2, and iii) —CO$_2$H, or H; in a further embodiment, the compound or a salt thereof, in which R$^1$ is lower alkyl which may be substituted with at least one substituent selected from the group consisting of i) aryl substituted with at least one substituent selected from the group consisting of —CO$_2$H and lower alkyl substituted with —CO$_2$H, ii) an aromatic heterocyclic group substituted with at least one substituent selected from the group consisting of —CO$_2$H and lower alkyl substituted with —CO$_2$H, and iii) —CO$_2$H, or H; in a still further embodiment, the compound or a salt thereof, in which R$^1$ is lower alkyl which may be substituted with at least one substituent selected from the group consisting of i) phenyl substituted with at least one substituent selected from the group consisting of —CO$_2$H and lower alkyl substituted with —CO$_2$H, ii) thienyl substituted with at least one substituent selected from the group consisting of —CO$_2$H and lower alkyl substituted with —CO$_2$H, and iii) —CO$_2$H, or H; in a still further embodiment, the compound or a salt thereof, in which R$^1$ is lower alkyl substituted with at least one substituent selected from the group consisting of i) phenyl substituted with at least one substituent selected from the group consisting of —CO$_2$H and lower alkyl substituted with —CO$_2$H, ii) thienyl substituted with at least one substituent selected from the group consisting of —CO$_2$H and lower alkyl substituted with —CO$_2$H, and iii) —CO$_2$H, or H; in a still further embodiment, the compound or a salt thereof, in which R$^1$ is (phenyl substituted with at least one substituent selected from the group consisting of —CO$_2$H and lower alkyl substituted with —CO$_2$H)—CH$_2$—, (thienyl substituted with at least one substituent selected from the group consisting of —CO$_2$H and lower alkyl substituted with —CO$_2$H)—CH$_2$—, or H; in a still further embodiment, the compound or a salt thereof, in which R$^1$ is (phenyl substituted with at least one substituent selected from the group consisting of —CO$_2$H and lower alkyl substituted with —CO$_2$H)—CH$_2$—; in a still further embodiment, the compound or a salt thereof, in which R$^1$ is lower alkyl substituted with thienyl substituted with at least one —CO$_2$H group; in a still further embodiment, the compound or a salt thereof, in which R$^1$ is (thienyl substituted with at least one —CO$_2$H group)-CH$_2$—; in a still further embodiment, the compound or a salt thereof, in which R$^1$ is (phenyl substituted with at least one substituent selected from the group consisting of —CO$_2$H and lower alkyl substituted with —CO$_2$H)—CH$_2$—, (thienyl substituted with at least one —CO$_2$H group)-CH$_2$—, or H; in a still further embodiment, the compound or a salt thereof, in which R$^1$ is H; in a still further embodiment, the compound or a salt thereof, in which R$^1$ is lower alkyl which may be substituted with at least one substituent selected from the group consisting of i) aryl which may be substituted with a substituent selected from Group D2, ii) an aromatic heterocyclic group which may be substituted with a substituent selected from Group D2, and iii) —CO$_2$H, or H, or R$^1$ is combined with a nitrogen atom bonded thereto and an HO$_2$C-L$^2$ group on the nitrogen atom to form 1,2,3,4-tetrahydroisoquinolin-2-yl substituted with at least one —CO$_2$H group; in a still further embodiment, the compound or a salt thereof, in which R$^1$ is lower alkyl which is substituted with at least one substituent selected from the group consisting of i) phenyl which may be substituted with at least one substituent selected from the group consisting of —CO$_2$H and lower alkyl substituted with —CO$_2$H, and ii) an aromatic heterocyclic group selected from thienyl and benzothienyl substituted with at least one substituent selected from the group consisting of —CO$_2$H and lower alkyl substituted with —CO$_2$H, and may be substituted with at least one —CO$_2$H group, or H, or R$^1$ is combined with a nitrogen atom bonded thereto and an HO$_2$C-L$^2$ group on the nitrogen atom to form 1,2,3,4-tetrahydroisoquinolin-2-yl substituted with two —CO$_2$H groups; in a still further embodiment, the compound or a salt thereof, in which R$^1$ is lower alkyl substituted with at least one substituent selected from the group consisting of i) phenyl substituted with at least one substituent selected from the group consisting of —CO$_2$H and lower alkyl substituted with —CO$_2$H, ii) thienyl substituted with at least one substituent selected from the group consisting of —CO$_2$H and lower alkyl substituted with —CO$_2$H, iii) benzothienyl substituted with —CO$_2$H, and iv) —CO$_2$H, or H; in a still further embodiment, the compound or a salt thereof, in which R$^1$ is (phenyl substituted with —CO$_2$H)—CH$_2$—, (phenyl substituted with —CH$_2$—CO$_2$H)—CH$_2$—, or (thienyl substituted with —CO$_2$H)—CH$_2$—; in a still further embodiment, the compound or a salt thereof, in which R$^1$ is combined with a nitrogen atom bonded thereto and an HO$_2$C-L$^2$ group on the nitrogen atom to form 1,2,3,4-tetrahydroisoquinolin-2-yl substituted with two —CO$_2$H groups; in a still further embodiment, the compound or a salt thereof, in which R$^1$ is lower alkyl which is substituted with at least one substituent selected from the group consisting of i) phenyl which may be substituted with at least one substituent selected from the group consisting of —CO$_2$H and lower alkyl substituted with —CO$_2$H, and ii) an aromatic heterocyclic group selected from thienyl and benzothienyl substituted with at least one substituent selected from the group consisting of —CO$_2$H and lower alkyl substituted with —CO$_2$H, and may be substituted with at least one —CO$_2$H group; in a still further embodiment, the compound or a salt thereof, in which R$^1$ is lower alkyl substituted with at least one substituent selected from the group consisting of i) phenyl substituted with at least one substituent selected from the group consisting of —CO$_2$H and lower alkyl substituted with —CO$_2$H, and ii) thienyl substituted with at least one substituent selected from the group consisting of —CO$_2$H and lower alkyl substituted with —CO$_2$H.

(4) The compound or a salt thereof, in which Ring B is naphthalenediyl, 1,2,3,4-tetrahydronaphthalenediyl, 2,3-dihydroindenediyl, or benzothiophenediyl; in another embodiment, the compound or a salt thereof, in which Ring B is naphthalene-1,6-diyl, naphthalene-2,6-diyl, 1,2,3,4-tetrahydronaphthalene-1,6-diyl, 1,2,3,4-tetrahydronaphthalene-2,6-diyl, 2,3-dihydroindene-1,5-diyl, or benzothiophene-3,6-diyl; in a further embodiment, the compound or a salt thereof, in which Ring B is naphthalene-1,6-diyl, 1,2,3,4-tetrahydronaphthalene-1,6-diyl, or 1,2,3,4-tetrahydronaphthalene-2,6-diyl; in a still further embodiment, the compound or a salt thereof, in which Ring B is naphthalene-1,6-diyl, 1,2,3,4-tetrahydronaphthalene-1,6-diyl in which the position 1 of 1,2,3,4-tetrahydronaphthalenediyl is bonded with L$^1$, or 1,2,3,4-tetrahydronaphthalene-2,6-diyl in which the position 2 of 1,2,3,4-tetrahydronaphthalenediyl is bonded with L$^1$; in a still further embodiment, the compound or a salt thereof, in which Ring B is 1,2,3,4-tetrahydronaphthalene-1,6-diyl having the position 1 bonded with L$^1$, or 1,2,3,4-tetrahydronaphthalene-2,6-diyl having the position 2 bonded with L$^1$; in a still further embodiment, the compound or a salt thereof, in which Ring B is 1,2,3,4-tetrahydronaphthalene-1,6-diyl having the position 1 bonded with L$^1$; in a still further embodiment, the compound or a salt thereof, in which Ring B is 1,2,3,4-tetrahydronaphthalene-2,6-diyl having the position 2 bonded with L$^1$; in a still further embodiment, the compound or a salt thereof, in which Ring B is naphthalene-1,6-diyl, naphthalene-2,6-diyl, 1,2,3,4-tetrahydronaphthalene-1,6-diyl, 1,2,3,4-tetrahydronaphthalene-2,6-diyl, 2,3-dihydroindene-1,5-diyl, benzothiophene-3,6-diyl, benzofuran-3,6-diyl, or 2,3-dihydrobenzofuran-3,6-diyl.

(5) The compound or a salt thereof, in which -L$^1$-Ring B- is -lower alkylene-(1,2,3,4-tetrahydronaphthalenediyl, 2,3-dihydroindenediyl, benzofurandiyl, or 2,3-dihydrobenzofurandiyl); in another embodiment, the compound or a salt thereof, in which -L$^1$-Ring B- is —CH$_2$-(1,2,3,4-tetrahydronaphthalenediyl, 2,3-dihydroindenediyl, benzofurandiyl, or 2,3-dihydrobenzofurandiyl); in a further embodiment, the compound or a salt thereof, in which -L$^1$-Ring B- is —CH$_2$-(1,2,3,4-tetrahydronaphthalenediyl) or —CH$_2$-(2,3-dihydroindenediyl); in a still further embodiment, the compound or a salt thereof, in which -L$^1$-Ring B- is —CH$_2$-(1,2,3,4-tetrahydronaphthalenediyl); in a still further embodiment, the compound or a salt thereof, in which -L$^1$-Ring B- is CH$_2$-(2,3-dihydroindenediyl); in a still further embodiment, the compound or a salt thereof, in which -L$^1$-Ring B- is —CH$_2$-(1,2,3,4-tetrahydronaphthalene-1,6-diyl) or —CH$_2$-(1,2,3,4-tetrahydronaphthalene-2,6-diyl); in a still further embodiment, the compound or a salt thereof, in which -$L^1$-Ring B- is —$CH_2$-(1,2,3,4-tetrahydronaphthalene-1,6-diyl); in a still further embodiment, the compound or a salt thereof, in which -$L^1$-Ring B- is —$CH_2$-(1,2,3,4-tetrahydronaphthalene-2,6-diyl); in a still further embodiment, the compound or a salt thereof, in which -$L^1$-Ring B- is —$CH_2$-(1,2,3,4-tetrahydronaphthalene-1,6-diyl) in which $CH_2$ is bonded with the position 1 of 1,2,3,4-tetrahydronaphthalenediyl; in a still further embodiment, the compound or a salt thereof, in which -$L^1$-Ring B- is —$CH_2$-(1,2,3,4-tetrahydronaphthalene-2,6-diyl) in which $CH_2$ is bonded with the position 2 of 1,2,3,4-tetrahydronaphthalenediyl.

(6) The compound or a salt thereof, which is a combination of any two or more of the embodiments as described in (1) to (5) above.

The compound or a salt thereof, which is a combination of any two or more of the embodiments of (1) to (5) above, as described in (6) above, is also included in the present invention, and the specific examples thereof also include the following embodiments.

(7) The compound or a salt thereof, in which $L^1$ is a bond or methylene, $L^2$ is lower alkylene which may be substituted with a substituent selected from Group D1, $R^1$ is lower alkyl which may be substituted with at least one substituent selected from the group consisting of i) aryl which may be substituted with a substituent selected from Group D2, ii) an aromatic heterocyclic group which may be substituted with a substituent selected from Group D2, and iii) —$CO_2H$, or H, and Ring B is naphthalenediyl, 1,2,3,4-tetrahydronaphthalenediyl, 2,3-dihydroindenediyl, or benzothiophenediyl.

(8) The compound or a salt thereof as described in (7), in which $L^2$ is methylene, ethylene, or ethylene substituted with (phenyl substituted with —$CO_2H$).

(9) The compound or a salt thereof as described in (7), in which $L^2$ is methylene, methylmethylene, ethylene, or methylmethylene substituted with (phenyl substituted with —$CO_2H$).

(10) The compound or a salt thereof as described in (8) or (9), in which $R^1$ is lower alkyl which may be substituted with at least one substituent selected from the group consisting of i) phenyl substituted with at least one substituent selected from the group consisting of —$CO_2H$ and lower alkyl substituted with —$CO_2H$, ii) thienyl substituted with at least one substituent selected from the group consisting of —$CO_2H$ and lower alkyl substituted with —$CO_2H$, and iii) —$CO_2H$, or H.

(11) The compound or a salt thereof as described in (10), in which Ring B is naphthalene-1,6-diyl, naphthalene-2,6-diyl, 1,2,3,4-tetrahydronaphthalene-1,6-diyl, 1,2,3,4-tetrahydronaphthalene-2,6-diyl, 2,3-dihydroindene-1,5-diyl, or benzothiophene-3,6-diyl.

(12) The compound or a salt thereof as described in (11), in which $L^2$ is methylene or methylmethylene, and $R^1$ is lower alkyl substituted with at least one substituent selected from the group consisting of i) phenyl substituted with at least one substituent selected from the group consisting of —$CO_2H$ and lower alkyl substituted with —$CO_2H$, and ii) thienyl substituted with at least one substituent selected from the group consisting of —$CO_2H$ and lower alkyl substituted with —$CO_2H$, or $L^2$ is methylmethylene substituted with (phenyl substituted with —$CO_2H$), and $R^1$ is H.

(13) The compound or a salt thereof as described in (12), in which $L^2$ is methylene or methylmethylene, and $R^1$ is (phenyl substituted with —$CO_2H$)—$CH_2$—, (phenyl substituted with —$CH_2$—$CO_2H$)—$CH_2$—, or (thienyl substituted with —$CO_2H$)—$CH_2$—.

(14) The compound or a salt thereof as described in (12), in which $L^2$ is methylmethylene substituted with (phenyl substituted with —$CO_2H$), and $R^1$ is H.

(15) The compound or a salt thereof, in which $L^1$ is a bond or $C_{1-3}$ alkylene, $L^2$ is lower alkylene which may be substituted with a substituent selected from Group D1, $R^1$ is lower alkyl which may be substituted with at least one substituent selected from the group consisting of i) aryl which may be substituted with a substituent selected from Group D2, ii) an aromatic heterocyclic group which may be substituted with a substituent selected from Group D2, and iii) —$CO_2H$, or H, or $R^1$ is combined with a nitrogen atom bonded thereto and an $HO_2C$-$L^2$ group on the nitrogen atom to form 1,2,3,4-tetrahydroisoquinolin-2-yl substituted with at least one —$CO_2H$ group.

(16) The compound or a salt thereof as described in (15), in which $L^1$ is a bond or methylene, Ring B is naphthalene-1,6-diyl, naphthalene-2,6-diyl, 1,2,3,4-tetrahydronaphthalene-1,6-diyl, 1,2,3,4-tetrahydronaphthalene-2,6-diyl, 2,3-dihydroindene-1,5-diyl, benzothiophene-3,6-diyl, benzofuran-3,6-diyl, or 2,3-dihydrobenzofuran-3,6-diyl, and a) $L^2$ is $C_{1-3}$ alkylene, and $R^1$ is lower alkyl which is substituted with at least one substituent selected from the group consisting of i) phenyl which may be substituted with at least one substituent selected from the group consisting of —$CO_2H$ and lower alkyl substituted with —$CO_2H$, and ii) an aromatic heterocyclic group selected from thienyl and benzothienyl substituted with at least one substituent selected from the group consisting of —$CO_2H$ and lower alkyl substituted with —$CO_2H$, and may be substituted with at least one —$CO_2H$ group, b) $L^2$ is $C_{1-3}$ alkylene substituted with (phenyl substituted with —$CO_2H$), and $R^1$ is H, or c) $R^1$ is combined with a nitrogen atom bonded thereto and an $HO_2C$-$L^2$ group on the nitrogen atom to form 1,2,3,4-tetrahydroisoquinolin-2-yl substituted with two —$CO_2H$ groups.

Examples of the specific compounds included in the compound of Formula (I) or a salt thereof include the following compounds:

4-{[{6-[(4-carbamimidamidobenzoyl)oxy]-2-naphthoyl}(carboxymethyl)amino]methyl}thiophene-2-carboxylic acid, 3-{[({6-[(4-carbamimidamidobenzoyl)oxy]-1,2,3,4-tetrahydronaphthalen-1-yl}acetyl)(carboxymethyl)amino]methyl}benzoic acid, 3-{[({(1R)-6-[(4-carbamimidamidobenzoyl)oxy]-1,2,3,4-tetrahydronaphthalen-1-yl}acetyl)(carboxymethyl)amino]methyl}benzoic acid, 3-{[({(1S)-6-[(4-carbamimidamidobenzoyl)oxy]-1,2,3,4-tetrahydronaphthalen-1-yl}acetyl)(carboxymethyl)amino]methyl}benzoic acid, N-{6-[(4-carbamimidamidobenzoyl)oxy]-1-naphthoyl}-4-carboxy-L-phenylalanine, 4-{[({6-[(4-carbamimidamidobenzoyl)oxy]-1,2,3,4-tetrahydronaphthalen-2-yl}carbonyl)(carboxymethyl)amino]methyl}thiophene-2-carboxylic acid, 3-{[({5-[(4-carbamimidamidobenzoyl)oxy]-2,3-dihydro-1H-inden-1-yl}acetyl)(carboxymethyl)amino]methyl}benzoic acid, 4-{[({6-[(4-carbamimidamidobenzoyl)oxy]-1-benzothiophen-3-yl}carbonyl)(carboxymethyl)amino]methyl}thiophene-2-carboxylic acid, 3-{[{6-[(4-carbamimidamidobenzoyl)oxy]-1-naphthoyl}(carboxymethyl)amino]methyl}benzoic acid, N-{6-[(4-carbamimidamidobenzoyl)oxy]-1-naphthoyl}-N-[4-(carboxymethyl)benzyl]glycine, 4-({({6-[(4-carbamimidamidobenzoyl)oxy]-1,2,3,4-tetrahydronaphthalen-1-yl}acetyl)[(1R)-1-carboxyethyl]amino}methyl)thiophene-2-carboxylic acid, 4-({({6-[(4-carbamimidamidobenzoyl)oxy]-1,2,3,4-tetrahydronaphthalen-2-yl}carbonyl)[(1R)-1-carboxyethyl]amino}methyl)thiophene-2-carboxylic acid, or N-({6-[(4-carbamimidamidobenzoyl)oxy]-1-benzothiophen-3-yl}carbonyl)-N-[4-(carboxymethyl)benzyl]glycine, or a salt thereof.

The compound of the formula (I) may exist in the form of tautomers or geometrical isomers depending on the kind of substituents. In the present specification, the compound of the formula (I) shall be described in only one form of isomer, yet the present invention includes other isomers, isolated forms of the isomers, or a mixture thereof.

In addition, the compound of the formula (I) may have asymmetric carbon atoms or axial asymmetry in some cases, and correspondingly, it may exist in the form of optical isomers based thereon. The present invention includes both an isolated form of the optical isomers of the compound of the formula (I) or a mixture thereof.

Moreover, the present invention also includes a pharmaceutically acceptable prodrug of the compound represented by the formula (I). The pharmaceutically acceptable prodrug is a compound having a group that can be converted into an amino group, a hydroxyl group, a carboxyl group, or the like through solvolysis or under physiological conditions. Examples of the group forming the prodrug include the groups described in Prog. Med., 5, 2157-2161 (1985) and "Pharmaceutical Research and Development" (Hirokawa Publishing Company, 1990), Vol. 7, Molecular Design, 163-198.

Furthermore, the salt of the compound of the formula (I) is a pharmaceutically acceptable salt of the compound of the formula (I) and may form an acid addition salt or a salt with a base depending on the kind of substituents. Specific examples thereof include acid addition salts with inorganic acids such as hydrochloric acid, hydrobromic acid, hydroiodic acid, sulfuric acid, nitric acid, phosphoric acid, and the like, and with organic acids such as formic acid, acetic acid, propionic acid, oxalic acid, malonic acid, succinic acid, fumaric acid, maleic acid, lactic acid, malic acid, mandelic acid, tartaric acid, dibenzoyltartaric acid, ditoluoyltartaric acid, citric acid, methanesulfonic acid, ethanesulfonic acid, benzenesulfonic acid, p-toluenesulfonic acid, aspartic acid, glutamic acid, and the like, and salts with inorganic bases such as sodium, potassium, magnesium, calcium, aluminum, and the like or organic bases such as methylamine, ethylamine, ethanolamine, lysine, ornithine, and the like, salts with various amino acids or amino acid derivatives such as acetylleucine and the like, ammonium salts, etc.

In addition, the present invention also includes various hydrates or solvates, and polymorphic crystalline substances of the compound of the formula (I) and salts thereof. In addition, the present invention also includes compounds labeled with various radioactive or non-radioactive isotopes.

(Preparation Methods)

The compound of the formula (I) and a salt thereof can be prepared using the characteristics based on the basic structure or the type of substituents thereof and by applying various known synthesis methods. During the preparation, replacement of the relevant functional group with a suitable protective group (a group that can be easily converted into the relevant functional group) at the stage from starting material to an intermediate may be effective depending on the type of the functional group in the production technology in some cases. The protective group for such a functional group may include, for example, the protective groups described in "Greene's Protective Groups in Organic Synthesis (4th edition, 2006)", P. G. M. Wuts and T. W. Greene, and one of these may be selected and used as necessary depending on the reaction conditions. In this kind of method, a desired compound can be obtained by introducing the protective group, by carrying out the reaction and by eliminating the protective group as necessary.

In addition, the prodrug of the compound of the formula (I) can be prepared by introducing a specific group at the stage from a starting material to an intermediate, or by carrying out the reaction using the obtained compound of the formula (I), as in the case of the above-mentioned protective group. The reaction can be carried out using methods known to those skilled in the art, such as ordinary esterification, amidation, dehydration, and the like.

Hereinbelow, the representative preparation methods for the compound of the formula (I) will be described. Each of the production processes may also be carried out with reference to the references appended in the present description. Further, the preparation methods of the present invention are not limited to the examples as shown below.

(Production Process 1)

[Chem. 7]

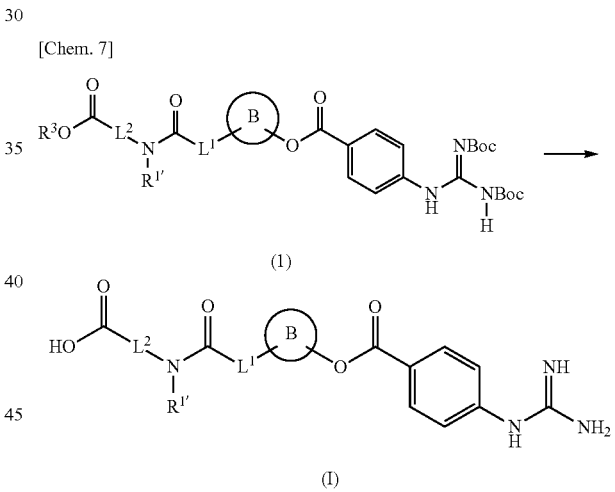

(in which $R^3$ represents H or tert-butyl, Boc represents tert-butoxycarbonyl, and $R^{1'}$ represents a group described in $R^1$ and a group having —$CO_2$-tert-butyl as a substituent).

The present production process is a method for preparing a compound (I) which is the compound of the present invention by deprotecting Compound 1.

The present step is carried out by using Compound 1 and a deprotecting reagent in equivalent amounts, or either thereof in an excess amount, and stirring the mixture in a solvent which is inert to the reaction or in the absence of a solvent, in a range of from cooling to heating and refluxing, usually for 0.1 hours to 5 days. Examples of the solvent used herein are not particularly limited, but include ethers such as diethylether, tetrahydrofuran (THF), 1,4-dioxane, and dimethoxyethane, and halogenated hydrocarbons such as dichloromethane, 1,2-dichloroethane, chloroform, and the like. Examples of the deprotecting reagent are not particularly limited, but include a solution of hydrogen chloride in 1,4-dioxane, a solution of hydrogen chloride in ethyl acetate, trifluoroacetic acid, and the like.

In addition, in the case where a —CO$_2$-tert-butyl group is present as a substituent in R$^{1'}$, the tert-butyl group is deprotected at the same time in the present step.

(Preparation of Starting Compound)

The starting compound in the preparation method above can be prepared by using, for example, the method below, the method described in Preparation Examples as described later, a known method, or a modified method thereof.

(Starting Material Synthesis 1)

[Chem. 8]

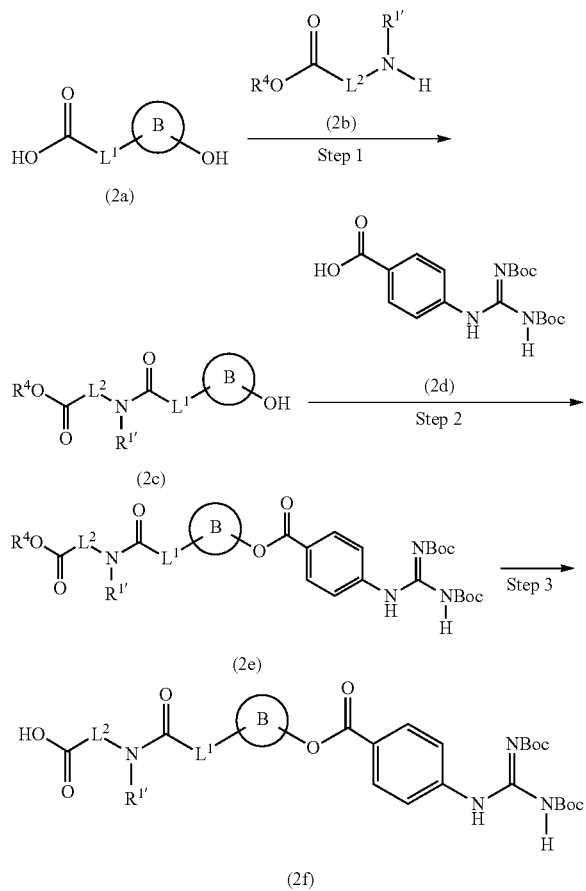

(in which R$^4$ represents a tert-butyl group or a benzyl group).

The present production process is a method for preparing Compound 2e or 2f which is Starting Compound 1 of the production process 1.

(Step 1)

The present step is a step of obtaining Compound 2c by subjecting Compound 2a and Compound 2b to amidation.

The present step is carried out by using Compound 2a and Compound 2b in equivalent amounts, or either thereof in an excess amount, and stirring the mixture in a solvent which is inert to the reaction, in a range of from cooling to heating and refluxing, and preferably from −20° C. to 60° C., usually for 0.1 hours to 5 days, in the presence of a condensing agent. Examples of the solvent used herein are not particularly limited, but include aromatic hydrocarbons such as benzene, toluene, and xylene, halogenated hydrocarbons such as dichloromethane, 1,2-dichloroethane, and chloroform, ethers such as diethyl ether, tetrahydrofuran, 1,4-dioxane, and dimethoxyethane, N,N-dimethyl formamide (DMF), dimethyl sulfoxide (DMSO), ethyl acetate, acetonitrile, water, and a mixture thereof. Examples of the condensing agent include, but are not limited to, N-[3-(dimethylamino)propyl]-N'-ethylcarbodiimide hydrochloride, dicyclohexylcarbodiimide, 1,1'-carbonylbis-1H-imidazole, diphenylphosphoryl azide, phosphorus oxychloride, O-(7-azabenzotriazol-1-yl)-N,N,N',N'-tetramethyluronium hexafluorophosphate (HATU), (1-cyano-2-ethoxy-2-oxoethylidenaminoxy)dimethylamino-morpholino-carbenium hexafluorophosphate (COMU), and the like. It is preferable in some cases for the progress of the reaction to use an additive such as 1H-benzotriazol-1-ol. In addition, it is preferable in some cases for the smooth progress of the reaction to use organic bases such as triethylamine, N,N-diisopropylethylamine, N-methylmorpholine, dimethylaminopyridine, and pyridine, or inorganic bases such as potassium carbonate, sodium carbonate, and potassium hydroxide.

Further, Compounds 2a and 2b are commercially available, and can be prepared by a known method (for example, Journal of Medicinal Chemistry, 2003, Vol. 46, No. 12, pp. 2446-2455; WO02006/083781; or the like) or a method equivalent thereto, or the method described in Preparation Examples as described later.

(Step 2)

The present step is a step of obtaining Compound 2e by subjecting Compound 2c and Compound 2d to esterification.

In the present step, a method equivalent to Step 1 of Starting Material Synthesis 1 can be used.

Further, Compound 2d can be prepared by a known method (for example, Tetrahedron Letters, 1993, Vol. 34, No. 21, pp. 3389-3392) or a method equivalent thereto.

(Step 3)

The present step is a step of obtaining Compound 2f having a benzyl group deprotected, in the case where R$^4$ in Compound 2e is the benzyl group.

In the present step, Compound 2e is stirred in a solvent which is inert to the reaction, in a hydrogen atmosphere, in the presence of a metal catalyst, usually for 1 hour to 5 days. This reaction is usually carried out in a range of from cooling to heating, and preferably at room temperature. Examples of the solvent used herein are not particularly limited, but include alcohols such as methanol, ethanol, and 2-propanol, ethers such as diethylether, tetrahydrofuran, 1,4-dioxane, and dimethoxyethane, water, ethyl acetate, N,N-dimethylformamide, dimethyl sulfoxide, and a mixture thereof. As the metal catalyst, palladium catalysts such as palladium carbon, palladium black, and palladium hydroxide, platinum catalysts such as platinum oxide, nickel catalysts such as reduced nickel and Raney nickel, or rhodium catalysts such as tris(triphenylphosphine)chlororhodium are suitably used. It is also possible to use formic acid or ammonium formate as a hydrogen source in an equivalent amount or an excess amount with respect to that of the compound 2e.

DOCUMENTS

M. Hudlicky, "Reductions in Organic Chemistry, 2$^{nd}$ edition (ACS Monograph: 188)", ACS, 1996

"Jikken Kagaku Koza (Courses in Experimental Chemistry) (5$^{th}$ edition)", edited by The Chemical Society of Japan, Vol. 19 (2005) (Maruzen)

The compounds of the formula (I) can be isolated and purified as their free compounds, salts, hydrates, solvates, or polymorphic crystalline substances thereof. The salts of the compound of the formula (I) can be prepared by carrying out the treatment of a conventional salt forming reaction.

Isolation and purification are carried out by employing ordinary chemical operations such as extraction, fractional crystallization, various types of fractional chromatography, and the like.

Various isomers can be prepared by selecting an appropriate starting compound or separated by using the difference in the physicochemical properties between the isomers. For example, the optical isomers can be obtained by means of a general method for designing optical resolution of racemic products (for example, fractional crystallization for inducing diastereomer salts with optically active bases or acids, chromatography using a chiral column or the like, and others), and further, the isomers can also be prepared from an appropriate optically active starting compound.

The pharmacological activity of the compound of the formula (I) was confirmed by the tests shown below.

1. Confirmation of Trypsin Inhibitory Activity in Humans and Mice

In the experiment, human recombinant trypsin (rh-trypsin; manufactured by Wako Pure Chemical Industries, Ltd.), cat. #206-17171) and mouse trypsin (m-trypsin; purified from the mouse small intestine contents by the present inventors) were used. The method for purifying m-trypsin from the contents of the mouse small intestine is shown below.

The small intestine contents and the gastrointestinal tract obtained from 10 mice were homogenized in phosphate buffer saline (PBS) using Polytron, and subjected to centrifugation several times at 15,000×g for 10 minutes. The supernatant was mixed at 4° C. for 16 hours with a Benzamidine Sepharose 4 Fast Flow Resin (GE Healthcare: #17-5123-10). After washing the resin with PBS, m-trypsin was eluted with a glycine buffer (pH 3.0) to carry out purification. It was confirmed by Western blot analysis that the obtained purified fraction was recognized as an Anti-mouse Trypsin Antibody (Santa Cruz Biotechnology, Inc.: sc-67388). The method for measuring the trypsin inhibiting activity is shown below.

The compound was dissolved in dimethyl sulfoxide (DMSO), and diluted to an arbitrary concentration (A). A was 100-fold diluted with a buffer (0.1 M Tris (pH 8.0), 0.15 M NaCl, 10 mM $CaCl_2$, 0.05% Brij35) (B). The rh-trypsin was diluted with a buffer to 0.088 μg/mL, and for the m-trypsin, the purified fraction liquid was 50-fold diluted with the buffer (C). The dilution ratio of the m-trypsin was set to exhibit the same activity as the 0.088 μg/mL of rh-trypsin as determined by kinetic analysis. A BZiPAR solution (Rhodamine Reference Substrate) which is substrate for the trypsin enzyme was diluted with the buffer to 5 mol/L (D). 5 μL of B, 5 μL of C, and 10 μL of D were added to a 384-well plate, and incubated at room temperature for 30 minutes. Fluorescent signals were detected at a maximum excitement (Ex)/fluorescent wavelength (Em)=497 nm/520 nm using a Tecan Safire Fluorometer. The compound was studied at 2500 nM, 750 nM, 250 nM, 75 nM, 25 nM, 7.5 nM, 2.5 nM, 0.75 nM, 0.25 nM, 0.075 nM, 0.025 nM, and 0.0075 nM, and the inhibitory rate of each compound was calculated by assuming the inhibition without addition of the compound (DMSO alone) in the presence of an enzyme as 0% inhibition, and assuming the inhibition without addition of the compound in the absence of an enzyme as 100% inhibition. Based on the obtained inhibitory rates, the trypsin inhibitory activities ($IC_{50}$ values, nM) were calculated from the non-linear regression.

The results of the test are shown in Table 1. Ex in the tables represents the Example No. as denoted below (which shall apply hereinafter).

TABLE 1

| Ex | r-h Trypsin | Mouse trypsin |
|---|---|---|
| 1 | 0.31 | 0.41 |
| 2 | 0.4 | 0.51 |
| 3 | 0.21 | 0.22 |
| 4 | 0.43 | 0.61 |
| 5 | 0.19 | 0.27 |
| 6 | 0.29 | 0.20 |
| 7 | 0.30 | 0.26 |
| 8 | 0.43 | 0.57 |
| 10 | 1.2 | 1.4 |
| 11 | 0.31 | 0.68 |
| 12 | 1.5 | 1.7 |
| 13 | 0.25 | 0.36 |
| 14 | 0.23 | 0.26 |
| 15 | 0.10 | 0.18 |
| 16 | 0.14 | 0.24 |
| 17 | 0.22 | 0.27 |
| 18 | 0.29 | 0.48 |
| 19 | 0.39 | 0.60 |
| 20 | 0.47 | 0.77 |
| 21 | 0.38 | 0.52 |
| 22 | 0.34 | 0.44 |
| 23 | 0.46 | 0.46 |
| 24 | 0.23 | 0.24 |
| 25 | 0.28 | 0.35 |
| 26 | 0.33 | 0.34 |
| 27 | 0.32 | 0.35 |
| 28 | 0.38 | 0.40 |
| 29 | 0.26 | 0.23 |
| 30 | 0.25 | 0.28 |
| 31 | 0.23 | 0.22 |
| 32 | 0.15 | 0.14 |
| 33 | 0.18 | 0.16 |
| 34 | 0.21 | 0.17 |
| 35 | 0.37 | 0.42 |
| 36 | 0.26 | 0.28 |
| 37 | 0.24 | 0.18 |
| 38 | 0.26 | 0.23 |
| 39 | 0.18 | 0.13 |
| 40 | 0.29 | 0.27 |
| 41 | 0.26 | 0.22 |
| 42 | 0.20 | 0.14 |
| 43 | 0.17 | 0.19 |
| 44 | 0.20 | 0.20 |
| 45 | 0.36 | 0.54 |
| 46 | 0.25 | 0.23 |
| 47 | 0.26 | 0.29 |
| 48 | 0.36 | 0.44 |
| 49 | 0.37 | 0.45 |
| 50 | 0.28 | 0.43 |
| 51 | 0.34 | 0.38 |
| 52 | 0.43 | 0.55 |
| 53 | 0.54 | 0.60 |
| 54 | 0.29 | 0.46 |
| 55 | 0.35 | 0.47 |
| 56 | 0.35 | 0.59 |
| 57 | 0.19 | 0.38 |
| 58 | 0.68 | 0.74 |
| 59 | 0.71 | 0.87 |
| 60 | 0.33 | 0.31 |

The compound of the present invention exhibited a good trypsin inhibitory activity.

2. Test of Increase in Fecal Protein Concentration Using Mice

For the experiment, 6-week old male ICR mice were used. The experiment was carried out in five mice per group. After fasting the mice for 15 hours, the control group was forcibly orally administered with a 0.5% methyl cellulose (MC) solution, and the test drug group was forcibly orally administered (5 mg/kg) with a solution or suspension obtained by dissolving or suspending the compound in the 0.5% MC solution. The fasting was stopped immediately thereafter, free feeding (CE-2) was started, and then the feces were collected from after 3 hours to after 9 hours, and weighed. All of the obtained feces were suspended in 6 mL of distilled water, and centrifuged at 1,940×g for 10 minutes. The protein concentration in the obtained supernatant was measured by a Bradford method, and the amount of the protein in 1 g of feces was calculated by dividing the protein concentration in the feces by the total weight of feces. Further, the efficacy was investigated from the ratio to the control group. For the compounds that were evaluated multiple times, the average values were calculated.

The results of the activities with an increase in Fecal Protein, assuming a value for the control group as 1, are shown in Table 2.

TABLE 2

| Ex | Folds (vs. control) |
| --- | --- |
| 1 | 2.00 |
| 2 | 2.55 |
| 3 | 2.09 |
| 4 | 2.62 |
| 5 | 1.88 |
| 6 | 1.84 |
| 7 | 1.83 |
| 8 | 1.90 |
| 11 | 2.63 |
| 13 | 2.73 |
| 14 | 1.79 |
| 15 | 2.61 |
| 16 | 2.39 |
| 17 | 2.7 |
| 18 | 2.18 |
| 19 | 2.51 |
| 20 | 2.23 |
| 21 | 2.51 |
| 22 | 2.15 |
| 23 | 2.53 |
| 24 | 1.51 |
| 25 | 1.35 |
| 26 | 1.70 |
| 27 | 1.98 |
| 28 | 1.54 |
| 29 | 1.43 |
| 30 | 1.68 |
| 31 | 1.51 |
| 32 | 1.90 |
| 33 | 1.39 |
| 34 | 2.07 |
| 35 | 1.59 |
| 36 | 1.90 |
| 37 | 1.74 |
| 38 | 1.91 |
| 39 | 1.08 |
| 40 | 1.89 |
| 41 | 2.01 |
| 42 | 2.04 |
| 43 | 1.98 |
| 44 | 1.72 |
| 45 | 1.38 |
| 46 | 1.84 |
| 47 | 1.91 |
| 48 | 1.79 |
| 49 | 2.07 |
| 50 | 1.56 |
| 51 | 1.66 |
| 52 | 1.78 |
| 53 | 1.64 |
| 54 | 1.70 |
| 55 | 2.30 |
| 56 | 1.45 |

TABLE 2-continued

| Ex | Folds (vs. control) |
| --- | --- |
| 57 | 2.25 |
| 58 | 2.18 |
| 59 | 1.64 |
| 60 | 2.26 |

The compounds shown in the table above exhibited an increased amount of protein in the diet to be discharged as undigested by the trypsin activity inhibitory action, and thus, an inhibited protein uptake in the biological body.

3. Test of Rat Uninephrectomy Doxorubicin (DXR)-Induced Nephropathy Model (Renal Function Reduced Model)

Uninephrectomy was performed in the left kidney of 10-week old male Wistar rats, and one week later, DXR (5 mg/kg) was administered to the rats via the caudal vein to induce a nephropathy model. The experiment was carried out in ten rats per group. During the period of administering the compound, the rats were fed with diet only in daytime, while fasted in nighttime. A test compound (10 mg/kg) was suspended in a 0.5% methylcellulose (MC) solution from the day after the preparation of the model, and was forcibly orally administered twice (morning and night) daily. To each of a sham (normal) group and a control group, 0.5% MC was forcibly orally administered. At 1, 2, and 3 weeks after the start of administration of the test compound, 24-hour urine collection was each performed to measure the amount of the protein excretion in urine. Blood collection was performed after the end of the urine collection at week 3, and the concentration of creatinine in plasma was measured.

As a result of the test above, for example, the compound of Example 2 significantly lowered the amount of protein excretion in urine, as compared with the control group, and the inhibitory rate at week 3 was about 42%. Further, the present compound significantly lowered the creatinine concentration in plasma and the inhibitory rate at week 3 was about 42%.

From the results of the present test, it was confirmed that the compounds exhibited the lowering effects of the protein excretion in urine and the creatinine concentration in plasma, and thus, the progression of the nephropathy was inhibited.

From the test above, a good inhibitory activity of trypsin and an inhibitory effects for protein absorption based on the inhibition of proteolytic enzymes were confirmed. Further, it was confirmed that, for example, the compound of Example 2 had lowering effect of the amount of protein excretion and the creatinine concentration in plasma in a model with nephropathy showing reduced renal function. Therefore, the compound of Formula (I) can be used as an agent for preventing and/or treating trypsin-related diseases (for example, chronic pancreatitis, gastroesophageal reflux disease, hepatic encephalopathy, influenza, and the like), and kidney diseases (for example, chronic kidney disease, acute glomerulonephritis, acute kidney injury, and the like), which will act as an agent which will substitute low protein diet.

A pharmaceutical composition containing one or two or more kinds of the compound of the formula (I) or a salt thereof as an active ingredient can be prepared using excipients that are usually used in the art, that is, excipients for pharmaceutical preparations, carriers for pharmaceutical preparations, and the like according to the methods usually used.

Administration can be accomplished either by oral administration via tablets, pills, capsules, granules, powders, solutions, and the like, or parenteral administration, such as injections such as intraarticular, intravenous, and intramuscular injections, suppositories, ophthalmic solutions, eye ointments, transdermal liquid preparations, ointments, transdermal patches, transmucosal liquid preparations, transmucosal patches, inhalers, and the like.

The solid composition for use in the oral administration is used in the form of tablets, powders, granules, or the like. In such a solid composition, one or more active ingredient(s) are mixed with at least one inactive excipient. In a conventional method, the composition may contain inactive additives, such as a lubricant, a disintegrating agent, a stabilizer, or a solubilization assisting agent. If necessary, tablets or pills may be coated with sugar or a film of a gastric or enteric coating substance.

The liquid composition for oral administration contains pharmaceutically acceptable emulsions, solutions, suspensions, syrups, elixirs, or the like, and also contains generally used inert diluents, for example, purified water or ethanol. In addition to the inert diluent, the liquid composition may also contain auxiliary agents, such as a solubilization assisting agent, a moistening agent, and a suspending agent, sweeteners, flavors, aromatics, or antiseptics.

The injections for parenteral administration include sterile aqueous or non-aqueous solutions, suspensions and emulsions. The aqueous solvent includes, for example, distilled water for injection and physiological saline. Examples of the non-aqueous solvent include alcohols such as ethanol. Such a composition may further contain a tonicity agent, an antiseptic, a moistening agent, an emulsifying agent, a dispersing agent, a stabilizer, or a solubilizing assisting agent. These are sterilized, for example, by filtration through a bacteria retaining filter, by a bactericide being blended in, or irradiation. In addition, these can also be used by preparing a sterile solid composition, and dissolving or suspending in sterile water or a sterile solvent for injection prior to its use.

The agent for external use includes ointments, plasters, creams, jellies, poultices, sprays, lotions, eye drops, eye ointments, and the like. The agents contain generally used ointment bases, lotion bases, aqueous or non-aqueous liquid preparations, suspensions, emulsions, and the like.

As the transmucosal agents such as an inhaler, a transnasal agent, and the like, those in the form of a solid, liquid, or semi-solid state are used, and can be prepared in accordance with a conventionally known method. For example, a known excipient, and also a pH adjusting agent, an antiseptic, a surfactant, a lubricant, a stabilizer, a thickening agent, or the like may be appropriately added thereto. For their administration, an appropriate device for inhalation or blowing can be used. For example, a compound may be administered alone or as a powder of formulated mixture, or as a solution or suspension in combination with a pharmaceutically acceptable carrier, using a known device or sprayer, such as a measured administration inhalation device, and the like. A dry powder inhaler or the like may be for single or multiple administration use, and a dry powder or a powder-containing capsule may be used. Alternatively, this may be in a form such as a pressurized aerosol spray which uses an appropriate ejection agent, for example, a suitable gas such as chlorofluoroalkane, carbon dioxide, and the like.

In oral administration, the daily dose is appropriately from about 0.001 to 100 mg/kg, preferably from 0.1 to 30 mg/kg, and more preferably 0.1 to 10 mg/kg, per body weight, administered in one portion or in 2 to 4 separate portions. In the case of intravenous administration, the daily dose is suitably administered from about 0.0001 to 10 mg/kg per body weight, once a day or two or more times a day. In addition, a transmucosal agent is administered at a dose from about 0.001 to 100 mg/kg per body weight, once a day or two or more times a day. The dose is appropriately decided in response to the individual case by taking the symptoms, the age, and the gender, and the like into consideration.

Although varying depending on administration routes, dosage forms, administration sites, or the types of excipients and additives, the pharmaceutical composition of the present invention contains 0.01 to 100% by weight, and in a certain embodiment, 0.01 to 50% by weight of one or more kinds of the compound of the formula (I) or a salt thereof, which is an active ingredient.

The compound of the formula (I) or a salt thereof can be used in combination with various agents for treating or preventing the diseases for which the compound of the formula (I) or a salt thereof is considered to be effective, as described above. The combined preparation may be administered simultaneously, or separately and continuously, or at a desired time interval. The preparations to be administered simultaneously may be a blend, or may be prepared individually.

EXAMPLES

Hereinbelow, the preparation methods for the compound of the formula (I) or a salt thereof will be described in more detail with reference to Examples, but the present invention is not limited to the compounds described in the Examples as described below. Furthermore, the production processes for the starting compounds will be described in Preparation Examples. Further, the preparation methods for the compound of the formula (I) are not limited to the preparation methods of the specific Examples as below, but the compound of the formula (I) can be prepared by any combination of the preparation methods or the methods that are apparent to a person skilled in the art.

Furthermore, the following abbreviations may be used in some cases in the Examples, Preparation Examples, and Tables below.

PEx: Preparation Example No. (the compounds in which "*" is marked in the chemical and structural formulae denote that the compounds are single isomers having steric configurations of the denoted structures; the compounds in which "**" is marked in the chemical and structural formulae denote that the compounds are single isomers, but have no steric configuration determined; and the compounds in which "#" is marked in the chemical and structural formulae denote a diastereomeric mixture), Ex: Example No. (the compounds in which "*" is marked in the chemical and structural formulae denote that the compounds are single isomers having steric configurations of the denoted structures; the compounds in which "**" is marked in the chemical and structural formulae denote that the compounds are single isomers, but have no steric configuration determined; and the compounds in which "#" is marked in the chemical and structural formulae denote a diastereomeric mixture), PSyn: Preparation Example No. prepared by the same method, Syn: Example No. prepared by the same method, Str: Chemical Structural formula (Me: methyl, $^t$Bu: tert-butyl, Ph: phenyl, Boc: tert-butoxycarbonyl, Bn: benzyl, OMe: —O— methyl, OBn: —O-benzyl, O$^t$Bu: —O-tert-butyl, and NBoc: —N-tert-butoxycarbonyl), Data: Physicochemical Data, ESI+: m/z values in mass spectroscopy (Ionization ESI, representing (M+H)$^+$ unless otherwise specified), ESI−: m/z values (Ionization ESI, representing (M−H)⁻ unless otherwise specified), APCI+: m/z values (atmospheric pressure chemical ionization APCI, representing (M+H)⁺ unless otherwise specified), APCI/ESI+: APCI/ESI−MS[M+H]⁺ (APCI/ESI means the simultaneous measurement of APCI and ESI), NMR1: characteristic δ (ppm) in ¹H NMR in dimethylsulfoxide-d₆, NMR2: characteristic δ (ppm) in ¹H NMR in CDCl₃, "M" in Preparation Examples and Examples: mol/L, and RT: a retention time in supercritical chromatography or liquid chromatography, in a unit of minutes (min).

In addition, in the structural formulae, HCl represents hydrochloride, and TFA represents trifluoroacetate.

Preparation Example 1

A mixture of tert-butyl 4-methylthiophene-2-carboxylate (12.0 g), N-bromosuccinimide (10.8 g), 2,2′-azobis(isobutyronitrile) (496 mg), and carbon tetrachloride (119 mL) was stirred at 90° C. for 1 hour. Further, N-bromosuccinimide (1.08 g) was added thereto, and the mixture was stirred at 90° C. for 1 hour. The reaction suspension was cooled to room temperature, then the insoluble material was separated by filtration, and the filtrate was concentrated under reduced pressure. The residue was purified by silica gel column chromatography (hexane-ethyl acetate) to obtain tert-butyl 4-(bromomethyl)thiophene-2-carboxylate (16.3 g).

To a solution of tert-butyl 4-(bromomethyl)thiophene-2-carboxylate (9.90 g) in N,N-dimethylformamide (100 mL) were added tert-butyl glycinate hydrochloride (18.0 g) and triethylamine (19.9 mL), followed by stirring at 60° C. for 15 hours. The reaction suspension was cooled to room temperature, and then sodium triacetoxyborohydride (22.7 g) was added thereto, followed by stirring at room temperature for 5 hours. To the reaction suspension were added water and an aqueous sodium hydrogen carbonate solution, followed by extraction with ethyl acetate. The organic layer was washed with a 5% aqueous sodium chloride solution, then dried over anhydrous sodium sulfate, and concentrated under reduced pressure. The residue was purified by silica gel column chromatography (hexane-ethyl acetate) to obtain tert-butyl 4-{[(2-tert-butoxy-2-oxoethyl)amino]methyl}thiophene-2-carboxylate (5.67 g).

Preparation Example 2

To a solution of 6-hydroxy-2-naphthoic acid (220 mg) in N,N-dimethylformamide (3.30 mL) were added tert-butyl 4-{[(2-tert-butoxy-2-oxoethyl)amino]methyl}thiophene-2-carboxylate (383 mg), O-(7-azabenzotriazol-1-yl)-N,N,N′,N′-tetramethyluronium hexafluorophosphate (489 mg), and N,N-diisopropylethylamine (500 μL), followed by stirring at room temperature for 20 hours. Further, O-(7-azabenzotriazol-1-yl)-N,N,N′,N′-tetramethyluronium hexafluorophosphate (222 mg) and N,N-diisopropylethylamine (200 μL) were added thereto, followed by stirring at room temperature for 6 hours. To the reaction solution was added water, followed by extraction with ethyl acetate. The organic layer was washed with water and a saturated aqueous sodium chloride solution in this order, then dried over anhydrous magnesium sulfate, and concentrated under reduced pressure. The residue was purified by silica gel column chromatography (hexane-ethyl acetate) to obtain tert-butyl 4-{[(2-tert-butoxy-2-oxoethyl)(6-hydroxy-2-naphthoyl)amino]methyl}thiophene-2-carboxylate (277 mg).

Preparation Example 3

To a solution of 4-[N′,N″-bis(tert-butoxycarbonyl)carbamimidamide]benzoic acid (194 mg) in dichloromethane (7.29 mL) were added N-[3-(dimethylamino)propyl]-N′-ethylcarbodiimide hydrochloride (118 mg), tert-butyl 4-{[(2-tert-butoxy-2-oxoethyl)(6-hydroxy-2-naphthoyl)amino]methyl}thiophene-2-carboxylate (255 mg), and 4-dimethylaminopyridine (18.8 mg), followed by stirring at room temperature for 24 hours. To the reaction liquid was added water, followed by extraction with chloroform. The organic layer was dried over anhydrous magnesium sulfate and concentrated under reduced pressure. The residue was purified by silica gel column chromatography (hexane-ethyl acetate) to obtain tert-butyl 4-({[6-({4-[N′,N″-bis(tert-butoxycarbonyl)carbamimidamide]benzoyl}oxy)-2-naphthoyl](2-tert-butoxy-2-oxoethyl)amino}methyl)thiophene-2-carboxylate (137 mg).

Preparation Example 4

To a solution of 6-methoxy-1-benzothiophene-2-carboxylic acid (960 mg) in dichloromethane (5.76 mL) was added dropwise a 1 M solution (37.5 mL) of boron tribromide in dichloromethane over 10 minutes under ice-cooling, followed by stirring at room temperature for 3 hours. The reaction liquid was added dropwise to ice, followed by stirring. The precipitate was collected by filtration, and dried under reduced pressure to obtain 6-hydroxy-1-benzothiophene-2-carboxylic acid (920 mg).

Preparation Example 5

To a solution of 2-tert-butyl 3,7-dimethyl (3R)-3,4-dihydroisoquinoline-2,3,7(1H)-tricarboxylate (345 mg) in methanol (7.00 mL) was added a 1 M aqueous sodium hydroxide solution (3.50 mL), followed by stirring at room temperature for 3 hours. The mixture was neutralized by the addition of 1 M hydrochloric acid (3.50 mL), and then water was added thereto, followed by extraction with ethyl acetate. The organic layer was dried over anhydrous sodium sulfate and concentrated under reduced pressure to obtain (3R)-2-(tert-butoxycarbonyl)-1,2,3,4-tetrahydroisoquinoline-3,7-dicarboxylic acid (328 mg).

Preparation Example 6

To a solution of (6-hydroxy-1,2,3,4-tetrahydronaphthalen-1-yl)acetic acid (1.03 g) in N,N-dimethylformamide (20.5 mL) were added tert-butyl 3-{[(2-tert-butoxy-2-oxoethyl)amino]methyl}benzoate hydrochloride (1.96 g), triethylamine (762 μL), N-[3-(dimethylamino)propyl]-N′-ethylcarbodiimide hydrochloride (1.00 g), and 1H-benzotriazol-1-ol (705 mg), followed by stirring at room temperature for 13 hours. To the reaction mixture was added water, followed by extraction with ethyl acetate. The organic layer was sequentially washed with water and a saturated aqueous sodium chloride solution, then dried over anhydrous sodium sulfate, and concentrated under reduced pressure. The residue was purified by silica gel column chromatography (hexane-ethyl acetate) to obtain tert-butyl 3-({(2-tert-butoxy-2-oxoethyl) [(6-hydroxy-1,2,3,4-tetrahydronaphthalen-1-yl)acetyl]amino}methyl)benzoate (2.41 g).

Preparation Example 7

Under a nitrogen atmosphere, to a solution of tert-butyl 3-(chloromethyl)benzoate (29.1 g) in N,N-dimethylformamide (300 mL) were added tert-butyl glycinate hydrochloride (43.0 g) and triethylamine (71.6 mL), followed by stirring at 60° C. to 63° C. for 3 hours. The reaction mixture was ice-cooled, and then water was added thereto, followed by extraction with ethyl acetate. The organic layer was sequentially washed with a 10% aqueous ammonium chloride solution and a 20% aqueous sodium chloride solution, then dried over anhydrous sodium sulfate, and concentrated under reduced pressure. The residue was dissolved in ethyl acetate (400 mL), and then a 4 M solution (32.1 mL) of hydrogen chloride in ethyl acetate was added dropwise thereto under ice-cooling in a nitrogen atmosphere, followed by stirring for 1 hour. The precipitate was collected by filtration, washed with ethyl acetate, and then dried at 50° C. under reduced pressure to obtain tert-butyl 3-{[(2-tert-butoxy-2-oxoethyl)amino]methyl}benzoate hydrochloride (28.5 g).

Preparation Example 8

A mixture of ethyl (6-methoxy-1,2,3,4-tetrahydronaphthalen-1-yl)acetate (2.08 g) and 48% hydrobromic acid (40.0 mL) was stirred at 120° C. for 17 hours. The reaction mixture was left to be cooled and then concentrated under reduced pressure. To the residue was added tetrahydrofuran (100 mL), followed by stirring at room temperature for 1 hour, and then the precipitate was collected by filtration. The filtrate was concentrated under reduced pressure, and then the residue was purified by silica gel column chromatography (hexane-ethyl acetate). To the purified product was added diisopropylether (15.0 mL), followed by stirring at room temperature for 1 hour. The precipitate was collected by filtration, washed with diisopropylether, and then dried at room temperature under reduced pressure to obtain (6-hydroxy-1,2,3,4-tetrahydronaphthalen-1-yl)acetic acid (1.06 g).

Preparation Example 9

To a solution of 4-[N',N''-bis(tert-butoxycarbonyl)carbamimidamide]benzoic acid (1.97 g) in dichloromethane (48.0 mL) were added tert-butyl 3-({(2-tert-butoxy-2-oxoethyl)[(6-hydroxy-1,2,3,4-tetrahydronaphthalen-1-yl)acetyl]amino}methyl)benzoate (2.40 g), N-[3-(dimethylamino)propyl]-N'-ethylcarbodiimide hydrochloride (1.17 g), and 4-dimethylaminopyridine (173 mg), followed by stirring at room temperature for 2 hours. Further, 4-[N',N''-bis(tert-butoxycarbonyl)carbamimidamide]benzoic acid (179 mg) and N-[3-(dimethylamino)propyl]-N'-ethylcarbodiimide hydrochloride (100 mg) were added thereto, followed by stirring at room temperature for 1 hour. The reaction mixture was concentrated under reduced pressure, and the residue was purified by silica gel column chromatography (hexane-ethyl acetate) to obtain tert-butyl 3-{[{[6-({4-[N',N''-bis(tert-butoxycarbonyl)carbamimidamide]benzoyl}oxy)-1,2,3,4-tetrahydronaphthalen-1-yl]acetyl}(2-tert-butoxy-2-oxoethyl)amino]methyl}benzoate (3.71 g).

Preparation Example 10

To a solution of tert-butyl N-[(benzyloxy)carbonyl]-4-(tert-butoxycarbonyl)-L-phenylalaninate (570 mg) in tetrahydrofuran (3.00 mL) and ethanol (3.00 mL) was added 10% palladium-carbon (138 mg, a 50% wet product) in an argon atmosphere, followed by stirring at room temperature overnight at normal pressure in a hydrogen atmosphere. The reaction suspension was filtered by passing it through a Celite (registered trademark) layer, and then the filtrate was concentrated under reduced pressure to obtain tert-butyl 4-(tert-butoxycarbonyl)-L-phenylalaninate (431 mg).

Preparation Example 11

A mixture of 3-[(benzyl {[6-(benzyloxy)-1,2,3,4-tetrahydronaphthalen-1-yl]acetyl}amino)methyl]pentanedioic acid (886 mg), N,N-dimethylformamide di-tert-butyl acetal (1.60 mL), and toluene (4.43 mL) was stirred at 80° C. for 4 hours. To the reaction mixture was added water, followed by extraction with ethyl acetate. The organic layer was washed with a saturated aqueous sodium chloride solution, then dried over anhydrous sodium sulfate, and concentrated under reduced pressure. The residue was purified by silica gel column chromatography (hexane-ethyl acetate) to obtain di-tert-butyl 3-[(benzyl {[6-(benzyloxy)-1,2,3,4-tetrahydronaphthalen-1-yl]acetyl}amino)methyl]pentanedioate (232 mg).

Preparation Example 12

To 3,7-dibenzyl 2-tert-butyl (3R)-3,4-dihydroisoquinoline-2,3,7(1H)-tricarboxylate (413 mg) was added a 4 M solution (4.00 mL) of hydrogen chloride in 1,4-dioxane, followed by stirring at room temperature overnight. The reaction suspension was concentrated under reduced pressure, and the residue was dried under reduced pressure to obtain dibenzyl (3R)-1,2,3,4-tetrahydroisoquinoline-3,7-dicarboxylate hydrochloride (358 mg).

Preparation Example 13

To a solution of 6-hydroxy-1-benzothiophene-3-carboxylic acid (100 mg), tert-butyl 4-{[(2-tert-butoxy-2-oxoethyl)amino]methyl}thiophene-2-carboxylate (186 mg), and N,N-diisopropylethylamine (88.2 μL) in N,N-dimethylformamide (3.00 mL) was added (1-cyano-2-ethoxy-2-oxoethylidenaminoxy)dimethylaminomorpholinocarbenium hexafluorophosphate (243 mg), followed by stirring at room temperature for 16 hours. The reaction mixture was diluted with ethyl acetate, and the organic layer was sequentially washed with water and a saturated aqueous sodium chloride solution, then dried over anhydrous sodium sulfate, and concentrated under reduced pressure. The residue was purified by silica gel column chromatography (hexane-ethyl acetate) to obtain tert-butyl 4-({(2-tert-butoxy-2-oxoethyl)[(6-hydroxy-1-benzothiophen-3-yl)carbonyl]amino}methyl)thiophene-2-carboxylate (230 mg).

Preparation Example 14

To a solution of tert-butyl [4-(aminomethyl)phenyl]acetate (1.00 g) in acetonitrile (15.0 mL) were added triethylamine (693 μL) and tert-butyl bromoacetate (668 μL), followed by stirring at room temperature for 4 hours. The reaction liquid was concentrated under reduced pressure, and then ethyl acetate was added thereto. The organic layer was sequentially washed with 0.1 M hydrochloric acid, an aqueous saturated sodium hydrogen carbonate solution, and a saturated aqueous sodium chloride solution, then dried over anhydrous magnesium sulfate, and concentrated under reduced pressure. The residue was purified by silica gel column chromatography (hexane-ethyl acetate) to obtain tert-butyl N-[4-(2-tert-butoxy-2-oxoethyl)benzyl]glycinate (747 mg).

Preparation Example 15

To a solution of 6-hydroxy-1-naphthoic acid (190 mg) in N,N-dimethylformamide (2.85 mL) were added tert-butyl 4-({[(2R)-1-tert-butoxy-1-oxopropan-2-yl]amino}methyl) thiophene-2-carboxylate (345 mg), O-(7-azabenzotriazol-1-yl)-N,N,N',N'-tetramethyluronium hexafluorophosphate (422 mg), and N,N-diisopropylethylamine (190 μL), followed by stirring at 50° C. for 19 hours. To the reaction solution was added water, followed by extraction with ethyl acetate. The organic layer was sequentially washed with water and a saturated aqueous sodium chloride solution, then dried over anhydrous magnesium sulfate, and concentrated under reduced pressure. The residue was purified by silica gel column chromatography (hexane-ethyl acetate) to obtain tert-butyl 4-({[(2R)-1-tert-butoxy-1-oxopropan-2-yl](6-hydroxy-1-naphthoyl)amino}methyl)thiophene-2-carboxylate (101 mg).

Preparation Example 16

To a solution of N-[(benzyloxy)carbonyl]-4-(tert-butoxycarbonyl)-L-phenylalanine (500 mg) in tetrahydrofuran (4.00 mL) and tert-butyl alcohol (4.00 mL) were added di-tert-butyl dicarbonate ester (656 mg) and 4-dimethylaminopyridine (30.6 mg), followed by stirring at room temperature overnight. To the reaction solution was added water, followed by extraction with ethyl acetate. The organic layer was sequentially washed with water, an aqueous saturated sodium hydrogen carbonate solution, and a saturated aqueous sodium chloride solution, then dried over anhydrous sodium sulfate, and concentrated under reduced pressure to obtain tert-butyl N-[(benzyloxy)carbonyl]-4-(tert-butoxycarbonyl)-L-phenylalaninate (641 mg).

Preparation Example 17

To a solution of (6-hydroxy-1,2,3,4-tetrahydronaphthalen-1-yl)acetic acid (150 mg), tert-butyl N-(2-tert-butoxy-2-oxoethyl)-L-phenylalaninate (293 mg), and N,N-diisopropylethylamine (147 μL) in N,N-dimethylformamide (4.50 mL) was added (1-cyano-2-ethoxy-2-oxoethylidenaminoxy) dimethylaminomorpholinocarbenium hexafluorophosphate (368 mg), followed by stirring at 60° C. for 8 hours. The reaction mixture was diluted with ethyl acetate, and the organic layer was sequentially washed with water and a saturated aqueous sodium chloride solution, then dried over anhydrous sodium sulfate, and concentrated under reduced pressure. The residue was purified by silica gel column chromatography (hexane-ethyl acetate) to obtain tert-butyl N-(2-tert-butoxy-2-oxoethyl)-N-[(6-hydroxy-1,2,3,4-tetrahydronaphthalen-1-yl)acetyl]-L-phenylalaninate (347 mg).

Preparation Example 18

To a solution of 5-methyl-1-benzothiophene-2-carboxylic acid (1.50 g) in N,N-dimethylformamide (10.5 mL) was added 1,1'-carbonylbis-1H-imidazole (1.27 g), followed by stirring at room temperature for 2 hours and 30 minutes. To the reaction mixture were added tert-butyl alcohol (1.44 mL) and 1,8-diazabicyclo[5.4.0]undeca-7-ene (1.17 mL), followed by stirring at 50° C. for 24 hours. The reaction mixture was diluted with ethyl acetate, and then the organic layer was sequentially washed with 0.1 M hydrochloric acid and a saturated aqueous sodium chloride solution, then dried over anhydrous magnesium sulfate, and concentrated under reduced pressure. The residue was purified by silica gel column chromatography (hexane-ethyl acetate) to obtain tert-butyl 5-methyl-1-benzothiophene-2-carboxylate (1.78 g).

Preparation Example 19

To a mixture of tert-butyl 5-methyl-1-benzothiophene-2-carboxylate (1.77 g), carbon tetrachloride (17.7 mL), and N-bromosuccinimide (2.16 g) was added 2,2'-azobis(isobutyronitrile) (58.5 mg), followed by stirring at 90° C. overnight. The reaction suspension was filtered and the filtrate was concentrated under reduced pressure. The residue was purified by silica gel column chromatography (hexane-ethyl acetate) to obtain tert-butyl 5-(bromomethyl)-1-benzothiophene-2-carboxylate (1.51 g).

Preparation Example 20

To a solution of tert-butyl 5-(bromomethyl)-1-benzothiophene-2-carboxylate (1.00 g) in N,N-dimethylformamide (10.0 mL) were added tert-butyl glycinate hydrochloride (1.02 g) and triethylamine (1.70 mL), followed by stirring at 85° C. to 95° C. overnight. The reaction mixture was cooled to room temperature, followed by extraction with ethyl acetate. The organic layer was washed with a 25% aqueous ammonium chloride solution, then dried over anhydrous magnesium sulfate, and concentrated under reduced pressure. The residue was purified by silica gel column chromatography (hexane-ethyl acetate) to obtain tert-butyl 5-{[(2-tert-butoxy-2-oxoethyl)amino]methyl}-1-benzothiophene-2-carboxylate (359 mg).

Preparation Example 21

To a solution of 2-tert-butyl 3-methyl (3R)-7-hydroxy-3,4-dihydroisoquinoline-2,3(1H)-dicarboxylate (1.00 g) in dichloromethane (20.0 mL) were added trifluoromethane sulfonic acid anhydride (770 μL) and 2,6-dimethyl pyridine (800 μL) under ice-cooling, followed by stirring for 2 hours under ice-cooling. To the reaction mixture was added water, followed by extraction with chloroform. The organic layer was dried over anhydrous sodium sulfate and concentrated under reduced pressure. To the residue were added N,N-dimethylformamide (15.0 mL), methanol (3.00 mL), palladium (II) acetate (37.0 mg), 1,1'-bis(diphenylphosphino)ferrocene (90.0 mg), and triethylamine (1.10 mL), followed by stirring at 80° C. overnight in a carbon monoxide atmosphere. The reaction mixture was cooled to room temperature and then concentrated under reduced pressure. To the residue was added water, followed by extraction with ethyl acetate. The organic layer was washed with a saturated aqueous sodium chloride solution, dried over anhydrous sodium sulfate, and then concentrated under reduced pressure. The residue was purified by silica gel column chromatography (hexane-ethyl acetate) to obtain 2-tert-butyl 3,7-dimethyl (3R)-3,4-dihydroisoquinoline-2,3,7(1H)-tricarboxylate (350 mg).

Preparation Example 22

To a solution of (3R)-2-(tert-butoxycarbonyl)-1,2,3,4-tetrahydroisoquinoline-3,7-dicarboxylic acid (320 mg) in N,N-dimethylformamide (6.00 mL) were added potassium carbonate (315 mg) and benzyl bromide (275 μL), followed by stirring at room temperature overnight. To the reaction suspension was added water, followed by extraction with ethyl acetate. The organic layer was sequentially washed with water and a saturated aqueous sodium chloride solution, then dried over anhydrous sodium sulfate, and concentrated under reduced pressure. The residue was purified by silica gel column chromatography (hexane-ethyl acetate) to obtain 3,7-dibenzyl 2-tert-butyl (3R)-3,4-dihydroisoquinoline-2,3,7(1H)-tricarboxylate (415 mg).

Preparation Example 23

To a solution of 2-bromo-1,3,5-trimethylbenzene (925 µL) in tetrahydrofuran (20.0 mL) was added dropwise a 1.59 M solution (3.86 mL) of n-butyllithium in hexane at −78° C., followed by stirring at −78° C. for 30 minutes. To the reaction mixture was added dropwise a solution of tert-butyl (4-bromo-2-thienyl)acetate (1.55 g) in tetrahydrofuran (15.0 mL), followed by stirring at −78° C. for 30 minutes. Subsequently, to the reaction mixture was added dropwise a 1.59 M solution (3.51 mL) of n-butyllithium in hexane, followed by stirring at −78° C. for 30 minutes. To the reaction mixture was added dropwise N,N-dimethylformamide (451 µL), followed by stirring at 78° C. for 1 hour. To the reaction liquid were added an aqueous ammonium chloride solution and ethyl acetate, thereby extracting the organic layer. The organic layer was dried over anhydrous magnesium sulfate and concentrated under reduced pressure. The residue was purified by silica gel column chromatography (hexane-ethyl acetate) to obtain tert-butyl (4-formyl-2-thienyl)acetate (355 mg).

Preparation Example 24

To a solution of tert-butyl (4-formyl-2-thienyl)acetate (350 mg), tert-butyl glycinate (243 mg), and acetic acid (265 µL) in dichloromethane (4.05 mL) was added sodium triacetoxyborohydride (656 mg) under ice-cooling, followed by stirring at room temperature for 3 hours. The reaction mixture was neutralized by the addition of an aqueous saturated sodium hydrogen carbonate solution, and then extracted with chloroform. The organic layer was dried over anhydrous magnesium sulfate and concentrated under reduced pressure. The residue was purified by silica gel column chromatography (hexane-ethyl acetate) to obtain tert-butyl N-{[5-(2-tert-butoxy-2-oxoethyl)-3-thienyl]methyl}glycinate (237 mg).

Preparation Example 25

A mixture of tert-butyl [3-(aminomethyl)phenyl]acetate (1.00 g), tert-butyl bromoacetate (700 µL), potassium carbonate (650 mg), and acetonitrile (20.0 mL) was stirred at room temperature overnight. To the reaction mixture was added water, followed by extraction with ethyl acetate. The organic layer was dried over anhydrous magnesium sulfate and concentrated under reduced pressure. The residue was purified by silica gel column chromatography (hexane-ethyl acetate) to obtain tert-butyl N-[3-(2-tert-butoxy-2-oxoethyl)benzyl]glycinate (1.14 g).

Preparation Example 26

To a mixture of N-benzyl-N-(cyclopenta-3-en-1-ylmethyl)-2-(6-hydroxy-1,2,3,4-tetrahydronaphthalen-1-yl)acetamide (430 mg), potassium carbonate (174 mg), and N,N-dimethylformamide (4.30 mL) was added benzyl bromide (177 µL), followed by stirring at 50° C. for 6 hours. The reaction mixture was cooled, and water was added thereto, followed by extraction with ethyl acetate. The organic layer was washed with a saturated aqueous sodium chloride solution, then dried over anhydrous sodium sulfate, and concentrated under reduced pressure. The residue was purified by silica gel column chromatography (hexane-ethyl acetate) to obtain N-benzyl-2-[6-(benzyloxy)-1,2,3,4-tetrahydronaphthalen-1-yl]-N-(cyclopenta-3-en-1-ylmethyl)acetamide (416 mg).

Preparation Example 27

To a mixture of N-benzyl-2-[6-(benzyloxy)-1,2,3,4-tetrahydronaphthalen-1-yl]-N-(cyclopenta-3-en-1-ylmethyl)acetamide (100 mg), tert-butyl alcohol (2.40 mL), and water (600 µL) were added a 2.5% solution (269 µL) of osmium tetraoxide in tert-butyl alcohol, and 4-methylmorpholine 4-oxide (75.5 mg), followed by stirring at room temperature for 2 hours. To the reaction mixture was added an aqueous sodium thiosulfate solution, followed by extraction with ethyl acetate. The organic layer was washed with a saturated aqueous sodium chloride solution, then dried over anhydrous sodium sulfate, and concentrated under reduced pressure to obtain N-benzyl-2-[6-(benzyloxy)-1,2,3,4-tetrahydronaphthalen-1-yl]-N-[(3,4-dihydroxycyclopentyl)methyl]acetamide (107 mg).

Preparation Example 28

To a mixture of N-benzyl-2-[6-(benzyloxy)-1,2,3,4-tetrahydronaphthalen-1-yl]-N-[(3,4-dihydroxycyclopentyl)methyl]acetamide (106 mg), iodobenzene diacetate (322 mg), dichloromethane (3.00 mL), and water (1.00 mL) was added 1-methyl-2-azaadamantan-N-oxyl (3.33 mg), followed by stirring at room temperature for 3 hours. To the reaction mixture was added a 20% aqueous sodium thiosulfate solution, followed by stirring at room temperature for 5 minutes. Subsequently, 1 M hydrochloric acid was added thereto, followed by extraction with ethyl acetate. The organic layer was dried over anhydrous sodium sulfate and concentrated under reduced pressure to obtain 3-[(benzyl{[6-(benzyloxy)-1,2,3,4-tetrahydronaphthalen-1-yl]acetyl}amino)methyl]pentanedioic acid (110 mg).

Preparation Example 29

To a mixture of a (1S)-1-phenylethanamine salt (370 mg) of [(1R)-6-methoxy-1,2,3,4-tetrahydronaphthalen-1-yl]acetic acid or an enantiomer thereof, and ethyl acetate (4.50 mL) was added 3 M hydrochloric acid (4.50 mL), followed by stirring at room temperature for 2 hours. The reaction mixture was extracted with ethyl acetate. The organic layer was dried over anhydrous sodium sulfate and then concentrated under reduced pressure to obtain [(1R)-6-methoxy-1,2,3,4-tetrahydronaphthalen-1-yl]acetic acid or an enantiomer thereof (243 mg).

Preparation Example 30

To a mixture of a (1R)-1-phenylethanamine salt (450 mg) of [(1R)-6-methoxy-1,2,3,4-tetrahydronaphthalen-1-yl]acetic acid or an enantiomer thereof, and ethyl acetate (5.51 mL) was added a 4 M solution (4.13 mL) of hydrogen chloride in ethyl acetate, followed by stirring at room temperature for 2 hours. To the reaction mixture was added water, followed by extraction with ethyl acetate. The organic layer was washed with a saturated aqueous sodium chloride solution, then dried over anhydrous sodium sulfate, and concentrated under reduced pressure to obtain [(1R)-6- methoxy-1,2,3,4-tetrahydronaphthalen-1-yl]acetic acid or an enantiomer thereof (290 mg).

Preparation Example 31

To a solution of [(1R)-6-methoxy-1,2,3,4-tetrahydronaphthalen-1-yl]acetic acid or an enantiomer thereof (238 mg) obtained in Preparation Example 29 in dichloromethane (8.00 mL) was added a 1 M solution (2.20 mL) of boron tribromide in dichloromethane under ice-cooling, followed by stirring at room temperature for 2 hours. To the reaction mixture was added ice-water, followed by extraction with ethyl acetate. The organic layer was washed with water, then dried over anhydrous sodium sulfate, and concentrated under reduced pressure to obtain [(1R)-6-hydroxy-1,2,3,4-tetrahydronaphthalen-1-yl]acetic acid or an enantiomer thereof (147 mg).

Preparation Example 32

To a solution of [(1R)-6-methoxy-1,2,3,4-tetrahydronaphthalen-1-yl]acetic acid or an enantiomer thereof (288 mg) obtained in Preparation Example 30 in dichloromethane (9.77 mL) was added dropwise a 1 M solution (2.66 mL) of boron tribromide in dichloromethane under ice-cooling, followed by stirring at room temperature for 2 hours. To the reaction mixture was added ice-water, followed by extraction with ethyl acetate. The organic layer was washed with a saturated aqueous sodium chloride solution, then dried over anhydrous sodium sulfate, and concentrated under reduced pressure. The residue was purified by silica gel column chromatography (hexane-ethyl acetate) to obtain [(1R)-6-hydroxy-1,2,3,4-tetrahydronaphthalen-1-yl]acetic acid or an enantiomer thereof (230 mg).

Preparation Example 33

To a solution of [(1R)-6-hydroxy-1,2,3,4-tetrahydronaphthalen-1-yl]acetic acid or an enantiomer thereof (145 mg) obtained in Preparation Example 31 in N,N-dimethylformamide (2.90 mL) were added tert-butyl 4-({[(2R)-1-tert-butoxy-1-oxopropan-2-yl]amino}methyl)thiophene-2-carboxylate (255 mg), O-(7-azabenzotriazol-1-yl)-N,N,N',N'-tetramethyluronium hexafluorophosphate (295 mg), and N,N-diisopropylethylamine (135 µL), followed by stirring at room temperature overnight. To the reaction solution was added water, followed by extraction with ethyl acetate. The organic layer was washed with water, then dried over anhydrous sodium sulfate, and concentrated under reduced pressure. The residue was purified by silica gel column chromatography (hexane-ethyl acetate) to obtain tert-butyl 4-[([(2R)-1-tert-butoxy-1-oxopropan-2-yl]{[(1R)-6-hydroxy-1,2,3,4-tetrahydronaphthalen-1-yl]acetyl}amino)methyl]thiophene-2-carboxylate or an epimer at position 1 of the 1,2,3,4-tetrahydronaphthalene (237 mg).

Preparation Example 34

To a solution of tert-butyl 4-[([(2R)-1-tert-butoxy-1-oxopropan-2-yl]{[(1R)-6-hydroxy-1,2,3,4-tetrahydronaphthalen-1-yl]acetyl}amino)methyl]thiophene-2-carboxylate or an epimer at position 1 of the 1,2,3,4-tetrahydronaphthalene (235 mg) obtained in Preparation Example 33 in dichloromethane (3.00 mL) were added N-[3-(dimethylamino)propyl]-N'-ethylcarbodiimide hydrochloride (115 mg), 4-[N',N''-bis(tert-butoxycarbonyl)carbamimidamide]benzoic acid (220 mg), and 4-dimethylaminopyridine (18.0 mg), followed by stirring at room temperature for 3 hours. To the reaction solution was added water, followed by extraction with ethyl acetate. The organic layer was washed with water, then dried over anhydrous sodium sulfate, and concentrated under reduced pressure. The residue was purified by silica gel column chromatography (hexane-ethyl acetate) to obtain tert-butyl 4-[({[(1R)-6-({4-[N',N''-bis(tert-butoxycarbonyl)carbamimidamnide]benzoyl}oxy)-1,2,3,4-tetrahydronaphthalen-1-yl]acetyl}[(2R)-1-tert-butoxy-1-oxopropan-2-yl]amino)methyl]thiophene-2-carboxylate or an epimer at position 1 of the 1,2,3,4-tetrahydronaphthalene (325 mg).

Preparation Example 35

To a solution of [(1R)-6-hydroxy-1,2,3,4-tetrahydronaphthalen-1-yl]acetic acid or an enantiomer thereof (228 mg) obtained in Preparation Example 32 in N,N-dimethylformamide (4.56 mL) were added O-(7-azabenzotriazol-1-yl)-N,N,N',N'-tetramethyluronium hexafluorophosphate (504 mg), N,N-diisopropylethylamine (227 µL), and tert-butyl 4-({[(2R)-1-tert-butoxy-1-oxopropan-2-yl]amino}methyl)thiophene-2-carboxylate (453 mg), followed by stirring at room temperature overnight. The reaction solution was diluted with ethyl acetate. The organic layer was sequentially washed with water and a saturated aqueous sodium chloride solution, then dried over anhydrous sodium sulfate, and concentrated under reduced pressure. The residue was purified by silica gel column chromatography (hexane-ethyl acetate) to obtain tert-butyl 4-[([(2R)-1-tert-butoxy-1-oxopropan-2-yl]{[(1R)-6-hydroxy-1,2,3,4-tetrahydronaphthalen-1-yl]acetyl}amino)methyl]thiophene-2-carboxylate or an epimer at position 1 of the 1,2,3,4-tetrahydronaphthalene (330 mg).

Preparation Example 36

To a mixture of tert-butyl 4-[([(2R)-1-tert-butoxy-1-oxopropan-2-yl]{[(1R)-6-hydroxy-1,2,3,4-tetrahydronaphthalen-1-yl]acetyl}amino)methyl]thiophene-2-carboxylate or an epimer at position 1 of the 1,2,3,4-tetrahydronaphthalene (328 mg) obtained in Preparation Example 35, 4-[N',N''-bis(tert-butoxycarbonyl)carbamimidamide]benzoic acid (282 mg), 4-dimethylaminopyridine (22.7 mg), and dichloromethane (4.92 mL) was added N-[3-(dimethylamino)propyl]-N'-ethylcarbodiimide hydrochloride (154 mg), followed by stirring at room temperature for 4 hours. The reaction mixture was concentrated under reduced pressure. The residue was purified by silica gel column chromatography (hexane-ethyl acetate) to obtain tert-butyl 4-[({[(1R)-6-({4-[N',N''-bis(tert-butoxycarbonyl)carbamimidamide]benzoyl}oxy)-1,2,3,4-tetrahydronaphthalen-1-yl]acetyl}[(2R)-1-tert-butoxy-1-oxopropan-2-yl]amino)methyl]thiophene-2-carboxylate or an epimer at position 1 of the 1,2,3,4-tetrahydronaphthalene (460 mg).

Preparation Example 37 tert-Butyl 3-{[{[6-({4-[N',N''-bis(tert-butoxycarbonyl)carbamimidamide]benzoyl}oxy)-1,2,3,4-tetrahydronaphthalen-1-yl]acetyl}(2-tert-butoxy-2-oxoethyl)amino]methyl}benzoate (395 mg) was preparatively purified by a supercritical chromatography method (carbon dioxide-methanol) by means of a UV trigger, and then concentrated under reduced pressure to obtain PEx. 37-1 (188 mg, RT: 4.02 min) and PEx. 37-2 (187 mg, RT: 4.87 min) as the tert-butyl 3-{[{[(1R)-6-({4-[N',N''-bis(tert-butoxycarbonyl)

carbamimidamide]benzoyl}oxy)-1,2,3,4-tetrahydronaphthalen-1-yl]acetyl}(2-tert-butoxy-2-oxoethyl)amino]methyl}benzoate and an enantiomer thereof. Further, the analysis conditions for the supercritical chromatography method carried out to determine RT are shown below.

Column: CHIRALCEL OZ-H/SFC 4.6 mm I.D.×250 mm (particle diameter: 5 μm), manufactured by Daicel Chemical Industries, Ltd.
Mobile phase: carbon dioxide 65%, methanol 35%
Flow rate: 3 mL/min (6 min)
Detection wavelength: 220 nm to 300 nm
Column temperature: 40° C.
Discharge pressure: 100 bar Preparation Example 38

A mixture of 6-hydroxy-1-naphthoic acid (150 mg), tert-butyl 4-(tert-butoxycarbonyl)-L-phenylalaninate (200 mg), N-[3-(dimethylamino)propyl]-N'-ethylcarbodiimide hydrochloride (160 mg), 1H-benzotriazol-1-ol (110 mg), and N,N-dimethylformamide (4.00 mL) was stirred at room temperature overnight. To the reaction mixture was added water, followed by stirring for 1 hour. The precipitate was collected by filtration, washed with water, and then dried under reduced pressure to obtain tert-butyl 4-(tert-butoxycarbonyl)-N-(6-hydroxy-1-naphthoyl)-L-phenylalaninate (183 mg).

Preparation Example 39

A mixture of tert-butyl 4-(tert-butoxycarbonyl)-N-(6-hydroxy-1-naphthoyl)-L-phenylalaninate (180 mg), 4-[N',N"-bis(tert-butoxycarbonyl)carbamimidamide]benzoic acid (180 mg), N-[3-(dimethylamino)propyl]-N'-ethylcarbodiimide hydrochloride (90.0 mg), 4-dimethylaminopyridine (15.0 mg), and dichloromethane (2.00 mL) was stirred at room temperature for 2 hours. The reaction mixture was purified by silica gel column chromatography (hexane-ethyl acetate) to obtain tert-butyl N-[6-({4-[N',N"-bis(tert-butoxycarbonyl)carbamimidamide]benzoyl}oxy)-1-naphthoyl]-4-(tert-butoxycarbonyl)-L-phenylalaninate (303 mg).

Preparation Example 40

To a solution of 6-hydroxy-1,2,3,4-tetrahydronaphthalene-2-carboxylic acid (200 mg) in N,N-dimethylformamide (3.00 mL) were added tert-butyl 4-{[(2-tert-butoxy-2-oxoethyl)amino]methyl}thiophene-2-carboxylate (341 mg), O-(7-azabenzotriazol-1-yl)-N,N,N',N'-tetramethyluronium hexafluorophosphate (435 mg), and N,N-diisopropylethylamine (196 μL), followed by stirring at room temperature for 2 hours. To the reaction mixture was added water, followed by extraction with ethyl acetate. The organic layer was dried over anhydrous magnesium sulfate, and concentrated under reduced pressure. The residue was purified by silica gel column chromatography (hexane-ethyl acetate) to obtain tert-butyl 4-({(2-tert-butoxy-2-oxoethyl)[(6-hydroxy-1,2,3,4-tetrahydronaphthalen-2-yl)carbonyl]amino}methyl)thiophene-2-carboxylate (522 mg).

Preparation Example 41

To a solution of tert-butyl 4-({(2-tert-butoxy-2-oxoethyl)[(6-hydroxy-1,2,3,4-tetrahydronaphthalen-2-yl)carbonyl]amino}methyl)thiophene-2-carboxylate (520 mg) in dichloromethane (10.4 mL) were added 4-[N',N"-bis(tert-butoxycarbonyl)carbamimidamide]benzoic acid (433 mg), N-[3-(dimethylamino)propyl]-N'-ethylcarbodiimide hydrochloride (298 mg), and 4-dimethylaminopyridine (38.0 mg) under ice-cooling, followed by stirring at room temperature for 2 hours. To the reaction solution were added water and 1 M hydrochloric acid, followed by extraction with chloroform. The organic layer was dried over anhydrous magnesium sulfate and concentrated under reduced pressure. The residue was purified by silica gel column chromatography (hexane-ethyl acetate) to obtain tert-butyl 4-{[{[6-({4-[N',N"-bis(tert-butoxycarbonyl)carbamimidamide]benzoyl}oxy)-1,2,3,4-tetrahydronaphthalen-2-yl]carbonyl}(2-tert-butoxy-2-oxoethyl)amino]methyl}thiophene-2-carboxylate (723 mg).

Preparation Example 42

To a solution of (3R)-2-(tert-butoxycarbonyl)-7-hydroxy-1,2,3,4-tetrahydroisoquinoline-3-carboxylic acid (1.50 g) in toluene (60.0 mL), and methanol (9.00 mL) was added dropwise a 0.60 M solution (10.0 mL) of trimethylsilyldiazomethane in hexane, followed by stirring at room temperature for 30 minutes. To the reaction mixture was added acetic acid (300 μL), and then an aqueous sodium hydrogen carbonate solution was added thereto, followed by extraction with ethyl acetate. The organic layer was sequentially washed with water and a saturated aqueous sodium chloride solution, then dried over anhydrous sodium sulfate, and concentrated under reduced pressure. The residue was purified by silica gel column chromatography (hexane-ethyl acetate) to obtain 2-tert-butyl 3-methyl (3R)-7-hydroxy-3,4-dihydroisoquinoline-2,3(1H)-dicarboxylate (1.47 g).

Preparation Example 43

To a solution of dibenzyl (3R)-2-{[6-({4-[N',N"-bis(tert-butoxycarbonyl)carbamimidamide]benzoyl}oxy)-1,2,3,4-tetrahydronaphthalen-1-yl]acetyl}-1,2,3,4-tetrahydroisoquinoline-3,7-dicarboxylate (257 mg) in ethanol (5.00 mL) was added 10% palladium-carbon (52.0 mg, 50% wet product), followed by stirring at room temperature for 2 hours at normal pressure in a hydrogen atmosphere. The reaction mixture was filtered by passing it through a Celite (registered trademark) layer, and then the filtrate was concentrated under reduced pressure to obtain (3R)-2-{[6-({4-[N',N"-bis(tert-butoxycarbonyl)carbamimidamide]benzoyl}oxy)-1,2,3,4-tetrahydronaphthalen-1-yl]acetyl}-1,2,3,4-tetrahydroisoquinoline-3,7-dicarboxylic acid (213 mg).

Preparation Example 44

A mixture of di-tert-butyl 3-[(benzyl {[6-(benzyloxy)-1,2,3,4-tetrahydronaphthalen-1-yl]acetyl}amino)methyl]pentanedioate (230 mg), 10% palladium-carbon (38.1 mg, 50% wet product), and methanol (4.60 mL) was stirred at room temperature for 16 hours at normal pressure in a hydrogen atmosphere. The reaction mixture was filtered by passing it through a Celite (registered trademark) layer, and then the filtrate was concentrated under reduced pressure to obtain di-tert-butyl 3-({benzyl[(6-hydroxy-1,2,3,4-tetrahydronaphthalen-1-yl)acetyl]amino}methyl)pentanedioate (186 mg).

Example 1

To tert-butyl 4-({[6-({4-[N',N"-bis(tert-butoxycarbonyl)carbamimidamide]benzoyl}oxy)-2-naphthoyl](2-tert-butoxy-2-oxoethyl)amino}methyl)thiophene-2-carboxylate (132 mg) was added a 4 M solution (2.02 mL) of hydrogen chloride in 1,4-dioxane, followed by stirring at room temperature for 24 hours. The reaction suspension was concentrated under reduced pressure, and then the residue was purified by octadecylsilyl (hereinafter referred to as ODS) column chromatography (0.01 M hydrochloric acid-acetonitrile) to obtain 4-{[{6-[(4-carbamimidamidobenzoyl)oxy]-2-naphthoyl}(carboxymethyl)amino]methyl}thiophene-2-carboxylic acid monohydrochloride (62.7 mg).

Example 2

To a solution of tert-butyl 3-{[{[6-({4-[N',N''-bis(tert-butoxycarbonyl)carbamimidamide]benzoyl}oxy)-1,2,3,4-tetrahydronaphthalen-1-yl]acetyl}(2-tert-butoxy-2-oxoethyl)amino]methyl}benzoate (528 mg) in dichloromethane (5.00 mL) was added trifluoroacetic acid (2.00 mL), followed by stirring at room temperature for 2 hours. The reaction mixture was concentrated under reduced pressure, and then to the residue were added 1 M hydrochloric acid (606 μL) and acetonitrile (10.0 mL), followed by concentrating under reduced pressure. The residue was purified by ODS column chromatography (0.01 M hydrochloric acid-acetonitrile) and dried under reduced pressure to obtain 3-{[({6-[(4-carbamimidamnidobenzoyl)oxy]-1,2,3,4-tetrahydronaphthalen-1-yl}acetyl)(carboxymethyl)amino]methyl}benzoic acid monohydrochloride (227 mg).

Example 3

To a solution of tert-butyl N-[6-({4-[N',N''-bis(tert-butoxycarbonyl)carbamimidamide]benzoyl}oxy)-1-naphthoyl]-4-(tert-butoxycarbonyl)-L-phenylalaninate (300 mg) in dichloromethane (1.50 mL) was added trifluoroacetic acid (1.50 mL), followed by stirring at room temperature for 2 hours. The reaction mixture was concentrated under reduced pressure, and then to the residue were added 1 M hydrochloric acid (1.00 mL) and acetonitrile (1.00 mL), followed by concentrating under reduced pressure. The residue was purified by ODS column chromatography (0.01 M hydrochloric acid-acetonitrile) to obtain N-{6-[(4-carbamimidamidobenzoyl)oxy]-1-naphthoyl}-4-carboxy-L-phenylalanine monohydrochloride (158 mg).

Example 4

To a solution of tert-butyl 4-{[{[6-({4-[N',N''-bis(tert-butoxycarbonyl)carbamimidamide]benzoyl}oxy)-1,2,3,4-tetrahydronaphthalen-2-yl]carbonyl}(2-tert-butoxy-2-oxoethyl)amino]methyl}thiophene-2-carboxylate (720 mg) in dichloromethane (5.33 mL) was added trifluoroacetic acid (5.36 mL), followed by stirring at room temperature for 5 hours. To the reaction mixture was added acetonitrile, followed by concentrating under reduced pressure. The residue was purified by ODS column chromatography (0.01 M hydrochloric acid-acetonitrile) to obtain 4-{[({6-[(4-carbamimidamidobenzoyl)oxy]-1,2,3,4-tetrahydronaphthalen-2-yl}carbonyl)(carboxymethyl)amino]methyl}thiophene-2-carboxylic acid monohydrochloride (440 mg).

Example 5

To a solution of tert-butyl 3-{[{[(1R)-6-({4-[N',N''-bis(tert-butoxycarbonyl)carbamimidamide]benzoyl}oxy)-1,2,3,4-tetrahydronaphthalen-1-yl]acetyl}(2-tert-butoxy-2-oxoethyl)amino]methyl}benzoate or an enantiomer thereof (PEx. 37-1, 181 mg) obtained in Preparation Example 37 in dichloromethane (3.00 mL) was added trifluoroacetic acid (686 μL), followed by stirring at room temperature for 4 hours. The reaction solution was concentrated under reduced pressure, and then to the residue were added 1 M hydrochloric acid (208 μL) and acetonitrile (10.0 mL), followed by concentrating under reduced pressure. The residue was purified by ODS column chromatography (0.01 M hydrochloric acid-acetonitrile) and dried under reduced pressure to obtain a monohydrochloride (91 mg, RT 10.6 min) of 3-{[({(1R)-6-[(4-carbamimidamidobenzoyl)oxy]-1,2,3,4-tetrahydronaphthalen-1-yl}acetyl)(carboxymethyl)amino]methyl}benzoic acid or an enantiomer thereof. Further, the analysis conditions for the chiral column chromatography method carried out to determine RT are shown below.

Column: CHIRALPAK IE-3 4.6 mm I.D.×250 mm (particle diameter: 3 μm), manufactured by Daicel Chemical Industries, Ltd.

Mobile phase: hexane (containing 0.1% trifluoroacetic acid) 60%, ethanol (containing 0.1% trifluoroacetic acid) 40%

Flow rate: 1 mL/min

Detection wavelength: 254 nm

Column temperature: 40° C.

Example 6

To a solution of tert-butyl 3-{[{[(1R)-6-({4-[N',N''-bis(tert-butoxycarbonyl)carbamimidamide]benzoyl}oxy)-1,2,3,4-tetrahydronaphthalen-1-yl]acetyl}(2-tert-butoxy-2-oxoethyl)amino]methyl}benzoate or an enantiomer thereof (PEx. 37-2, 183 mg) obtained in Preparation Example 37 in dichloromethane (3.03 mL) was added trifluoroacetic acid (693 μL), followed by stirring at room temperature for 4 hours. The reaction solution was concentrated under reduced pressure, and then to the residue were added 1 M hydrochloric acid (210 μL) and acetonitrile (10.0 mL), followed by concentrating under reduced pressure. The residue was purified by ODS column chromatography (0.01 M hydrochloric acid-acetonitrile) and dried under reduced pressure to obtain a monohydrochloride (98 mg, RT 14.1 min) of 3-{[({(1R)-6-[(4-carbamimidamidobenzoyl)oxy]-1,2,3,4-tetrahydronaphthalen-1-yl}acetyl)(carboxymethyl)amino]methyl}benzoic acid or an enantiomer thereof. Further, the analysis conditions for the chiral column chromatography method carried out to determine RT are shown below.

Column: CHIRALPAK IE-3 4.6 mm I.D.×250 mm (particle diameter: 3 μm), manufactured by Daicel Chemical Industries, Ltd.

Mobile phase: hexane (containing 0.1% trifluoroacetic acid) 60%, ethanol (containing 0.1% trifluoroacetic acid) 40%

Flow rate: 1 mL/min

Detection wavelength: 254 nm

Column temperature: 40° C.

Example 7

To a solution of tert-butyl 4-[({[(1R)-6-({4-[N',N''-bis(tert-butoxycarbonyl)carbamimidamide]benzoyl}oxy)-1,2,3,4-tetrahydronaphthalen-1-yl]acetyl}[(2R)-1-tert-butoxy-1-oxopropan-2-yl]amino)methyl]thiophene-2-carboxylate or an epimer at position 1 of the 1,2,3,4-tetrahydronaphthalene (324 mg) obtained in Preparation Example 34 in dichloromethane (3.00 mL) was added trifluoroacetic acid (1.50 mL), followed by stirring at room temperature overnight. The reaction mixture was concentrated under reduced pressure, and then to the residue were added 1 M hydrochloric acid (2.00 mL) and acetonitrile (1.50 mL), followed by concentrating under reduced pressure. The residue was purified by ODS column chromatography (0.01 M hydrochloric acid-acetonitrile) to obtain hydrochloride (46 mg) of 4-({({(1R)-6-[(4-carbamimidamidobenzoyl)oxy]-1,2,3,4-tetrahydronaphthalen-1-yl}acetyl) [(1R)-1-carboxyethyl]amino}methyl)thiophene-2-carboxylic acid or an epimer at position 1 of the 1,2,3,4-tetrahydronaphthalene.

Example 8

To a solution of tert-butyl 4-[({[(1R)-6-({4-[N',N''-bis(tert-butoxycarbonyl)carbamimidamide]benzoyl}oxy)-1,2,3,4-tetrahydronaphthalen-1-yl]acetyl}[(2R)-1-tert-butoxy-1-oxopropan-2-yl]amino)methyl]thiophene-2-carboxylate or an epimer at position 1 of the 1,2,3,4-tetrahydronaphthalene (460 mg) obtained in Preparation Example 36 in dichloromethane (3.07 mL) was added trifluoroacetic acid (2.06 mL), followed by stirring at room temperature for 2 hours. The reaction mixture was concentrated under reduced pressure, and then to the residue were added 1 M hydrochloric acid (588 µL) and acetonitrile (3.07 mL), followed by concentrating under reduced pressure. To the residue was added ethyl acetate, followed by concentrating under reduced pressure. The obtained solid was washed with acetonitrile to obtain 4-({({(1R)-6-[(4-carbamimidamidobenzoyl)oxy]-1,2,3,4-tetrahydronaphthalen-1-yl}acetyl) [(1R)-1-carboxyethyl]amino}methyl)thiophene-2-carboxylic acid or an epimer at position 1 of the 1,2,3,4-tetrahydronaphthalene (44 mg).

Example 9

To a 50% aqueous acetonitrile solution (80.0 mL) of a monohydrochloride (3.83 g) of 3-{[({(1R)-6-[(4-carbamimidamidobenzoyl)oxy]-1,2,3,4-tetrahydronaphthalen-1-yl}acetyl)(carboxymethyl)amino]methyl}benzoic acid or an enantiomer thereof obtained in Example 6 was added dropwise a 1 M aqueous sodium hydroxide solution (6.44 mL) under ice-cooling, followed by stirring at room temperature for 3 hours. The precipitate was collected by filtration, then washed with a 50% aqueous acetonitrile solution, and dried in air for 1 hour. The dried product was suspended in a 50% aqueous acetonitrile solution (400 mL), followed by stirring at 120° C. for 30 minutes. The reaction mixture was stirred at room temperature for 12 hours. The precipitate was collected by filtration, then washed with a 50% aqueous acetonitrile solution, and dried at room temperature under reduced pressure to obtain 3-{[({(1R)-6-[(4-carbamimidamidobenzoyl)oxy]-1,2,3,4-tetrahydronaphthalen-1-yl}acetyl)(carboxymethyl)amino]methyl}benzoic acid or an enantiomer thereof (2.89 g).

The compounds of Preparation Examples and Examples shown in Tables below were prepared in the same manner as in Preparation Examples and Examples as described above.

TABLE 3

| PEx | PSyn | Str | Data |
|---|---|---|---|
| 1 | P1 | | ESI+: 328 |
| 2 | P2 | | ESI+: 520 [M + Na]+ |
| 3 | P3 | | ESI+: 859 |

TABLE 3-continued

| PEx | PSyn | Str | Data |
|---|---|---|---|
| 4 | P4 | 6-hydroxybenzo[b]thiophene-2-carboxylic acid | ESI+: 195 |
| 5 | P5 | 2-(tert-butoxycarbonyl)-1,2,3,4-tetrahydroisoquinoline-3,7-dicarboxylic acid | ESI+: 344 [M + Na]+ |

TABLE 4

| PEx | PSyn | Str | Data |
|---|---|---|---|
| 6 | P6 | tert-butyl 3-((N-(2-tert-butoxy-2-oxoethyl)-2-(6-hydroxy-1,2,3,4-tetrahydronaphthalen-1-yl)acetamido)methyl)benzoate | ESI+: 532 [M + Na]+ |
| 7 | P7 | tert-butyl 3-(((2-tert-butoxy-2-oxoethyl)amino)methyl)benzoate HCl | ESI+: 322 |
| 8 | P8 | 2-(6-hydroxy-1,2,3,4-tetrahydronaphthalen-1-yl)acetic acid | ESI+: 229 [M + Na]+ |
| 9 | P9 | Boc-protected guanidine intermediate | ESI+: 871 |

TABLE 4-continued
| PEx | PSyn | Str | Data |
|---|---|---|---|
| 10 | P10 | 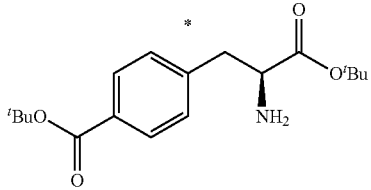 [SMILES: CC(C)(C)OC(=O)c1ccc(C[C@H](N)C(=O)OC(C)(C)C)cc1] | ESI+: 322 |
TABLE 5
| PEx | PSyn | Str | Data |
|---|---|---|---|
| 11 | P11 | 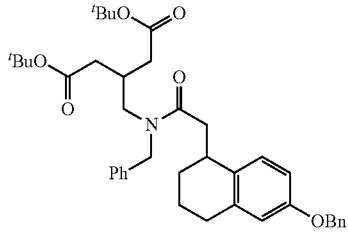 [SMILES: CC(C)(C)OC(=O)CC(CC(=O)OC(C)(C)C)CN(Cc1ccccc1)C(=O)CC1CCCc2cc(OCc3ccccc3)ccc21] | ESI+: 664 [M + Na]+ |
| 12 | P12 | 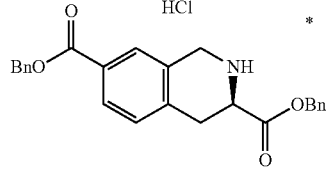 [SMILES: Cl ; O=C(OCc1ccccc1)c1ccc2c(c1)CN[C@@H](C(=O)OCc1ccccc1)C2] | ESI+: 402 |
| 13 | P13 | 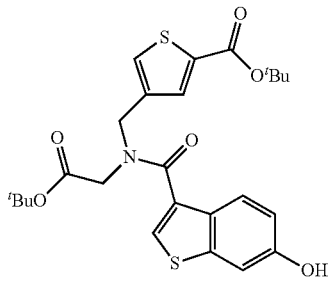 [SMILES: CC(C)(C)OC(=O)CN(Cc1csc(C(=O)OC(C)(C)C)c1)C(=O)c1csc2cc(O)ccc12] | ESI+: 526 [M + Na]+ |
| 14 | P14 | 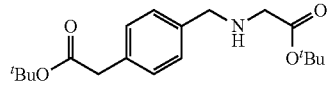 | ESI+: 336 |
| 15 | P15 | 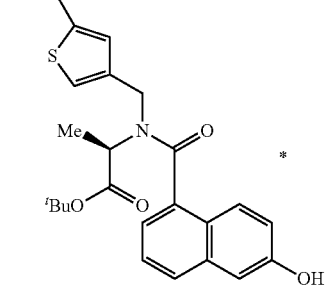 | ESI+: 534 [M + Na]+ |
TABLE 6
| PEx | PSyn | Str | Data |
|---|---|---|---|
| 16 | P16 | 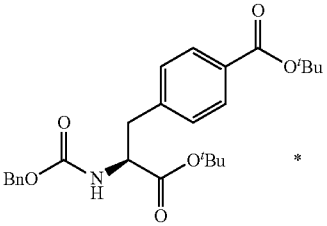 [SMILES: CC(C)(C)OC(=O)c1ccc(C[C@H](NC(=O)OCc2ccccc2)C(=O)OC(C)(C)C)cc1] | ESI+: 478 [M + Na]+ |
| 17 | P17 | 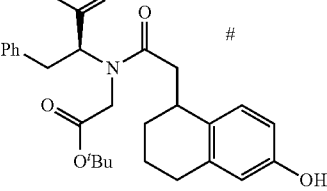 | ESI+: 546 [M + Na]+ |
| 18 | P18 | 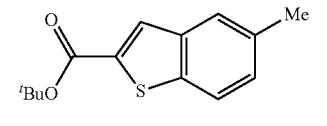 | ESI+: 271 [M + Na]+ |
| 19 | P19 | 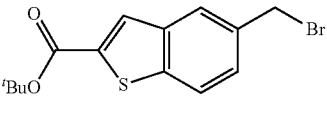 [SMILES: CC(C)(C)OC(=O)c1cc2cc(CBr)ccc2s1] | ESI+: 349 [M + Na]+ |
| 20 | P20 | 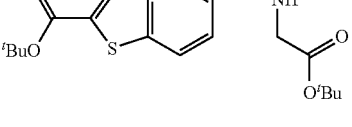 | ESI+: 378 |
| 21 | P21 | 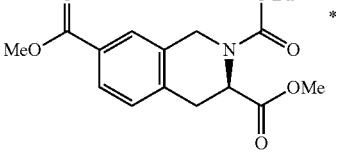 | ESI+: 372 [M + Na]+ |
| 22 | P22 | 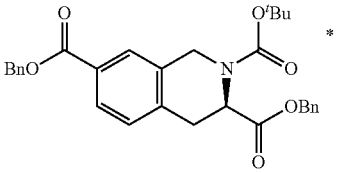 [SMILES: CC(C)(C)OC(=O)N1Cc2cc(C(=O)OCc3ccccc3)ccc2C[C@@H]1C(=O)OCc1ccccc1] | ESI+: 524 [M + Na]+ |

TABLE 6-continued

| PEx | PSyn | Str | Data |
|---|---|---|---|
| 23 | P23 | (structure: tBuO-CH2-thiophene-CHO) | ESI+: 249 [M + Na]+ |

TABLE 7

| PEx | PSyn | Str | Data |
|---|---|---|---|
| 24 | P24 | (structure: tBuO2C-CH2-thiophene-CH2-NH-CH2-CO2tBu) | ESI+: 342 |
| 25 | P25 | (structure: tBuO2C-CH2-phenyl-CH2-NH-CH2-CO2tBu) | ESI+: 336 |
| 26 | P26 | (structure: cyclopentene-CH2-N(Bn)-C(O)-CH2-tetrahydronaphthalene-OBn) | ESI+: 466 |

TABLE 7-continued

| PEx | PSyn | Str | Data |
|---|---|---|---|
| 27 | P27 | (structure: dihydroxycyclopentane-CH2-N(Bn)-C(O)-CH2-tetrahydronaphthalene-OBn) | ESI+: 522 [M + Na]+ |
| 28 | P28 | (structure: HOOC-CH2-CH(COOH)-CH2-N(Bn)-C(O)-CH2-tetrahydronaphthalene-OBn) | ESI+: 530 |
| 29 | P29 | (structure: MeO-tetrahydronaphthalene-CH2-COOH) ** | ESI−: 219 |

TABLE 8

| PEx | PSyn | Str | Data |
|---|---|---|---|
| 30 | P30 | (structure: MeO-tetrahydronaphthalene-CH2-COOH) ** | ESI−: 219 |
| 31 | P31 | (structure: HO-tetrahydronaphthalene-CH2-COOH) ** | ESI−: 205 |

TABLE 8-continued
| PEx | PSyn | Str | Data |
|---|---|---|---|
| 32 | P32 | 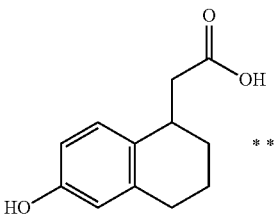 [SMILES: O=C(O)CC1CCCc2cc(O)ccc21] | ESI−: 205 |
| 33 | P33 | 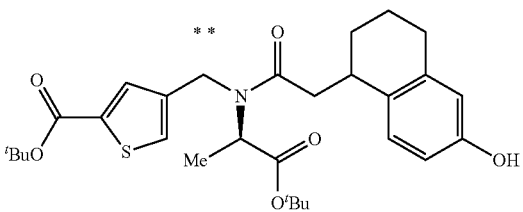 [SMILES: C[C@H](C(=O)OC(C)(C)C)N(Cc1csc(C(=O)OC(C)(C)C)c1)C(=O)CC1CCCc2cc(O)ccc21] | ESI+: 552 [M + Na]+ |
| 34 | P34 | 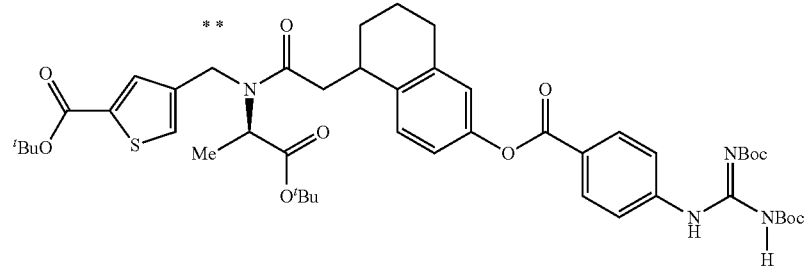 | ESI+: 891 |
| 35 | P35 | 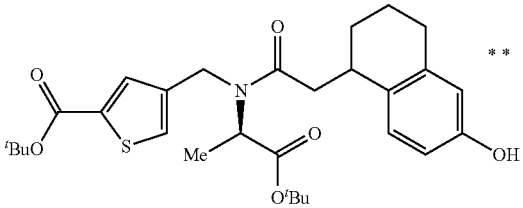 [SMILES: C[C@H](C(=O)OC(C)(C)C)N(Cc1csc(C(=O)OC(C)(C)C)c1)C(=O)CC1CCCc2cc(O)ccc21] | ESI+: 552 [M + Na]+ |
TABLE 9
| PEx | PSyn | Str | Data |
|---|---|---|---|
| 36 | P36 | 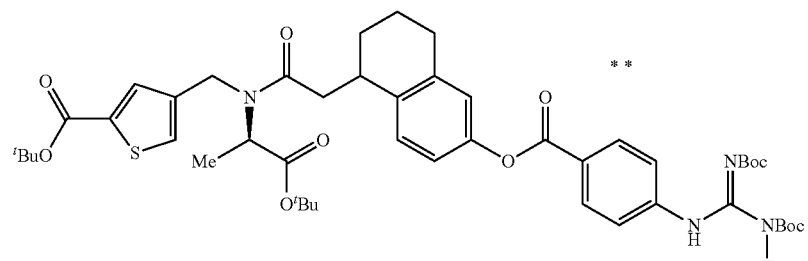 | ESI+: 891 |

TABLE 9-continued

| PEx | PSyn | Str | Data |
|---|---|---|---|
| 37-1 | P37 | | ESI+: 893 [M + Na]+ |
| 37-2 | P37 | | ESI+: 871 |
| 38 | P38 | | ESI+: 514 [M + Na]+ |

TABLE 10

| PEx | PSyn | Str | Data |
|---|---|---|---|
| 39 | P39 | | ESI+: 853 |

TABLE 10-continued

| PEx | PSyn | Str | Data |
|---|---|---|---|
| 40 | P40 | | ESI+: 524 [M + Na]+ |
| 41 | P41 | | ESI+: 863 |
| 42 | P42 | | ESI+: 330 [M + Na]+ |
| 43 | P43 | | ESI+: 771 |

TABLE 11

| PEx | PSyn | Str | Data |
|---|---|---|---|
| 44 | P44 | | ESI+: 574 [M + Na]+ |

TABLE 11-continued
| PEx | PSyn | Str | Data |
|---|---|---|---|
| 45 | P2 | 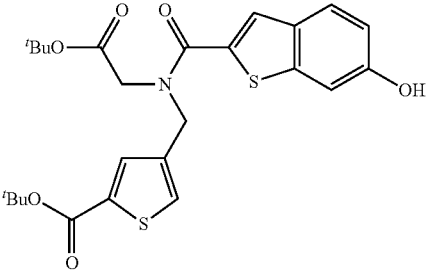 [SMILES: CC(C)(C)OC(=O)CN(Cc1csc(C(=O)OC(C)(C)C)c1)C(=O)c1cc2ccc(O)cc2s1] | ESI+: 526 [M + Na]+ |
| 46 | P3 | 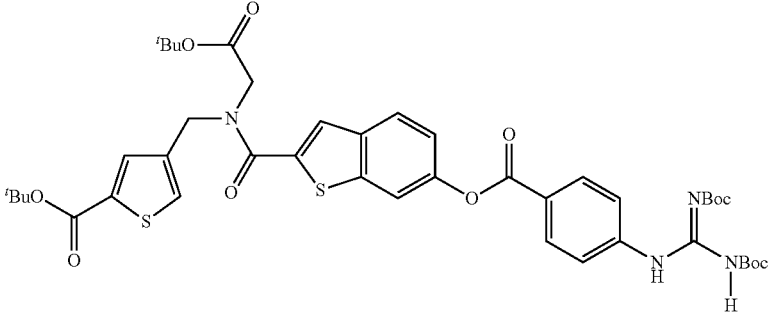 | ESI+: 865 |
| 47 | P6 | 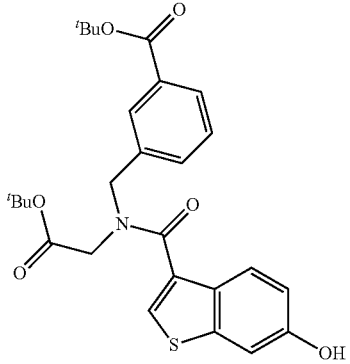 [SMILES: CC(C)(C)OC(=O)CN(Cc1cccc(C(=O)OC(C)(C)C)c1)C(=O)c1csc2cc(O)ccc12] | ESI+: 520 [M + Na]+ |
TABLE 12
| PEx | PSyn | Str | Data |
|---|---|---|---|
| 48 | P3 | 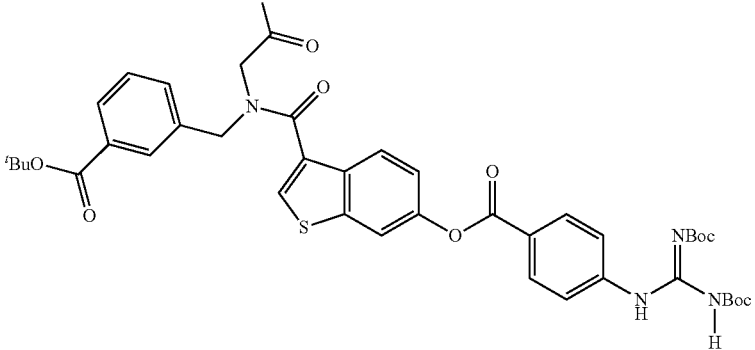 | ESI+: 859 |

TABLE 12-continued

| PEx | PSyn | Str | Data |
|---|---|---|---|
| 49 | P2 | | ESI+: 520 [M + Na]+ |
| 50 | P3 | | ESI+: 859 |
| 51 | P2 | | ESI+: 518 [M + Na]+ |

TABLE 13

| PEx | PSyn | Str | Data |
|---|---|---|---|
| 52 | P3 | | ESI+: 879 [M + Na]+ |

TABLE 13-continued
| PEx | PSyn | Str | Data |
|---|---|---|---|
| 53 | P2 | 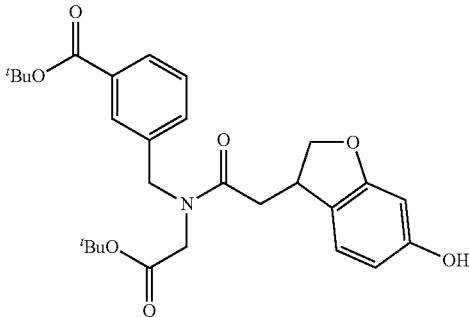 [SMILES: CC(C)(C)OC(=O)CN(Cc1cccc(C(=O)OC(C)(C)C)c1)C(=O)CC1COc2cc(O)ccc21] | ESI+: 520 [M + Na]+ |
| 54 | P3 | 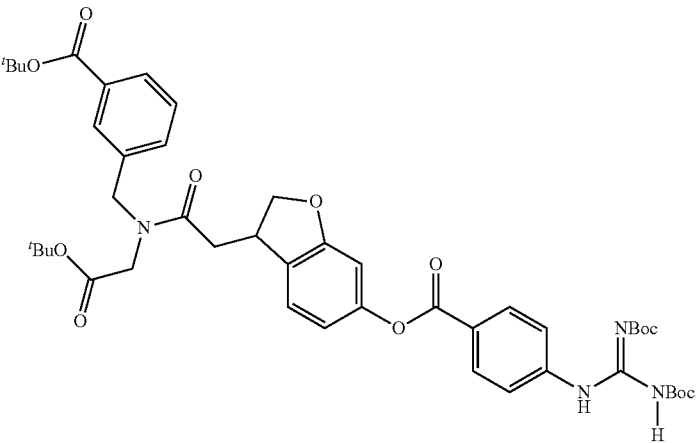 | ESI+: 881 [M + Na]+ |
| 55 | P2 | 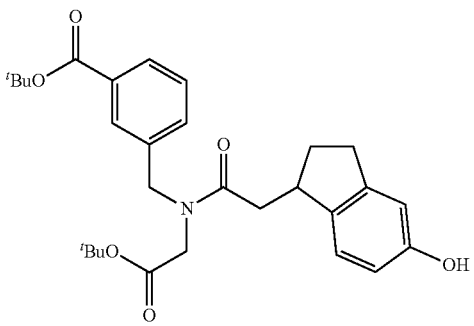 [SMILES: CC(C)(C)OC(=O)CN(Cc1cccc(C(=O)OC(C)(C)C)c1)C(=O)CC1CCc2cc(O)ccc21] | ESI+: 518 [M + Na]+ |

TABLE 14

| PEx | PSyn | Str | Data |
|---|---|---|---|
| 56 | P3 | | ESI+: 857 |
| 57 | P2 | | ESI+: 518 [M + Na]+ |
| 58 | P3 | | ESI+: 879 [M + Na]+ |
| 59 | P3 | | ESI+: 887 [M + Na]+ |

TABLE 15

| PEx | PSyn | Str | Data |
|---|---|---|---|
| 60 | P2 | | ESI+: 514 [M + Na]+ |
| 61 | P3 | | ESI+: 875 [M + Na]+ |
| 62 | P2 | | ESI+: 514 [M + Na]+ |
| 63 | P3 | | ESI+: 875 [M + Na]+ |
| 64 | P2 | | ESI+: 528 [M + Na]+ |

TABLE 16

| PEx | PSyn | Str | Data |
|---|---|---|---|
| 65 | P3 | | ESI+: 867 |
| 66 | P2 | | ESI+: 528 [M + Na]+ |
| 67 | P3 | | ESI+: 867 |
| 68 | P1 | | ESI+: 342 |

TABLE 17
| PEx | PSyn | Str | Data |
|---|---|---|---|
| 69 | P3 | 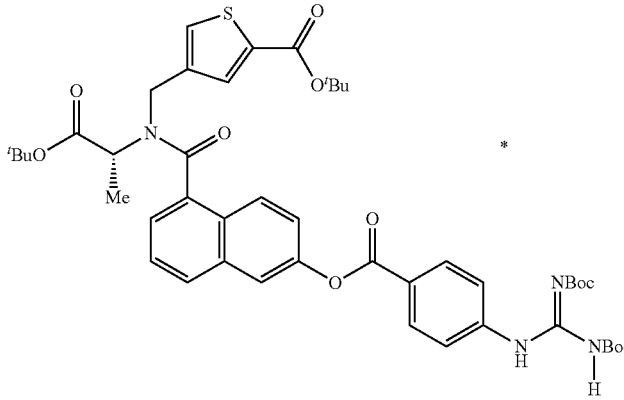 | ESI+: 873 |
| 70 | P2 | 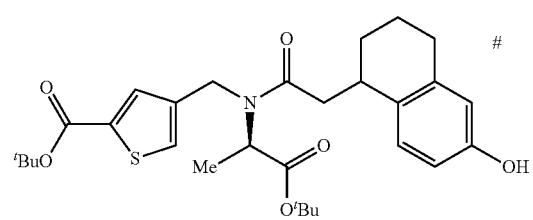 [SMILES: C[C@H](C(=O)OC(C)(C)C)N(Cc1csc(C(=O)OC(C)(C)C)c1)C(=O)CC1CCCc2cc(O)ccc21] | ESI+: 552 [M + Na]+ |
| 71 | P3 | 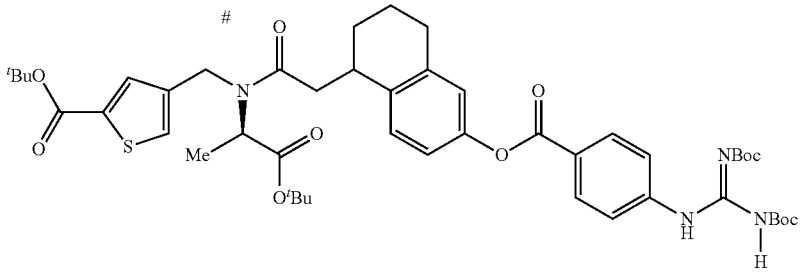 | ESI+: 891 |
| 72 | P6 | 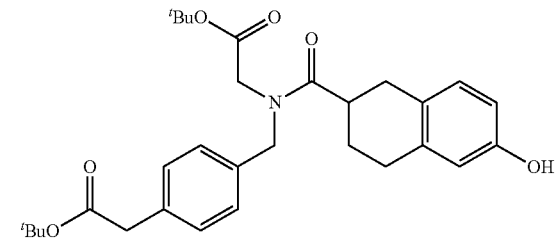 [SMILES: CC(C)(C)OC(=O)Cc1ccc(CN(CC(=O)OC(C)(C)C)C(=O)C2CCc3cc(O)ccc3C2)cc1] | ESI+: 532 [M + Na]+ |
| 73 | P3 | 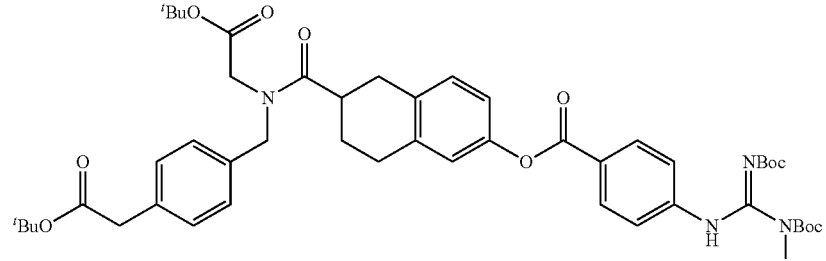 | ESI+: 871 |

TABLE 18
| PEx | PSyn | Str | Data |
|---|---|---|---|
| 74 | P2 | 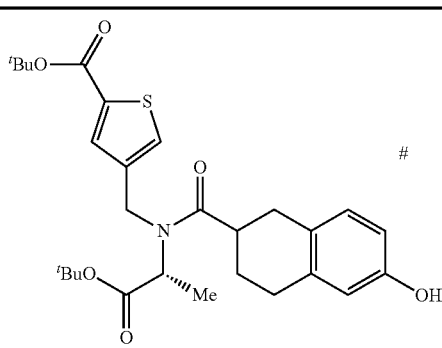 | ESI+: 538 [M + Na]+ |
| 75 | P3 | 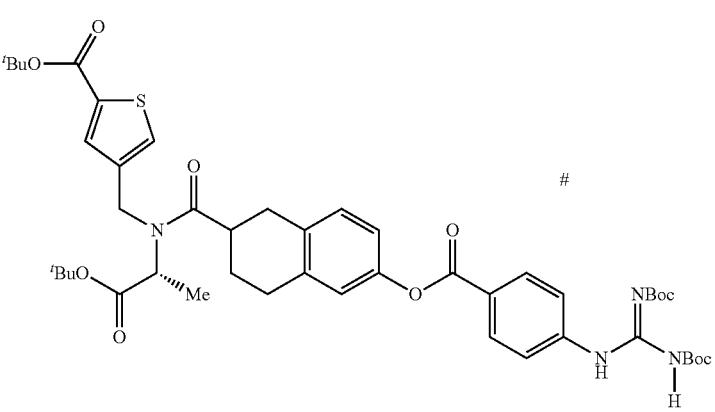 | ESI+: 877 |
| 76 | P3 | 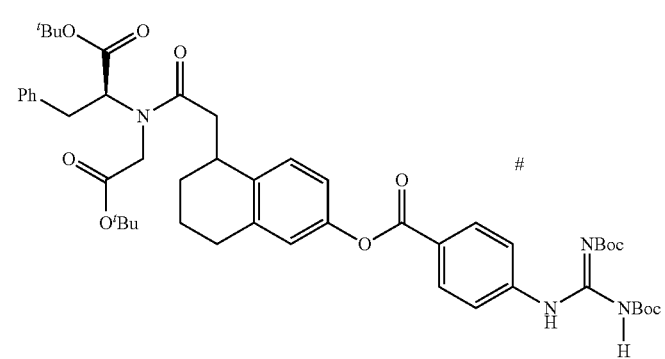 | ESI+: 885 |
| 77 | P6 | 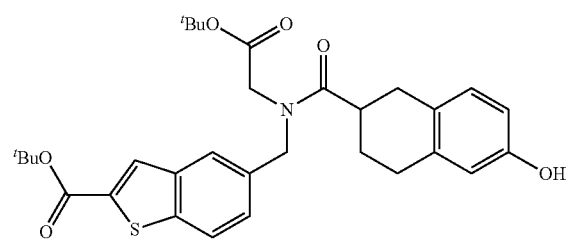 [SMILES: CC(C)(C)OC(=O)CN(Cc1ccc2sc(C(=O)OC(C)(C)C)cc2c1)C(=O)C1CCc2cc(O)ccc2C1] | ESI+: 552 |

TABLE 19

| PEx | PSyn | Str | Data |
|---|---|---|---|
| 78 | P3 | | ESI+: 913 |
| 79 | P6 | | ESI+: 588 [M + Na]+ |
| 80 | P3 | | ESI+: 927 |
| 81 | P6 | | ESI+: 546 [M + Na]+ |
| 82 | P3 | | ESI+: 885 |

TABLE 19-continued
| PEx | PSyn | Str | Data |
|---|---|---|---|
| 83 | P6 | 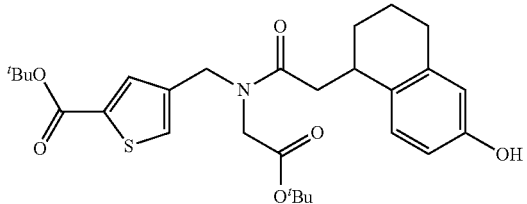 [SMILES: CC(C)(C)OC(=O)CN(Cc1csc(C(=O)OC(C)(C)C)c1)C(=O)CC1CCCc2cc(O)ccc21] | ESI+: 538 [M + Na]+ |
TABLE 20
| PEx | PSyn | Str | Data |
|---|---|---|---|
| 84 | P3 | 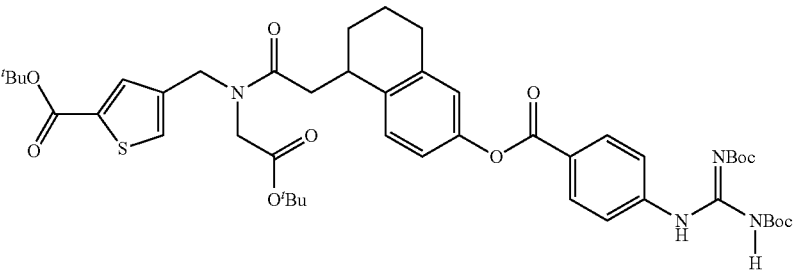 | ESI+: 877 |
| 85 | P20 | 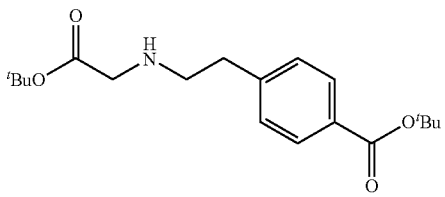 [SMILES: CC(C)(C)OC(=O)CNCCc1ccc(C(=O)OC(C)(C)C)cc1] | ESI+: 336 |
| 86 | P6 | 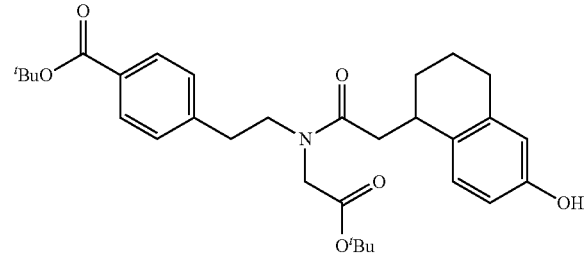 [SMILES: CC(C)(C)OC(=O)CN(CCc1ccc(C(=O)OC(C)(C)C)cc1)C(=O)CC1CCCc2cc(O)ccc21] | ESI+: 546 [M + Na]+ |
| 87 | P3 | 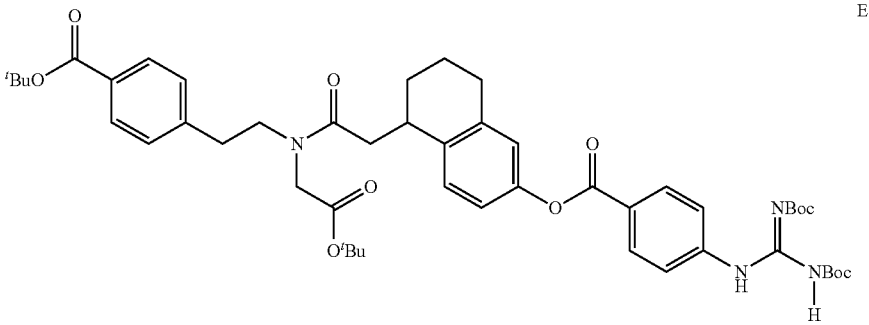 | ESI+: 885 |

TABLE 20-continued

| PEx | PSyn | Str | Data |
|---|---|---|---|
| 88 | P17 | (structure) | ESI+: 540 [M + Na]+ |

TABLE 21

| PEx | PSyn | Str | Data |
|---|---|---|---|
| 89 | P3 | (structure) | ESI+: 879 |
| 90 | P6 | (structure) | ESI+: 612 [M + Na]+ |
| 91 | P3 | (structure) | ESI+: 951 |

TABLE 21-continued
| PEx | PSyn | Str | Data |
|---|---|---|---|
| 92 | P17 | 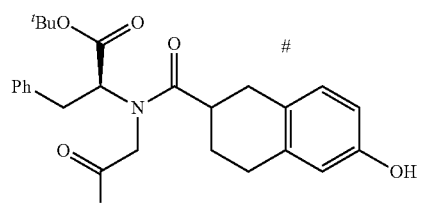 | ESI+: 532 [M + Na]+ |
| 93 | P3 | 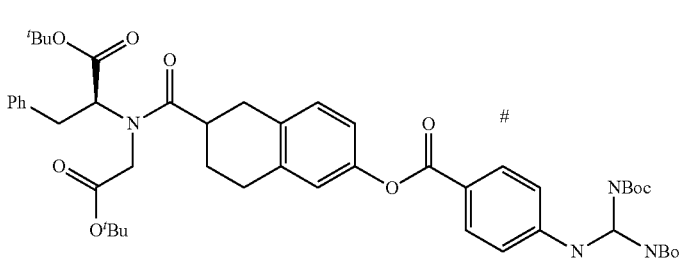 | ESI+: 871 |
TABLE 22
| PEx | PSyn | Str | Data |
|---|---|---|---|
| 94 | P17 | 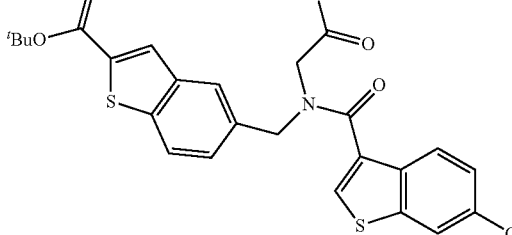 | ESI+: 576 [M + Na]+ |
| 95 | P3 | 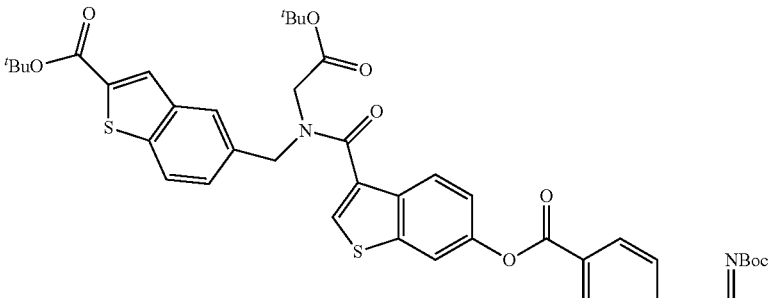 | ESI+: 915 |
| 96 | P6 | 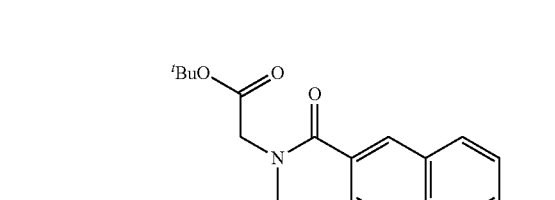 | ESI+: 570 [M + Na]+ |

TABLE 22-continued
| PEx | PSyn | Str | Data |
|---|---|---|---|
| 97 | P3 | 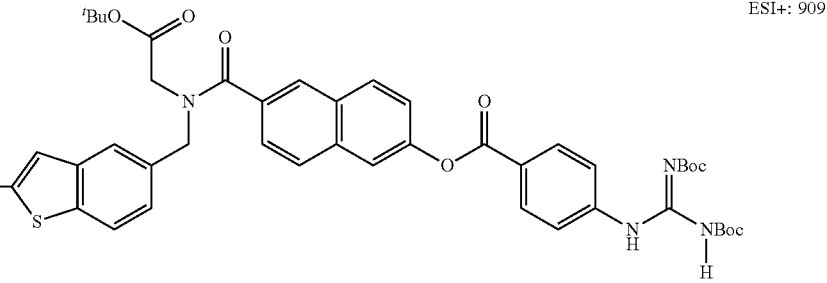 | ESI+: 909 |
| 98 | P6 | 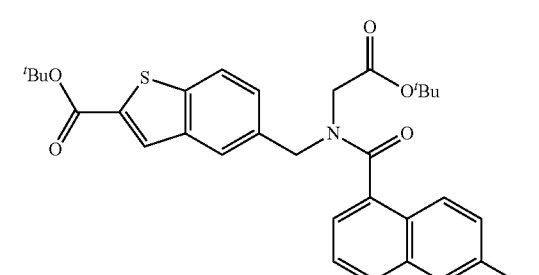 | ESI+: 570 [M + Na]+ |
TABLE 23
| PEx | PSyn | Str | Data |
|---|---|---|---|
| 99 | P3 | 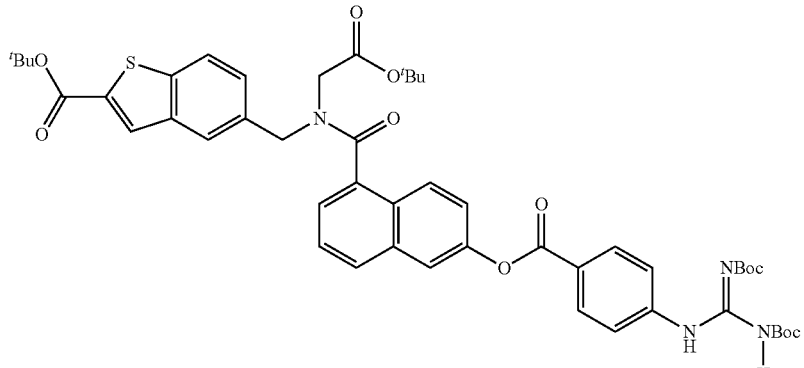 | ESI+: 909 |
| 100 | P6 | 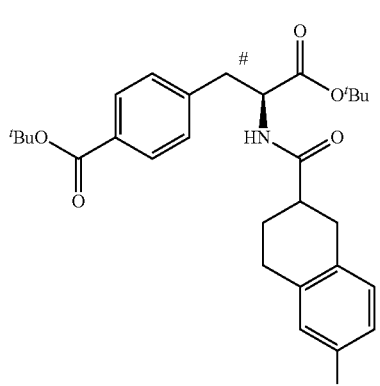 | ESI+: 518 [M + Na]+ |

TABLE 23-continued

| PEx | PSyn | Str | Data |
|---|---|---|---|
| 101 | P3 | | ESI+: 857 |
| 102 | P6 | | ESI+: 532 [M + Na]+ |
| 103 | P3 | | ESI+: 871 |

TABLE 24

| PEx | PSyn | Str | Data |
|---|---|---|---|
| 104 | P6 | | ESI+: 492 |

TABLE 24-continued
| PEx | PSyn | Str | Data |
|---|---|---|---|
| 105 | P3 | 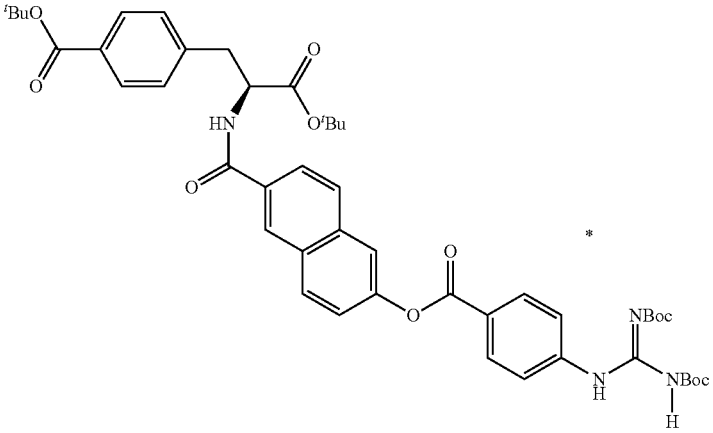 | ESI+: 853 |
| 106 | P16 | 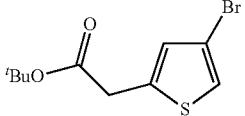 | ESI+: 299 [M + Na]+ |
| 107 | P2 | 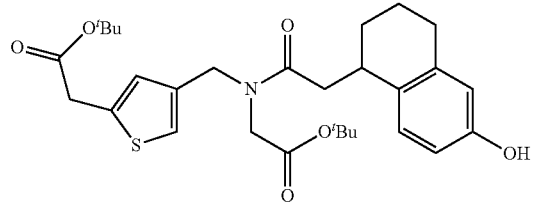 [SMILES: CC(C)(C)OC(=O)Cc1cc(CN(CC(=O)OC(C)(C)C)C(=O)CC2CCCc3cc(O)ccc32)cs1] | ESI+: 552 [M + Na]+ |
| 108 | P3 | 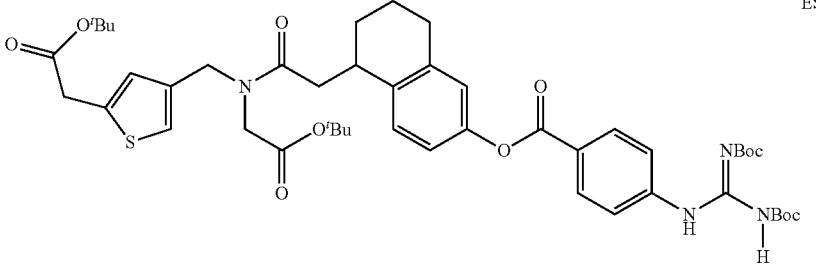 | ESI+: 891 |
| 109 | P17 | 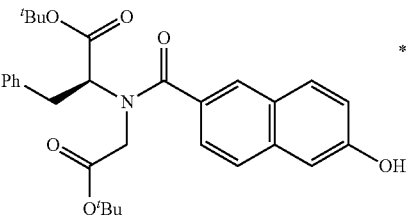 [SMILES: CC(C)(C)OC(=O)CN(C(=O)c1ccc2cc(O)ccc2c1)[C@@H](Cc1ccccc1)C(=O)OC(C)(C)C] | ESI+: 528 [M + Na]+ |

TABLE 25
| PEx | PSyn | Str | Data |
|---|---|---|---|
| 110 | P3 | 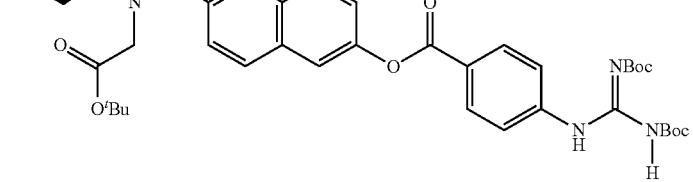 | ESI+: 867 |
| 111 | P17 | 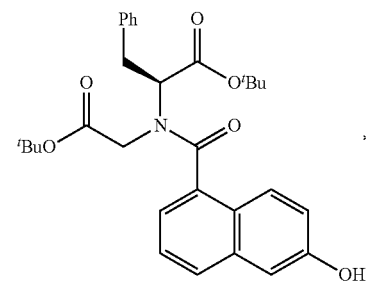 | ESI+: 528 [M + Na]+ |
| 112 | P3 | 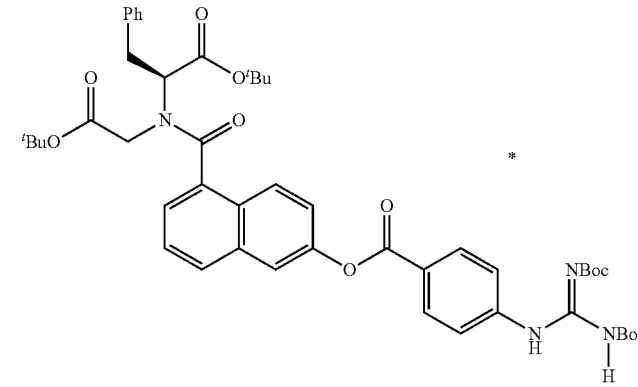 | ESI+: 867 |
| 113 | P6 | 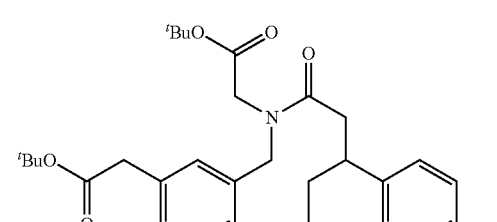 | ESI+: 546 [M + Na]+ |

TABLE 25-continued
| PEx | PSyn | Str | Data |
|---|---|---|---|
| 114 | P3 | | ESI+: 885 |
TABLE 26
| PEx | PSyn | Str | Data |
|---|---|---|---|
| 115 | P6 | | ESI+: 528 [M + Na]+ |
| 116 | P3 | | ESI+: 867 |
| 117 | P1 | 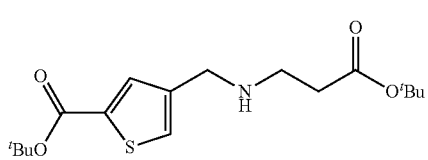 [SMILES: CC(C)(C)OC(=O)CCNCc1csc(C(=O)OC(C)(C)C)c1] | APCI/ESI+: 342 |

TABLE 26-continued

| PEx | PSyn | Str | Data |
|---|---|---|---|
| 118 | P17 | | APCI/ESI+: 512 |
| 119 | P3 | | NMR2: 1.33-1.65(36H, m), 2.25-5.09(6H, m), 7.11-7.98(10H, m), 8.16-8.26(2H, m), 10.66(1H, brs), 11.63(1H, brs) |

TABLE 27

| PEx | PSyn | Str | Data |
|---|---|---|---|
| 120 | P6 | | ESI+: 376 |
| 121 | P3 | | ESI+: 913 |

TABLE 27-continued

| PEx | PSyn | Str | Data |
|---|---|---|---|
| 122 | P6 | | ESI+: 538 [M + Na]+ |
| 123 | P3 | | ESI+: 877 |
| 124 | P17 | | ESI+: 532 [M + Na]+ |
| 125 | P3 | | ESI+: 871 |

TABLE 28

| PEx | PSyn | Str | Data |
|---|---|---|---|
| 126 | P17 | | ESI+: 520 [M + Na]+ |

TABLE 28-continued

| PEx | PSyn | Str | Data |
|---|---|---|---|
| 127 | P3 | | ESI+: 859 |
| 128 | P6 | | ESI+: 538 [M + Na]+ |
| 129 | P3 | | ESI+: 877 |
| 130 | P6 | | ESI+: 524 [M + Na]+ |

TABLE 29
| PEx | PSyn | Str | Data |
|---|---|---|---|
| 131 | P3 | 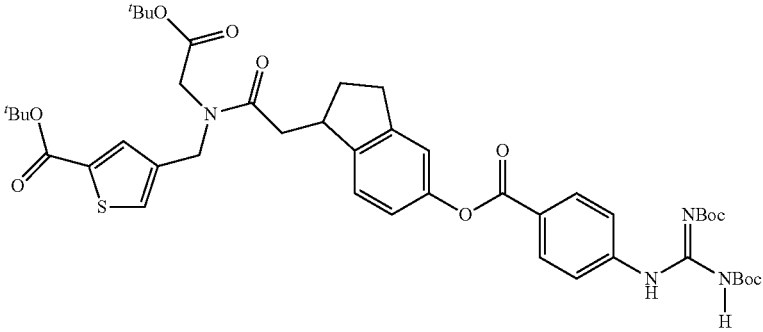 | ESI+: 863 |
| 132 | P6 | 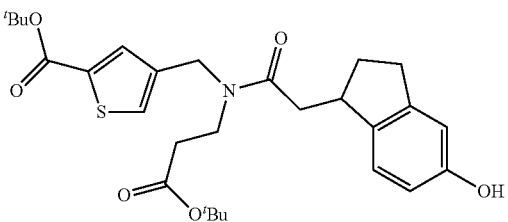 [SMILES: CC(C)(C)OC(=O)CCN(Cc1csc(C(=O)OC(C)(C)C)c1)C(=O)CC1CCc2cc(O)ccc21] | ESI+: 538 [M + Na]+ |
| 133 | P3 | 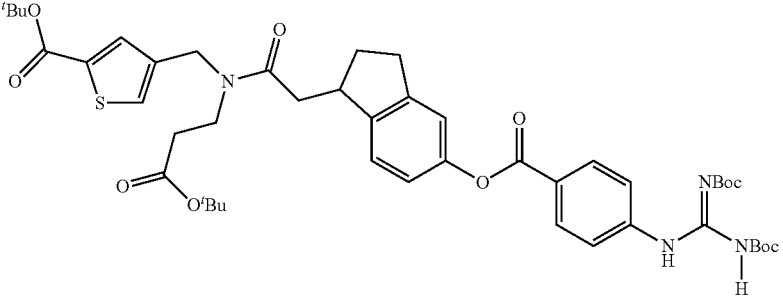 | ESI+: 877 |
| 134 | P6 | 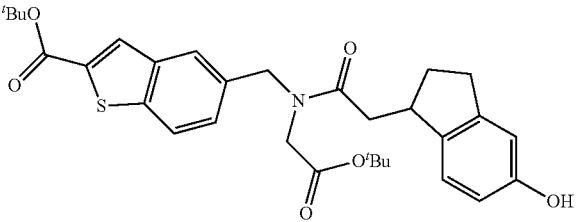 [SMILES: CC(C)(C)OC(=O)CN(Cc1ccc2sc(C(=O)OC(C)(C)C)cc2c1)C(=O)CC1CCc2cc(O)ccc21] | ESI+: 574 [M + Na]+ |
| 135 | P3 | 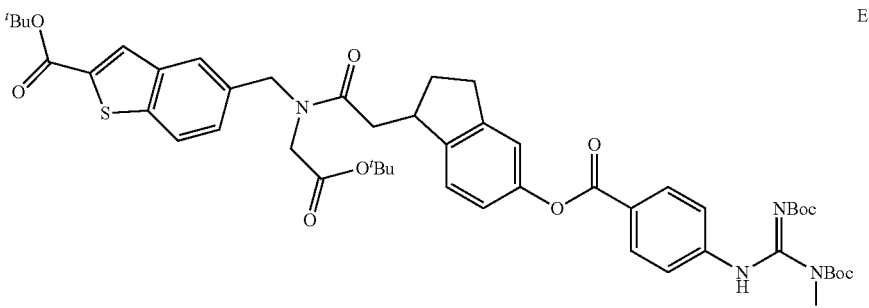 | ESI+: 913 |

TABLE 29-continued

| PEx | PSyn | Str | Data |
|---|---|---|---|
| 136 | P6 | (structure) | ESI+: 532 [M + Na]+ |

TABLE 30

| PEx | PSyn | Str | Data |
|---|---|---|---|
| 137 | P3 | (structure) | ESI+: 871 |
| 138 | P6 | (structure) # | ESI+: 518 [M + Na]+ |
| 139 | P3 | (structure) # | ESI+: 857 |

TABLE 30-continued
| PEx | PSyn | Str | Data |
|---|---|---|---|
| 140 | P17 | 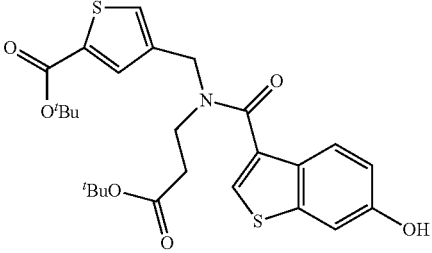 [SMILES: CC(C)(C)OC(=O)CCN(Cc1csc(C(=O)OC(C)(C)C)c1)C(=O)c1csc2cc(O)ccc12] | ESI+: 540 [M + Na]+ |
| 141 | P3 | 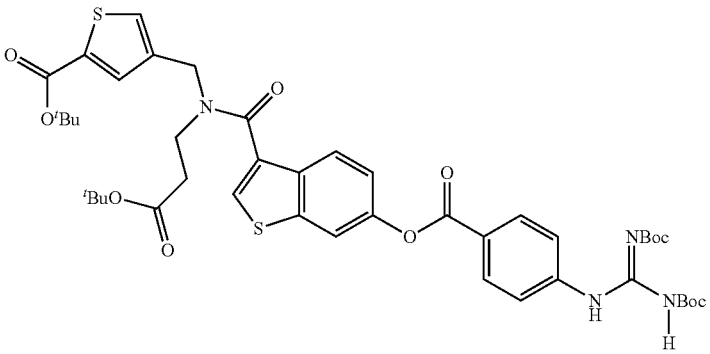 | ESI+: 879 |
TABLE 31
| PEx | PSyn | Str | Data |
|---|---|---|---|
| 142 | P2 | 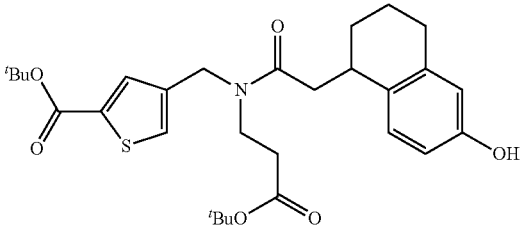 [SMILES: CC(C)(C)OC(=O)CCN(Cc1csc(C(=O)OC(C)(C)C)c1)C(=O)CC1CCCc2cc(O)ccc21] | ESI+: 530 |
| 143 | P3 | 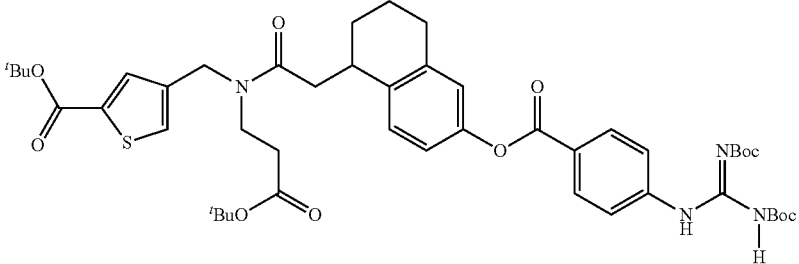 | ESI+: 891 |
| 144 | P2 | 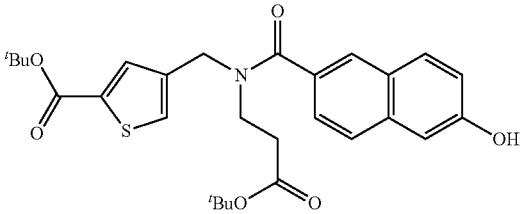 [SMILES: CC(C)(C)OC(=O)CCN(Cc1csc(C(=O)OC(C)(C)C)c1)C(=O)c1ccc2cc(O)ccc2c1] | ESI+: 534 [M + Na]+ |

TABLE 31-continued

| PEx | PSyn | Str | Data |
|-----|------|-----|------|
| 145 | P3 | | ESI+: 873 |

TABLE 32

| PEx | PSyn | Str | Data |
|-----|------|-----|------|
| 146 | P13 | | ESI+: 534 [M + Na]+ |
| 147 | P3 | | ESI+: 895 [M + Na]+ |

TABLE 33

| Ex | Str |
|---|---|
| 1 | (structure) |
| 2 | (structure) |
| 3 | (structure) |
| 4 | (structure) |

TABLE 34

| Ex | Str |
|---|---|
| 5 | (structure: 3-carboxybenzyl-N-(carboxymethyl)-acetamide linked to tetrahydronaphthalene-6-yl 4-guanidinobenzoate, HCl salt) ** |
| 6 | (structure: 3-carboxybenzyl-N-(carboxymethyl)-acetamide linked to tetrahydronaphthalene-6-yl 4-guanidinobenzoate, HCl salt) ** |
| 7 | (structure: 5-carboxythiophen-3-ylmethyl-N-((S)-1-carboxyethyl)-acetamide linked to tetrahydronaphthalene-6-yl 4-guanidinobenzoate, HCl salt) ** |
| 8 | (structure: 5-carboxythiophen-3-ylmethyl-N-((S)-1-carboxyethyl)-acetamide linked to tetrahydronaphthalene-6-yl 4-guanidinobenzoate) ** |

TABLE 35
| Ex | Str |
|---|---|
| 9 | 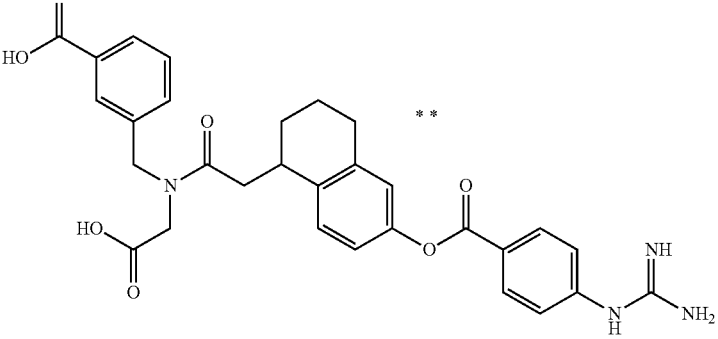 |
| 10 | 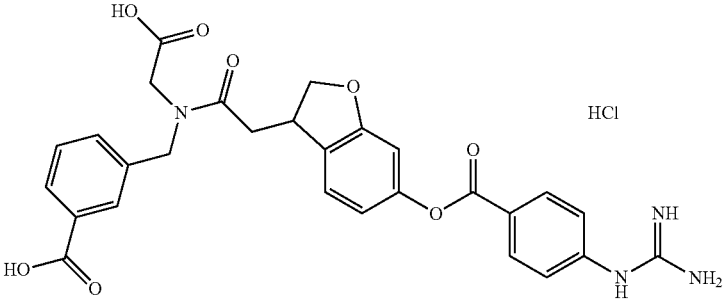 [SMILES: N=C(N)Nc1ccc(C(=O)Oc2ccc3c(c2)OCC3CC(=O)N(CC(=O)O)Cc2cccc(C(=O)O)c2)cc1 ; Cl] |
| 11 | 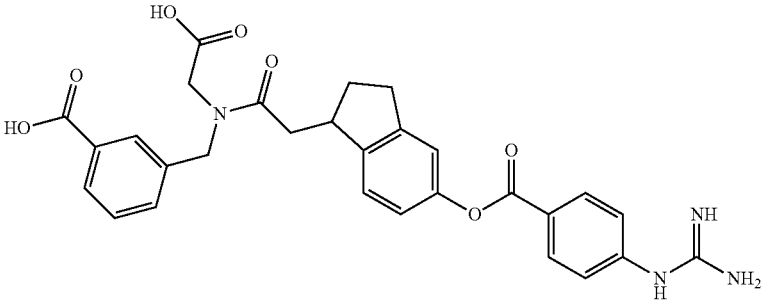 [SMILES: N=C(N)Nc1ccc(C(=O)Oc2ccc3c(c2)CCC3CC(=O)N(CC(=O)O)Cc2cccc(C(=O)O)c2)cc1] |
| 12 | 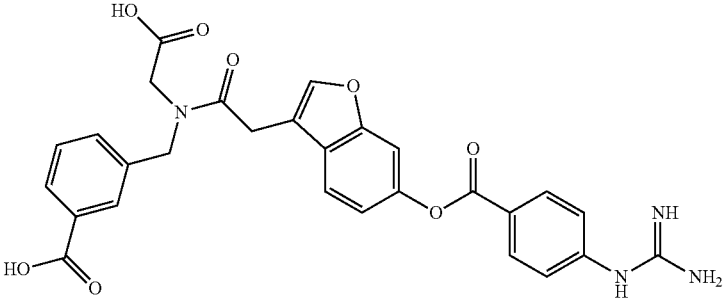 [SMILES: N=C(N)Nc1ccc(C(=O)Oc2ccc3c(CC(=O)N(CC(=O)O)Cc4cccc(C(=O)O)c4)coc3c2)cc1] |

TABLE 36
| Ex | Str |
|---|---|
| 13 | 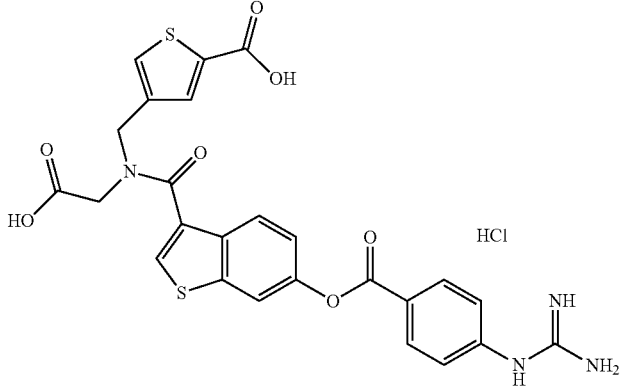 [SMILES: N=C(N)Nc1ccc(C(=O)Oc2ccc3c(C(=O)N(CC(=O)O)Cc4csc(C(=O)O)c4)csc3c2)cc1 ; Cl] HCl |
| 14 | 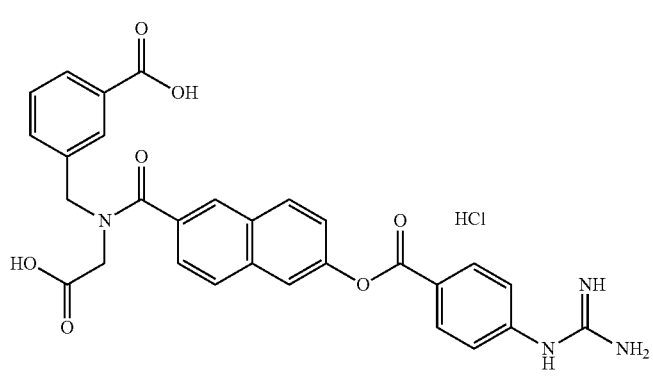 [SMILES: N=C(N)Nc1ccc(C(=O)Oc2ccc3cc(C(=O)N(CC(=O)O)Cc4cccc(C(=O)O)c4)ccc3c2)cc1 ; Cl] HCl |
| 15 | 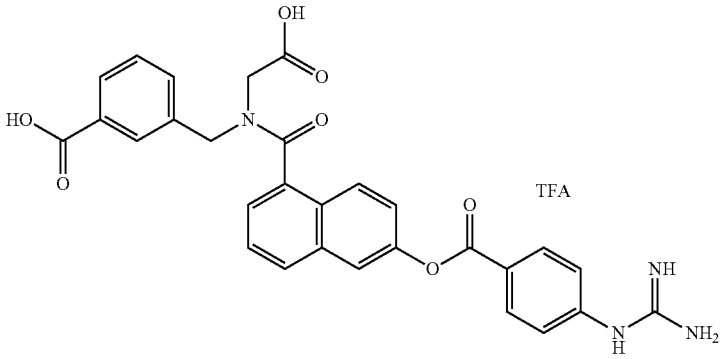 [SMILES: N=C(N)Nc1ccc(C(=O)Oc2ccc3c(C(=O)N(CC(=O)O)Cc4cccc(C(=O)O)c4)cccc3c2)cc1 ; "TFA"] TFA |
| 16 | 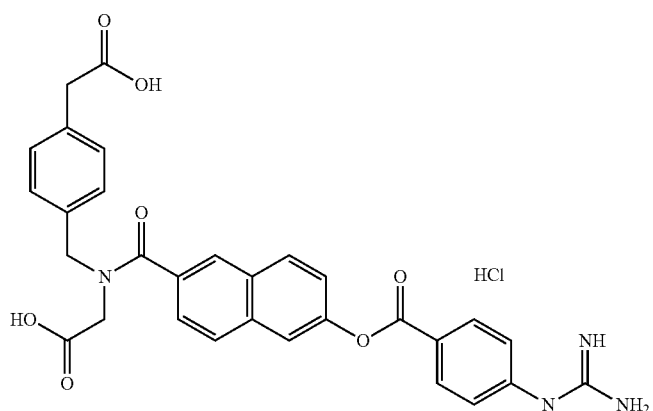 HCl |

TABLE 37

| Ex | Str |
|---|---|
| 17 | (structure) |
| 18 | (structure) * |
| 19 | (structure) # |
| 20 | (structure) |

TABLE 38
| Ex | Str |
|---|---|
| 21 | 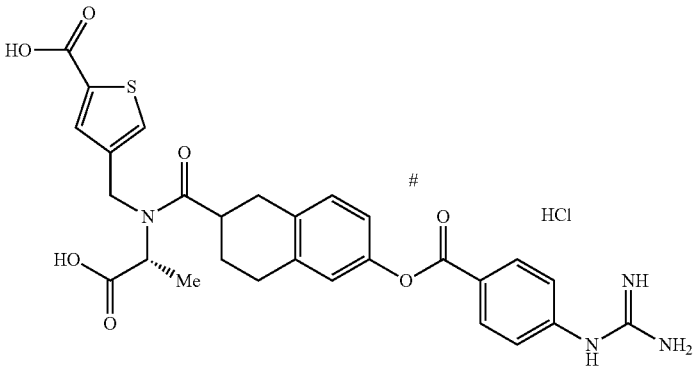 [SMILES: C[C@H](C(=O)O)N(Cc1csc(C(=O)O)c1)C(=O)C1CCc2cc(OC(=O)c3ccc(NC(=N)N)cc3)ccc2C1 ; Cl] HCl |
| 22 | 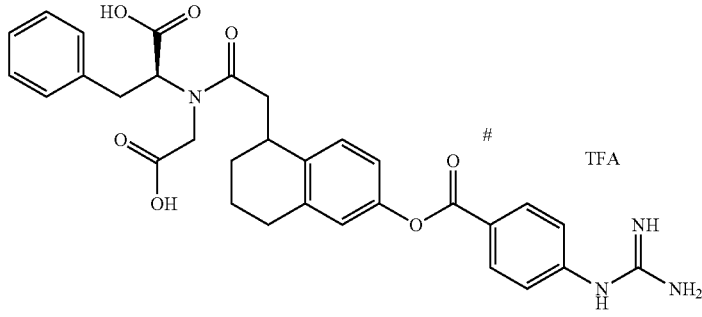 [SMILES: N=C(N)Nc1ccc(C(=O)Oc2ccc3c(c2)CCCC3CC(=O)N(CC(=O)O)[C@@H](Cc2ccccc2)C(=O)O)cc1 ; "TFA"] TFA |
| 23 | 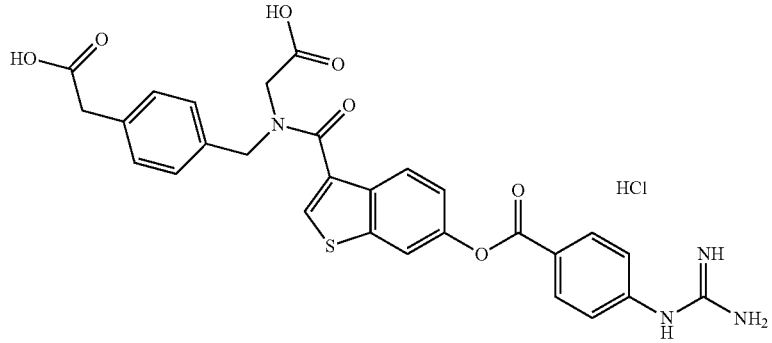 [SMILES: N=C(N)Nc1ccc(C(=O)Oc2ccc3c(C(=O)N(CC(=O)O)Cc4ccc(CC(=O)O)cc4)csc3c2)cc1 ; Cl] HCl |
TABLE 39
| Ex | Str |
|---|---|
| 24 | 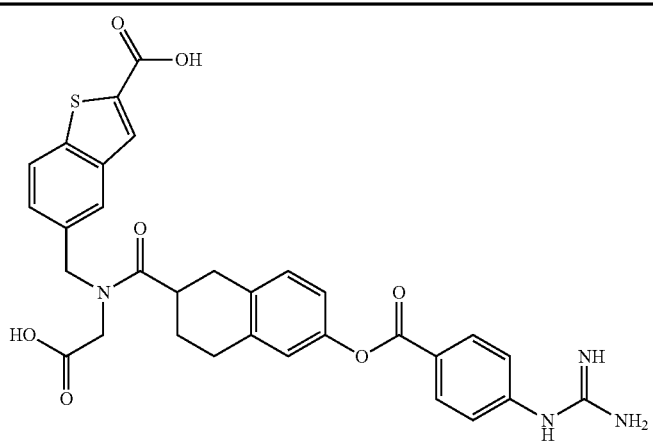 |

TABLE 39-continued
| Ex | Str |
|---|---|
| 25 | 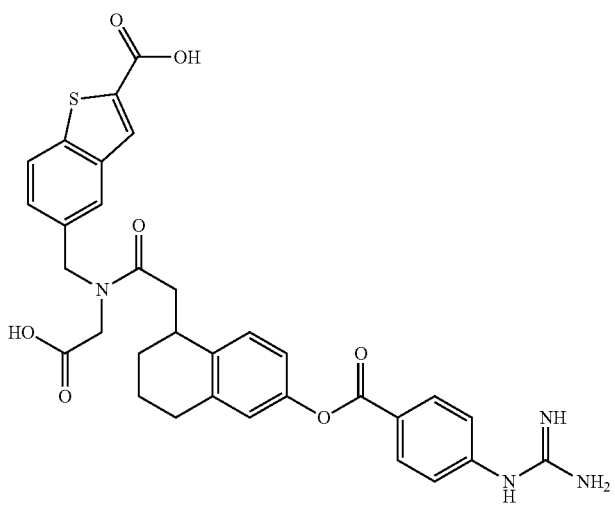 [SMILES: N=C(N)Nc1ccc(C(=O)Oc2ccc3c(c2)CCCC3CC(=O)N(CC(=O)O)Cc2ccc3sc(C(=O)O)cc3c2)cc1] |
| 26 | 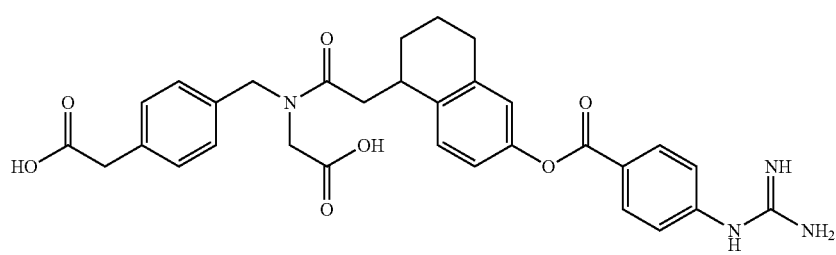 [SMILES: N=C(N)Nc1ccc(C(=O)Oc2ccc3c(c2)CCCC3CC(=O)N(CC(=O)O)Cc2ccc(CC(=O)O)cc2)cc1] |
| 27 | 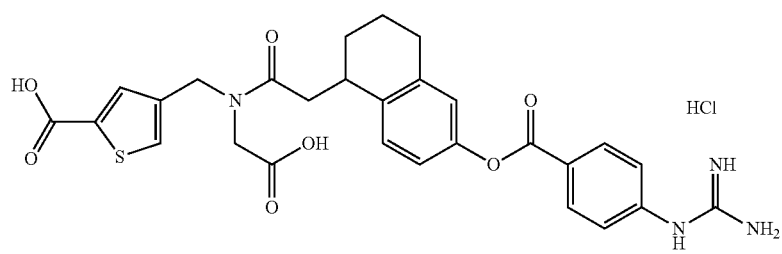 [SMILES: N=C(N)Nc1ccc(C(=O)Oc2ccc3c(c2)CCCC3CC(=O)N(CC(=O)O)Cc2csc(C(=O)O)c2)cc1 ; Cl] |
TABLE 40
| Ex | Str |
|---|---|
| 28 | 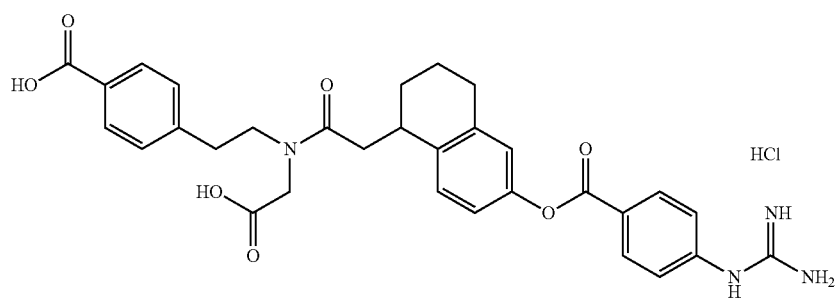 [SMILES: N=C(N)Nc1ccc(C(=O)Oc2ccc3c(c2)CCCC3CC(=O)N(CCc2ccc(C(=O)O)cc2)CC(=O)O)cc1 ; Cl] |

TABLE 40-continued
| Ex | Str |
|---|---|
| 29 | 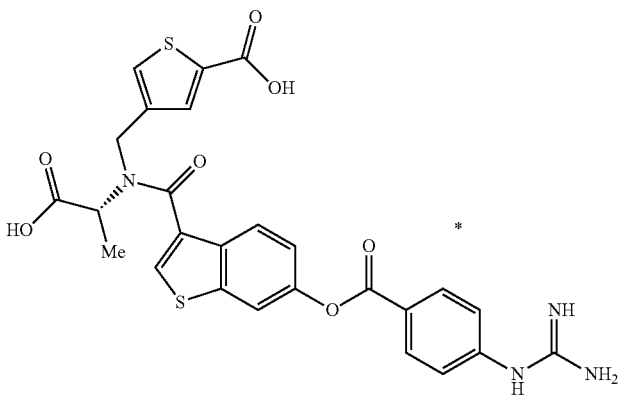 [SMILES: C[C@H](C(=O)O)N(Cc1csc(C(=O)O)c1)C(=O)c1csc2cc(OC(=O)c3ccc(NC(=N)N)cc3)ccc12] * |
| 30 | 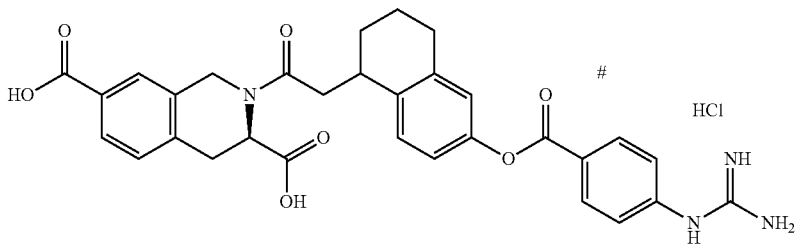 [SMILES: N=C(N)Nc1ccc(C(=O)Oc2ccc3c(c2)CCCC3CC(=O)N2Cc3cc(C(=O)O)ccc3C[C@@H]2C(=O)O)cc1 ; Cl] # HCl |
| 31 | 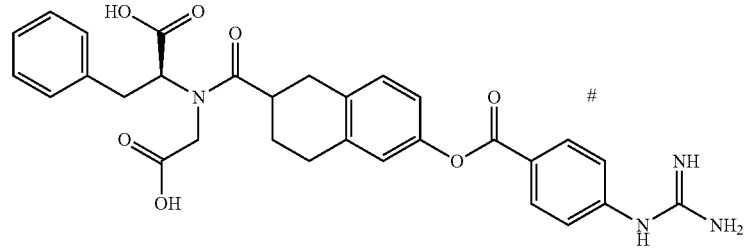 [SMILES: N=C(N)Nc1ccc(C(=O)Oc2ccc3c(c2)CCC(C(=O)N(CC(=O)O)[C@@H](Cc2ccccc2)C(=O)O)C3)cc1] # |
TABLE 41
| Ex | Str |
|---|---|
| 32 | 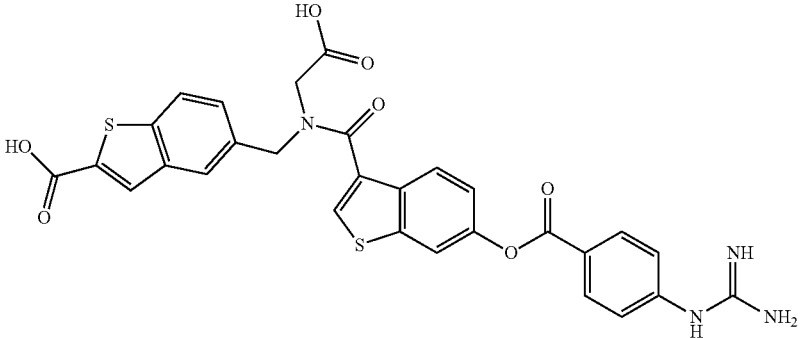 [SMILES: N=C(N)Nc1ccc(C(=O)Oc2ccc3c(C(=O)N(CC(=O)O)Cc4ccc5sc(C(=O)O)cc5c4)csc3c2)cc1] |

TABLE 41-continued

| Ex | Str |
|---|---|
| 33 | |
| 34 | |
| 35 | |

TABLE 42

| Ex | Str |
|---|---|
| 36 | |

TABLE 42-continued
| Ex | Str |
|---|---|
| 37 | 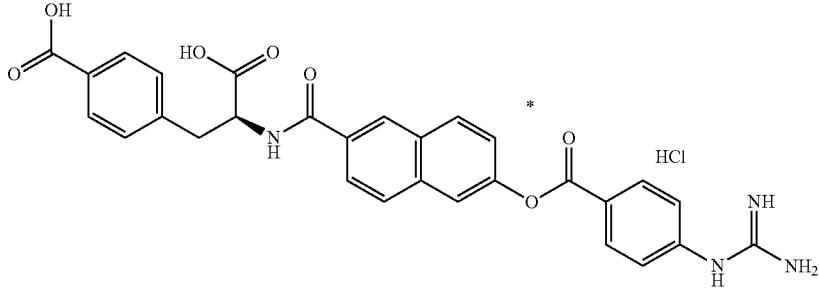 [SMILES: N=C(N)Nc1ccc(C(=O)Oc2ccc3cc(C(=O)N[C@@H](Cc4ccc(C(=O)O)cc4)C(=O)O)ccc3c2)cc1 ; Cl] |
| 38 | 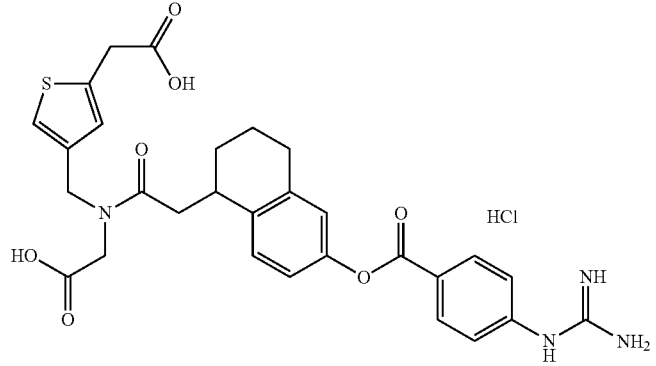 [SMILES: N=C(N)Nc1ccc(C(=O)Oc2ccc3c(c2)CCCC3CC(=O)N(CC(=O)O)Cc2csc(CC(=O)O)c2)cc1 ; Cl] |
| 39 | 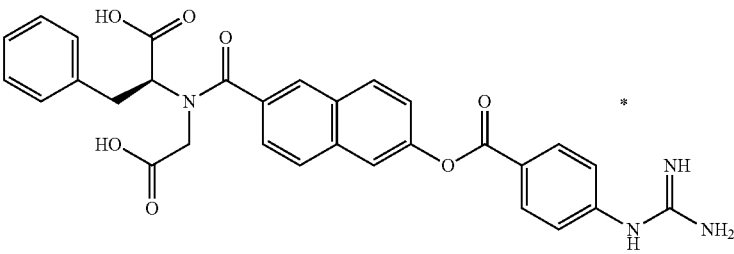 [SMILES: N=C(N)Nc1ccc(C(=O)Oc2ccc3cc(C(=O)N(CC(=O)O)[C@@H](Cc4ccccc4)C(=O)O)ccc3c2)cc1] |
TABLE 43
| Ex | Str |
|---|---|
| 40 | 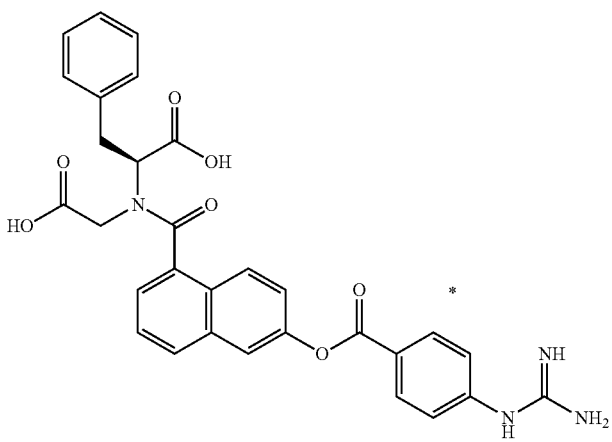 |

TABLE 43-continued
| Ex | Str |
|---|---|
| 41 | 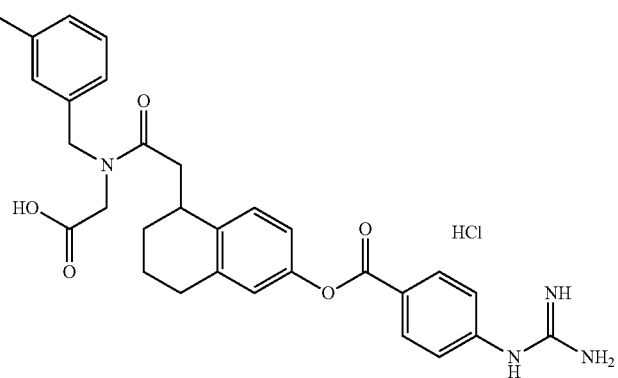 |
| 42 | 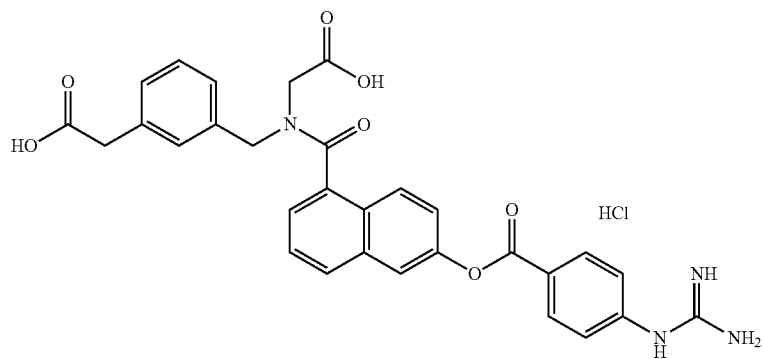 [SMILES: N=C(N)Nc1ccc(C(=O)Oc2ccc3c(C(=O)N(CC(=O)O)Cc4cccc(CC(=O)O)c4)cccc3c2)cc1 ; Cl] |
| 43 | 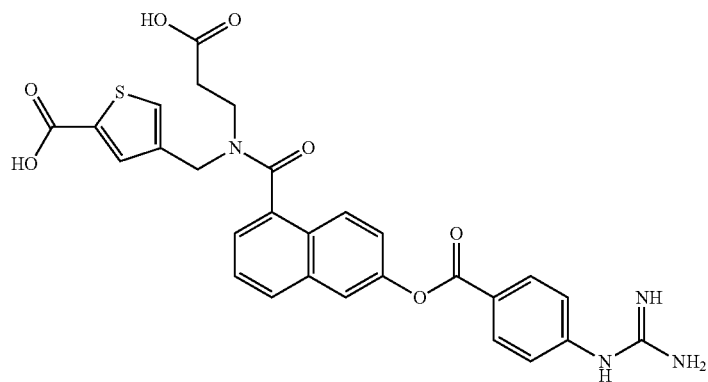 [SMILES: N=C(N)Nc1ccc(C(=O)Oc2ccc3c(C(=O)N(CCC(=O)O)Cc4csc(C(=O)O)c4)cccc3c2)cc1] |

TABLE 44
| Ex | Str |
|---|---|
| 44 | 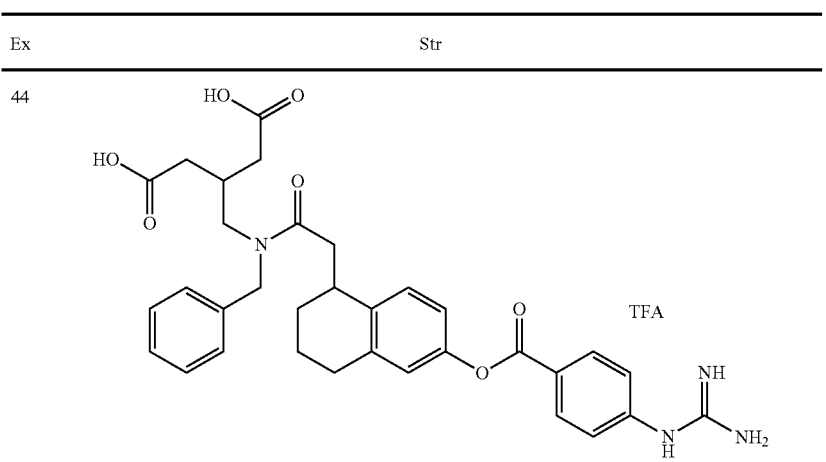 TFA |
| 45 | 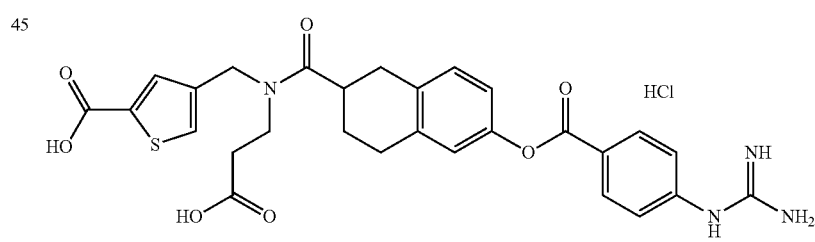 HCl |
| 46 | 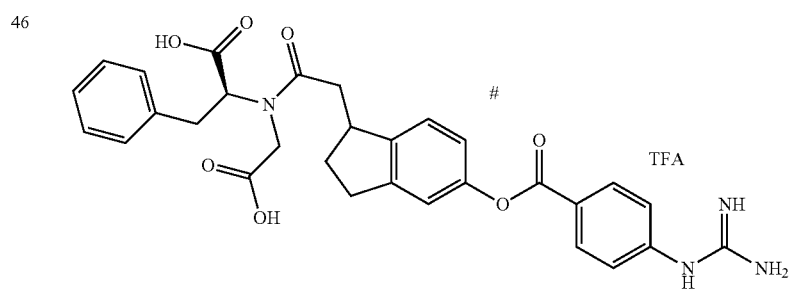 # TFA |
| 47 | 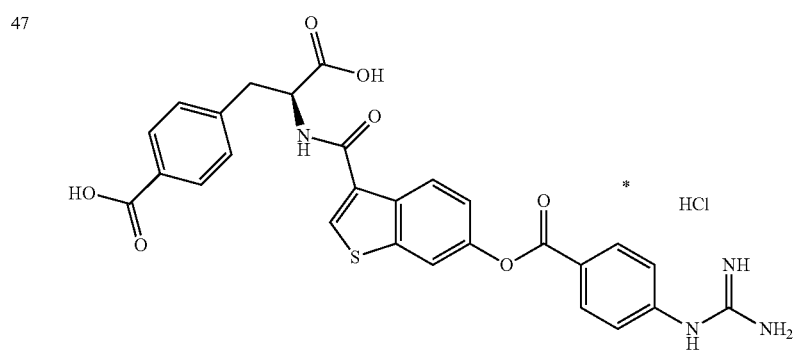 * HCl |

TABLE 45
| Ex | Str |
|---|---|
| 48 | 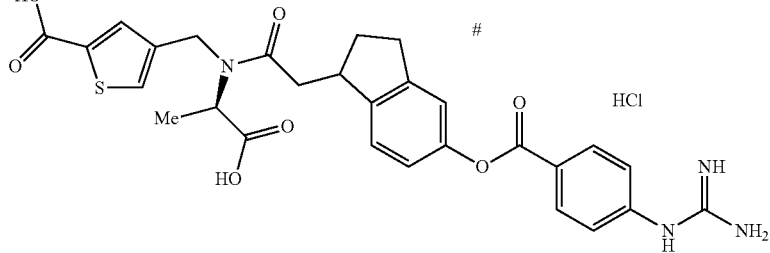 # |
| 49 | 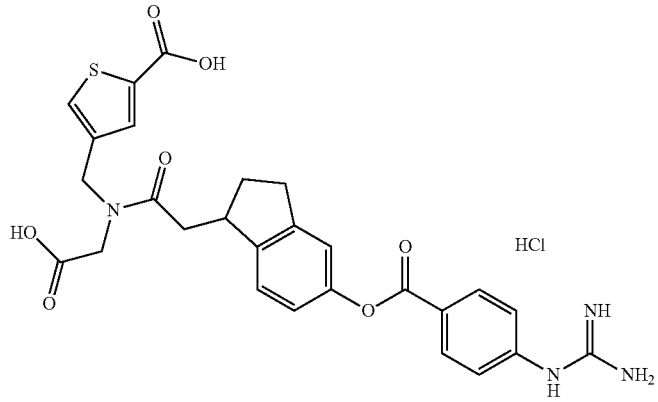 [SMILES: N=C(N)Nc1ccc(C(=O)Oc2ccc3c(c2)CCC3CC(=O)N(CC(=O)O)Cc2csc(C(=O)O)c2)cc1 ; Cl] |
| 50 | 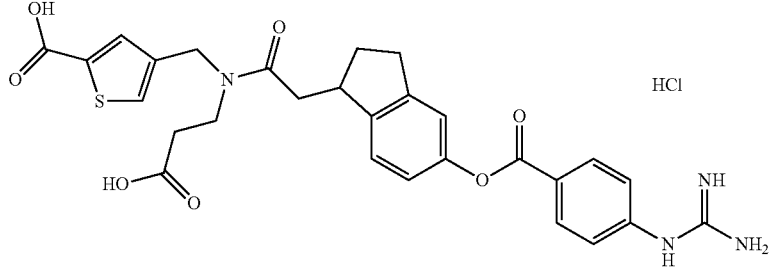 [SMILES: N=C(N)Nc1ccc(C(=O)Oc2ccc3c(c2)CCC3CC(=O)N(CCC(=O)O)Cc2csc(C(=O)O)c2)cc1 ; Cl] |
TABLE 46
| Ex | Str |
|---|---|
| 51 | 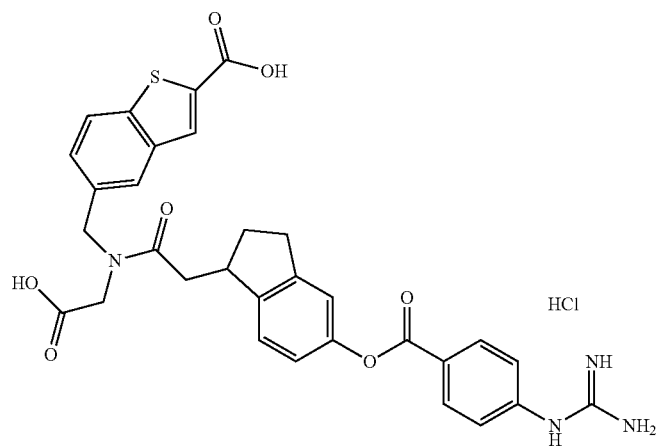 [SMILES: N=C(N)Nc1ccc(C(=O)Oc2ccc3c(c2)CCC3CC(=O)N(CC(=O)O)Cc2ccc3sc(C(=O)O)cc3c2)cc1 ; Cl] |

TABLE 46-continued
| Ex | Str |
|---|---|
| 52 | 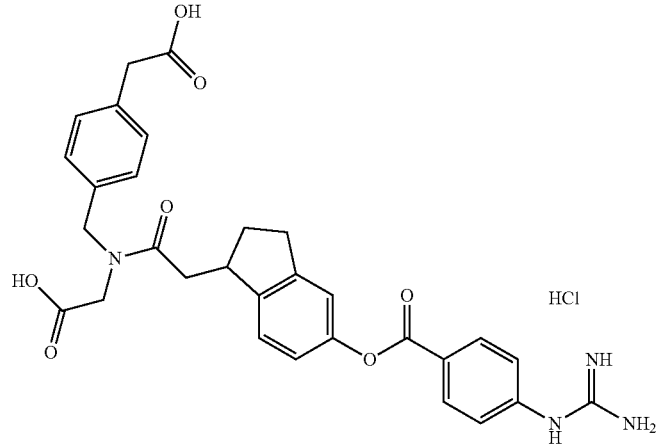 [SMILES: N=C(N)Nc1ccc(C(=O)Oc2ccc3c(c2)CCC3CC(=O)N(CC(=O)O)Cc2ccc(CC(=O)O)cc2)cc1 ; Cl] |
| 53 | 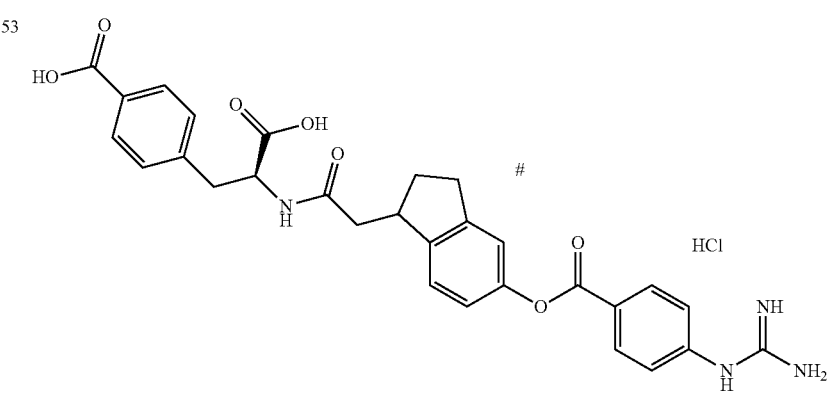 |
| 54 | 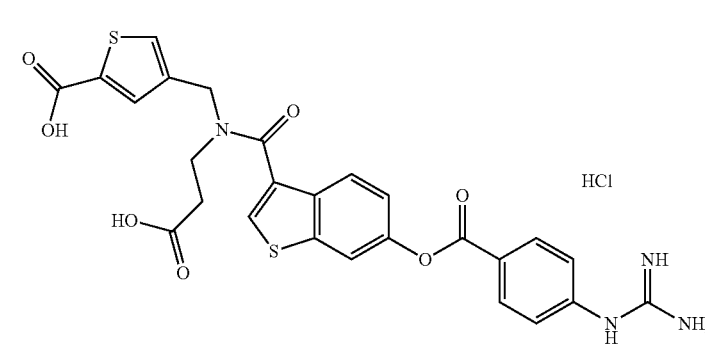 [SMILES: N=C(N)Nc1ccc(C(=O)Oc2ccc3c(C(=O)N(CCC(=O)O)Cc4csc(C(=O)O)c4)csc3c2)cc1 ; Cl] |
TABLE 47
| Ex | Str |
|---|---|
| 55 | 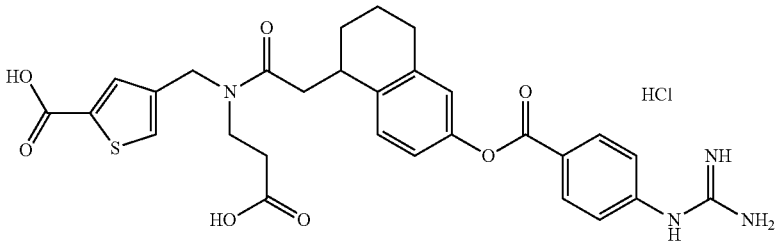 [SMILES: N=C(N)Nc1ccc(C(=O)Oc2ccc3c(c2)CCCC3CC(=O)N(CCC(=O)O)Cc2csc(C(=O)O)c2)cc1 ; Cl] |

TABLE 47-continued

| Ex | Str |
|---|---|
| 56 | |
| 57 | |
| 58 | |

TABLE 48

| Ex | Str |
|---|---|
| 59 | |

TABLE 48-continued

| Ex | Str |
|---|---|
| 60 | 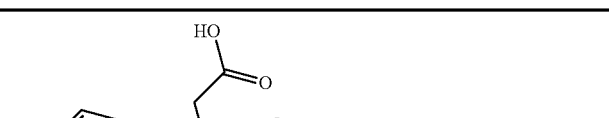 |

TABLE 49

| Ex | Syn | Data |
|---|---|---|
| 1 | 1 | ESI+: 547<br>NMR1: 4.00 (2H × 0.5, brs), 4.13 (2H × 0.5, brs), 4.55 (2H × 0.5, brs), 4.69 (2H × 0.5, brs), 7.43-7.60 (4H, m), 7.70-7.96 (3H, m), 7.82 (4H, brs), 7.98-8.12 (3H, m), 8.19-8.27 (2H, m), 10.20-10.56 (1H, br), 12.50-13.53 (2H, br) |
| 2 | 2 | ESI+: 559<br>NMR1: 1.50-1.92 (4H, m), 2.57-2.84 (4H, m), 3.28-3.44 (1H, m), 3.93-4.19 (2H, m), 4.57 (1H × 0.5, d, J = 15.1 Hz), 4.65 (1H × 0.5, d, J = 15.1 Hz), 4.69-4.82 (1H, m), 6.87-7.00 (2H, m), 7.23 (1H, dd, J = 8.5, 12.4 Hz), 7.39-7.57 (4H, m), 7.78-7.94 (6H, m), 8.10-8.17 (2H, m), 10.47 (1H, d, J = 3.8 Hz), 12.00-13.72 (2H, br) |
| 3 | 3 | ESI+: 541<br>NMR1: 3.09 (1H, dd, J = 11.0, 13.8 Hz), 3.27-3.38 (1H, m), 4.75-4.86 (1H, m), 7.37 (1H, dd, J = 2.4, 9.2 Hz), 7.42-7.51 (5H, m), 7.59 (1H, dd, J = 7.1, 8.2 Hz), 7.83 (4H, brs), 7.86-7.93 (3H, m), 7.95-8.05 (2H, m), 8.19-8.26 (2H, m), 8.93 (1H, d, J = 8.3 Hz), 10.20-10.81 (1H, br), 12.62-13.16 (2H, br) |
| 4 | 4 | ESI+: 551<br>NMR1: 1.58-1.99 (2H, m), 2.71-3.15 (5H, m), 3.93-4.09 (2H × 0.5, m), 4.15-4.30 (2H × 0.5, m), 4.50 (2H × 0.5, brs), 4.71 (2H × 0.5, brs), 6.93-7.01 (2H, m), 7.11-7.21 (1H, m), 7.39-7.46 (2H, m), 7.59-7.85 (2H, m), 7.78 (4H, brs), 8.10-8.17 (2H, m), 10.32 (1H, brs), 11.77-14.23 (2H, br) |
| 5 | 5 | ESI+: 559<br>NMR1: 1.48-1.90 (4H, m), 2.55-2.84 (4H, m), 3.30-3.41 (1H, m), 3.95-4.21 (2H, m), 4.57 (1H × 0.5, d, J = 15.1 Hz), 4.65 (1H × 0.5, d, J = 15.1 Hz), 4.69-4.82 (1H, m), 6.88-7.00 (2H, m), 7.23 (1H, dd, J = 8.5, 12.4 Hz), 7.38-7.58 (4H, m), 7.74-7.92 (6H, m), 8.08-8.18 (2H, m), 10.41 (1H, d, J = 3.8 Hz), 12.10-13.81 (2H, br) |
| 6 | 6 | ESI+: 559<br>NMR1: 1.50-1.92 (4H, m), 2.55-2.84 (4H, m), 3.34-3.44 (1H, m), 3.93-4.18 (2H, m), 4.57 (1H × 0.5, d, J = 15.1 Hz), 4.65 (1H × 0.5, d, J = 15.1 Hz), 4.69-4.82 (1H, m), 6.87-7.00 (2H, m), 7.23 (1H, dd, J = 8.5, 12.2 Hz), 7.36-7.56 (4H, m), 7.74-7.91 (6H, m), 8.08-8.17 (2H, m), 10.43 (1H, brs), 12.86 (2H, brs) |
| 7 | 7 | ESI+: 579 |
| 8 | 8 | ESI+: 579 |

TABLE 50

| Ex | Syn | Data |
|---|---|---|
| 9 | 9 | ESI+: 559<br>NMR1: 1.50-1.88 (4H, m), 2.53-2.73 (4H, m), 2.90-3.54 (1H, m), 3.55-3.70 (2H × 0.4, m), 3.76-4.07 (2H × 0.6, m), 4.43 (2H × 0.4, d, J = 15.2 Hz), 4.60-4.90 (2H × 0.6, m), 6.60-6.70 (2H × 0.4, m), 6.80-6.91 (2H × 0.6, m), 7.10-7.28 (1H, m), 7.30-7.52 (4H, m), 7.77-7.88 (2H, m), 8.07 (2H, d, J = 8.6 Hz), 8.17-8.80 (4H, br), 12.20-13.60 (2H, br) |
| 10 | 2 | ESI+: 547 |
| 11 | 2 | ESI+: 545<br>NMR1: 1.59-1.78 (1H, m), 2.24-2.40 (1H, m), 2.44-2.59 (1H, m), 2.65-2.90 (3H, m), 3.49-3.62 (1H, m), 3.70-4.10 (2H, m), 4.50-4.85 (2H, m), 6.77-6.85 (1H × 0.7, m), 6.86-6.93 (1H × 0.3, m), 6.98-7.05 (1H, m), 7.13-7.54 (5H, m), 7.79-7.89 (2H, m), 7.96-8.40 (6H, m), 11.02-13.60 (2H, br) |
| 12 | 2 | ESI+: 545 |
| 13 | 2 | ESI+: 553<br>NMR1: 4.08-4.20 (2H, m), 4.53 (2H × 0.5, brs), 4.72 (2H × 0.5, brs), 7.33-7.43 (1H, m), 7.43-7.49 (2H, m), 7.50-8.09 (5H, m), 7.80 (4H, brs), 8.17-8.23 (2H, m), 10.31 (1H, s), 12.62-13.35 (2H, m) |
| 14 | 2 | ESI+: 541 |
| 15 | 2 | ESI+: 541<br>NMR1: 3.53-5.19 (4H, m), 7.37-8.31 (14H, m), 7.83 (4H, brs), 10.33 (1H, s), 12.37-13.46 (2H, br) |
| 16 | 2 | ESI+: 555 |
| 17 | 2 | ESI+: 555<br>NMR1: 3.20-5.04 (6H, m), 7.04-8.30 (14H, m), 7.83 (4H, brs), 10.39 (1H, s), 11.72-13.46 (2H, br) |
| 18 | 2 | ESI+: 561 |
| 19 | 2 | ESI+: 579<br>NMR1: 1.19-1.36 (3H, m), 1.38-1.88 (4H, m), 2.31-2.81 (4H, m), 3.20-3.40 (1H, m), 4.08-4.86 (3H, m), 6.82-6.98 (2H, m), 7.12-7.30 (1H, m), 7.34-7.59 (4H, m), 7.97-8.40 (2H, m), 8.18 (4H, brs), 11.30-13.63 (2H, br) |
| 20 | 2 | ESI+: 559 |
| 21 | 2 | ESI+: 565<br>NMR1: 1.22-1.41 (3H, m), 1.58-2.02 (2H, m), 2.56-3.12 (5H, m), 4.10-4.97 (3H, m), 6.90-7.04 (2H, m), 7.08-7.24 (1H, m), 7.38-7.48 (2H, m), 7.55-7.94 (2H, m), 7.79 (4H, brs), 8.08-8.19 (2H, m), 10.33 (1H, s), 12.15-13.48 (2H, br) |
| 22 | 2 | ESI+: 573 |

TABLE 51

| Ex | Syn | Data |
|---|---|---|
| 23 | 2 | ESI+: 561<br>NMR1: 3.49-3.90(4H, m), 4.36(2H × 0.67, brs), 4.76(2H × 0.33, brs), 6.66-7.58(7H, m), 7.70-8.73(9H, m), 11.93-14.29(2H, m) |

TABLE 51-continued

| Ex | Syn | Data |
|---|---|---|
| 24 | 2 | ESI+: 601 |
| 25 | 2 | ESI+: 615 |
| 26 | 2 | ESI+: 573 |
| 27 | 2 | ESI+: 565 |
| 28 | 2 | ESI+: 573 |
| 29 | 2 | ESI+: 567 |
| 30 | 2 | ESI+: 571 |
| 31 | 2 | ESI+: 559 |
| 32 | 2 | ESI+: 603 |
| 33 | 2 | ESI+: 597 |
| 34 | 2 | ESI+: 597 |
| 35 | 2 | ESI+: 545 |
| 36 | 2 | ESI+: 559 |
| 37 | 2 | ESI+: 541 |
| 38 | 2 | ESI+: 579 |
| 39 | 2 | ESI+: 555 |
| 40 | 2 | ESI+: 555 |
| 41 | 2 | ESI+: 573 |
| 42 | 2 | ESI+: 555 |
| 43 | 2 | ESI+: 561 |
| 44 | 2 | ESI+: 601 |
| 45 | 2 | ESI+: 565 |
| 46 | 2 | ESI+: 559 |
| 47 | 2 | ESI+: 547 |
| 48 | 2 | ESI+: 565 |
| 49 | 2 | ESI+: 551 |
| 50 | 2 | ESI+: 565 |
| 51 | 2 | ESI+: 601 |
| 52 | 2 | ESI+: 559 |
| 53 | 2 | ESI+: 545 |
| 54 | 2 | ESI+: 567 |
| 55 | 2 | ESI+: 579 |
| 56 | 2 | ESI+: 561 |
| 57 | 2 | ESI+: 547 |
| 58 | 2 | ESI+: 545 |
| 59 | 1 | ESI+: 553 |
| 60 | 2 | ESI+: 547 |

INDUSTRIAL APPLICABILITY

The compound of Formula (I) or a salt thereof has a trypsin inhibitory action, and therefore, can be used as an agent for preventing and/or treating kidney diseases as an agent which will substitute low-protein diet therapy, and/or an agent for preventing and/or treating trypsin-related diseases such as chronic pancreatitis, gastroesophageal reflux disease, hepatic encephalopathy, and influenza.

The invention claimed is:

1. A compound of Formula (I) or a salt thereof:

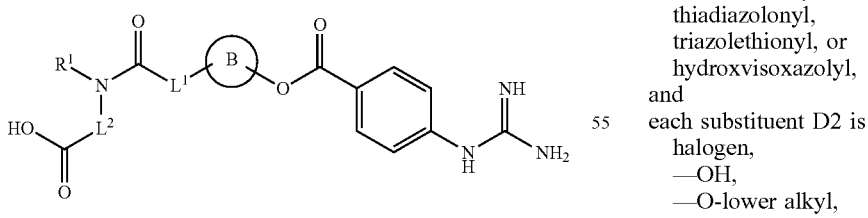

(I)

wherein
$L^1$ is a bond or -lower alkylene-,
$L^2$ is an optionally substituted lower alkylene,
$R^1$ is H or lower alkyl optionally substituted with at least one substituent selected from the group consisting of an optionally substituted aryl, an optionally substituted aromatic heterocyclic group, and —$CO_2H$, or $R^1$ with the nitrogen atom bonded thereto and the $HO_2C$-$L^2$ group on the nitrogen atom form a cyclic amino optionally substituted with —$CO_2H$, and Ring B is naphthalenediyl, 1,2,3,4-tetrahydronaphthalenediyl, 2,3-dihydroindenediyl, benzothiophenediyl, benzofurandiyl, or 2,3-dihydrobenzofurandiyl.

2. The compound or a salt thereof according to claim 1, wherein
$L^1$ is a bond or $C_{1-3}$ alkylene,
$L^2$ is lower alkylene optionally substituted with a substituent D1, and
$R^1$ is H or lower alkyl optionally substituted with at least one substituent selected from the group consisting of (i) aryl optionally substituted with a substituent D2, (ii) an aromatic heterocyclic group optionally substituted with a substituent D2, and (iii) —$CO_2H$, or $R^1$ with the nitrogen atom bonded thereto and the $HO_2C$-$L^2$ group on the nitrogen atom form, 1,2,3,4-tetrahydroisoquinolin-2-yl substituted with at least one —$CO_2H$ group,
the substituent D1 is
halogen,
—OH,
—O-lower alkyl,
—SH,
—S-lower alkyl,
—S(O)-lower alkyl,
—S(O)$_2$-lower alkyl,
—CN,
—NO$_2$,
—NH$_2$,
—NH-(lower alkyl),
—N(lower alkyl)$_2$,
—C(O)-lower alkyl,
aryl substituted with at least one substituent selected from the group consisting of —O-(lower alkyl optionally substituted with at least one —CO$_2$H group), halogen, —CO$_2$H, and lower alkyl which is optionally substituted with at least one substituent selected from the group consisting of halogen and —CO$_2$H,
—C(O)—O-lower alkyl,
—CO$_2$H,
—C(O)—NH—OH,
—C(O)—NH—O-lower alkyl,
—C(O)—NH—CN,
—C(O)—NH—S(O)$_2$-lower alkyl,
—C(O)—NH—S(O)$_2$—N(lower alkyl)$_2$,
tetrazolyl,
oxadiazolonyl,
oxadiazolethionyl,
oxathiadiazolyl,
thiadiazolonyl,
triazolethionyl, or
hydroxyisoxazolyl,
and
each substituent D2 is independently
halogen,
—OH,
—O-lower alkyl,
—SH,
—S-lower alkyl,
—S(O)-lower alkyl,
—S(O)$_2$-lower alkyl,
—CN,
—NO$_2$,
—NH$_2$,
—NH-(lower alkyl),
—N(lower alkyl)$_2$, —C(O)-lower alkyl,
—C(O)—NH$_2$,
—C(O)—NH-(lower alkyl),
—C(O)—N(lower alkyl)$_2$,
—C(O)—O-lower alkyl,
—CO$_2$H,
—C(O)—NH—OH,
—C(O)—NH—O-lower alkyl,
—C(O)—NH—CN,
—C(O)—NH—S(O)$_2$-lower alkyl,
—C(O)—NH—S(O)$_2$—N(lower alkyl)$_2$,
tetrazolyl,
oxadiazolonyl,
oxadiazolethionyl,
oxathiadiazolyl,
thiadiazolonyl,
triazolethionyl, or
hydroxyisoxazolyl,
lower alkyl optionally substituted with halogen, —OH, —O-lower alkyl, —SH, —S-lower alkyl, —S(O)-lower alkyl, —S(O)$_2$-lower alkyl, —CN, —NO$_2$, —NH$_2$, —NH-(lower alkyl), —N(lower alkyl)$_2$, —C(O)-lower alkyl, —C(O)—NH$_2$, —C(O)—NH-(lower alkyl), —C(O)—N(lower alkyl)$_2$, —C(O)—O-lower alkyl, —CO$_2$H, —C(O)—NH—OH, —C(O)—NH—O-lower alkyl, —C(O)—NH—CN, —C(O)—NH—S(O)$_2$-lower alkyl, —C(O)—NH—S(O)$_2$—N(lower alkyl)$_2$, tetrazolyl, oxadiazolonyl, oxadiazolethionyl, oxathiadiazolyl, thiadiazolonyl, triazolethionyl, or hydroxyisoxazolyl, or
—O-lower alkyl optionally substituted with halogen, —OH, —O-lower alkyl, —SH, —S-lower alkyl, —S(O)-lower alkyl, —S(O)$_2$-lower alkyl, —CN, —NO$_2$, —NH$_2$, —NH-(lower alkyl), —N(lower alkyl)$_2$, —C(O)-lower alkyl, —C(O)—NH$_2$, —C(O)—NH-(lower alkyl), —C(O)—N(lower alkyl)$_2$, —C(O)—O-lower alkyl, —CO$_2$H, —C(O)—NH—OH, —C(O)—NH—O-lower alkyl, —C(O)—NH—CN, —C(O)—NH—S(O)$_2$-lower alkyl, —C(O)—NH—S(O)$_2$—N(lower alkyl)$_2$, tetrazolyl, oxadiazolonyl, oxadiazolethionyl, oxathiadiazolyl, thiadiazolonyl, triazolethionyl, or hydroxyisoxazolyl.

3. The compound or a salt thereof according to claim 2, wherein L$^1$ is a bond or methylene,
L$^2$ is lower alkylene optionally substituted with a substituent
R$^1$ is H or lower alkyl optionally substituted with at least one substituent selected from the group consisting of (i) aryl optionally substituted with a substituent D2, (ii) an aromatic heterocyclic group optionally substituted with a substituent D2, and (iii) —CO$_2$H,
Ring B is naphthalenediyl, 1,2,3,4-tetrahydronaphthalenediyl, 2,3-dihydroindenediyl, or benzothiophenediyl.

4. The compound or a salt thereof according to claim 3, wherein L$^2$ is methylene, ethylene, or ethylene substituted with (phenyl substituted with —CO$_2$H).

5. The compound or a salt thereof according to claim 3, wherein L$^2$ is methylene, methylmethylene, ethylene, or methylmethylene substituted with (phenyl substituted with —CO$_2$H).

6. The compound or a salt thereof according to claim 4, wherein R$^1$ is H or lower alkyl optionally substituted with at least one substituent selected from the group consisting of (i) phenyl substituted with at least one substituent selected from the group consisting of —CO$_2$H and lower alkyl substituted with —CO$_2$H,
(ii) thienyl substituted with at least one substituent selected from the group consisting of —CO$_2$H and lower alkyl substituted with —CO$_2$H, and
(iii) —CO$_2$H.

7. The compound or a salt thereof according to claim 6, wherein Ring B is naphthalene-1,6-diyl, naphthalene-2,6-diyl, 1,2,3,4-tetrahydronaphthalene-1,6-diyl, 1,2,3,4-tetrahydronaphthalene-2,6-diyl, 2,3-dihydroindene-1,5-diyl, or benzothiophene-3,6-diyl.

8. The compound or a salt thereof according to claim 7, wherein either
L$^2$ is methylene or methylmethylene, and R$^1$ is lower alkyl substituted with at least one substituent selected from the group consisting of
(i) phenyl substituted with at least one substituent selected from the group consisting of —CO$_2$H and lower alkyl substituted with —CO$_2$H, and
(ii) thienyl substituted with at least one substituent selected from the group consisting of —CO$_2$H and lower alkyl substituted with —CO$_2$H,
or
L$^2$ is methylmethylene substituted with (phenyl substituted with —CO$_2$H), and R$^1$ is H.

9. The compound or a salt thereof according to claim 8, wherein L$^2$ is methylene or methylmethylene, and R$^1$ is (phenyl substituted with —CO$_2$H)—CH$_2$—, (phenyl substituted with —CH$_2$—CO$_2$H)—CH$_2$—, or (thienyl substituted with —CO$_2$H)—CH$_2$—.

10. The compound or a salt thereof according to claim 2, wherein
L$^1$ is a bond or methylene, Ring B is naphthalene-1,6-diyl, naphthalene-2,6-diyl, 1,2,3,4-tetrahydronaphthalene-1,6-diyl, 1,2,3,4-tetrahydronaphthalene-2,6-diyl, 2,3-dihydroindene-1,5-diyl, benzothiophene-3,6-diyl, benzofuran-3,6-diyl, or 2,3-dihydrobenzofuran-3,6-diyl, and
(a) L$^2$ is C$_{1-3}$ alkylene, and R$^1$ is lower alkyl which is substituted with at least one substituent selected from the group consisting of (i) phenyl optionally substituted with at least one substituent selected from the group consisting of —CO$_2$H and lower alkyl substituted with —CO$_2$H, and (ii) thienyl or benzothienyl, either of which is substituted with at least one substituent selected from the group consisting of —CO$_2$H and lower alkyl substituted with —CO$_2$H, the lower alkyl of R$^1$ optionally substituted with at least one —CO$_2$H group,
(b) L$^2$ is C$_{1-3}$ alkylene substituted with (phenyl substituted with —CO$_2$H), and R$^1$ is H, or
(c) R$^1$ with the nitrogen atom bonded thereto and the HO$_2$C-L$^2$ group on the nitrogen atom form 1,2,3,4-tetrahydroisoquinolin-2-yl substituted with two —CO$_2$H groups.

11. The compound or a salt thereof according to claim 1, which is
4-{[{6-[(4-carbamimidamidobenzoyl)oxy]-2-naphthoyl}(carboxymethyl)amino]methyl}thiophene-2-carboxylic acid,
3-{[({6-[(4-carbamimidamidobenzoyl)oxy]-1,2,3,4-tetrahydronaphthalen-1-yl}acetyl)(carboxymethyl)amino]methyl}benzoic acid,
3-{[({(1R)-6-[(4-carbamimidamidobenzoyl)oxy]-1,2,3,4-tetrahydronaphthalen-1-yl}acetyl)(carboxymethyl)amino]methyl}benzoic acid, 3-{[({(1 S)-6-[(4-carbamimidamidobenzoyl)oxy]-1,2,3,4-tetrahydronaphthalen-1-yl}acetyl)(carboxymethyl)amino]methyl}benzoic acid, N-{6-[(4-carbamimidamidobenzoyl)oxy]-1-naphthoyl-4-carboxy-L-phenylalanine, 4-{[({6-[(4-carbamimidamidobenzoyl)oxy]-1,2,3,4-tetrahydronaphthalen-2-yl}carbonyl)(carboxymethyl)amino]methyl}thiophene-2-carboxylic acid, 3-{[({5-[(4-carbamimidamidobenzoyl)oxy]-2,3-dihydro-1H-inden-1-yl}acetyl)(carboxymethyl)amino]methyl}benzoic acid, 4-{[({6-[(4-carbamimidamidobenzoyl)oxy]-1-benzothiophen-3-yl}carbonyl)(carboxymethyl)amino]methyl}thiophene-2-carboxylic acid, 3-{[{6-[(4-carbamimidamidobenzoyl)oxy]-1-naphthoyl}(carboxymethyl)amino]methyl}benzoic acid, N-{6-[(4-carbamimidamidobenzoyl)oxy]-1-naphthoyl}-N-[4-(carboxymethyl)benzyl]glycine, 4-({({6-[(4-carbamimidamidobenzoyl)oxy]-1,2,3,4-tetrahydronaphthalen-1-yl}acetyl)[(1R)-1-carboxyethyl]amino}methyl)thiophene-2-carboxylic acid, 4-({({6-[(4-carbamimidamidobenzoyl)oxy]-1,2,3,4-tetrahydronaphthalen-2-yl}carbonyl)[(1R)-1-carboxyethyl]amino}methyl)thiophene-2-carboxylic acid, or N-({6-[(4-carbamimidamidobenzoyl)oxy]-1-benzothiophen-3-yl}carbonyl)-N-[4-(carboxymethyl)benzyl]glycine.

12. A pharmaceutical composition comprising a compound or a salt thereof according to claim 11, and a pharmaceutically acceptable excipient.

13. A method for treating a kidney disease, the method comprising:
administering an effective amount of a compound or a salt thereof according to claim 11 to a subject in need thereof.

14. The compound or a salt thereof according to claim 11 wherein the compound is 3-{[({(1R)-6-[(4-carbamimidamidobenzoyl)oxy]-1,2,3,4-tetrahydronaphthalen-1-yl}acetyl)(carboxymethyl)amino]methyl}benzoic acid.

15. The compound or a salt thereof according to claim 11 wherein the compound is 4-[({6-[(4-carbamimidamidobenzoyl)oxy]-1,2,3,4-tetrahydronaphthalen-2-yl}carbonyl)(carboxymethyl)amino]methyllthiophene-2-carboxylic acid.

16. The compound or a salt thereof according to claim 11 wherein the compound is 3-{[({5-[(4-carbamimidamidobenzoyl)oxy]-2,3-dihydro-1H-inden-1-yl}acetyl)(carboxymethyl)amino]methyl}benzoic acid.

17. The compound or a salt thereof according to claim 1, which is 3-{[({6-[(4-carbamimidamidobenzoyl)oxy]-1,2,3,4-tetrahydronaphthalen-1-yl}acetyl)(carboxymethyl)amino]methyl}benzoic acid.

18. The compound or a salt thereof according to claim 1, which is 3-{[({6-[(4-carbamimidamidobenzoyl)oxy]-2,3-dihydro-1-benzofuran-3-yl}acetyl)(carboxymethyl)amino]methyl}benzoic acid.

19. The compound or a salt thereof according to claim 1, which is 3-{[({5-[(4-carbamimidamidobenzoyl)oxy]-2,3-dihydro-1H-inden-1-yl}acetyl)(carboxymethyl)amino]methyl}benzoic acid.

20. The compound or a salt thereof according to claim 1, which is 3-{[({6-[(4-carbamimidamidobenzoyl)oxy]-1-benzofuran-3-yl}acetyl)(carboxymethyl)amino]methyl}benzoic acid.

21. The compound or a salt thereof according to claim 1, which is 3-{[({6-[(4-carbamimidamidobenzoyl)oxy]-2-naphthoyl)(carboxymethyl)amino]methyl}benzoic acid.

22. The compound or a salt thereof according to claim 1, which is 4-{[({6-[(4-carbamimidamidobenzoyl)oxy]-1,2,3,4-tetrahydronaphthalen-1-yl}acetyl)(carboxymethyl)amino]methyl}thiophene-2-carboxylic acid.

23. The compound or a salt thereof according to claim 1, which is 3-{[({6-[(4-carbamimidamidobenzoyl)oxy]-1,2,3,4-tetrahydronaphthalen-2-yl}carbonyl)(carboxymethyl)amino]methyl}benzoic acid.

\* \* \* \* \*